(12) United States Patent
Nomura et al.

(10) Patent No.: US 8,507,695 B2
(45) Date of Patent: Aug. 13, 2013

(54) CARBAZOLE DERIVATIVE, LIGHT-EMITTING ELEMENT MATERIAL, LIGHT-EMITTING ELEMENT, LIGHT-EMITTING DEVICE, ELECTRONIC DEVICE, AND LIGHTING DEVICE

(75) Inventors: Hiroko Nomura, Fukuoka (JP); Harue Osaka, Sagamihara (JP); Takahiro Ushikubo, Atsugi (JP); Satoshi Seo, Kawasaki (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 751 days.

(21) Appl. No.: 12/748,532

(22) Filed: Mar. 29, 2010

(65) Prior Publication Data
US 2010/0245217 A1    Sep. 30, 2010

(30) Foreign Application Priority Data

Mar. 31, 2009 (JP) .................... 2009-085233

(51) Int. Cl.
C07D 209/82 (2006.01)
B32B 9/00 (2006.01)
H01J 1/62 (2006.01)

(52) U.S. Cl.
USPC ........... 548/440; 548/427; 428/690; 428/917; 315/169.3; 313/504; 313/506

(58) Field of Classification Search
USPC ......... 548/427, 440; 428/690, 917; 313/504, 313/506; 315/169.3
See application file for complete search history.

(56) References Cited

U.S. PATENT DOCUMENTS

| | | | |
|---|---|---|---|
| 8,247,575 B2 * | 8/2012 | Nomura et al. .............. | 548/143 |
| 2007/0075632 A1 | 4/2007 | Kawakami et al. | |
| 2007/0149784 A1 | 6/2007 | Murata et al. | |
| 2008/0099757 A1 | 5/2008 | Furukawa et al. | |
| 2008/0124572 A1 | 5/2008 | Mizuki et al. | |
| 2008/0254318 A1 | 10/2008 | Nakashima et al. | |
| 2008/0268284 A1 | 10/2008 | Kawakami et al. | |
| 2008/0284328 A1 | 11/2008 | Nakashima et al. | |
| 2009/0058267 A1 | 3/2009 | Nakashima et al. | |

FOREIGN PATENT DOCUMENTS

| | | |
|---|---|---|
| CN | 101293865 | 10/2008 |
| EP | 1985613 A | 10/2008 |
| WO | WO-2008/062636 | 5/2008 |

OTHER PUBLICATIONS

Ho.M et al., "P-131: Novel Deep Blue Dopants for Organic Light Emitting Devices,", SID Digest '05 : SID International Symposium Digest of Technical Papers, May 24, 2005, vol. 36, pp. 802-805.
Chinese Office Action (Application No. 201010157358.7) Dated Apr. 24, 2013.

* cited by examiner

Primary Examiner — Golam M M Shameem
(74) Attorney, Agent, or Firm — Eric J. Robinson; Robinson Intellectual Property Law Office, P.C.

(57) ABSTRACT

A carbazole derivative represented by the general formula (1) is provided. In the formula, $Ar^1$ represents a substituted or unsubstituted aryl group having 6 to 10 carbon atoms which form a ring; $\alpha$ and $\beta$ independently represent a substituted or unsubstituted arylene group having 6 to 12 carbon atoms which form a ring; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring.

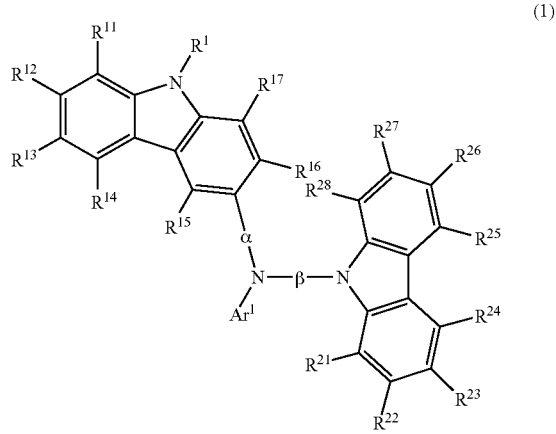

(1)

54 Claims, 27 Drawing Sheets

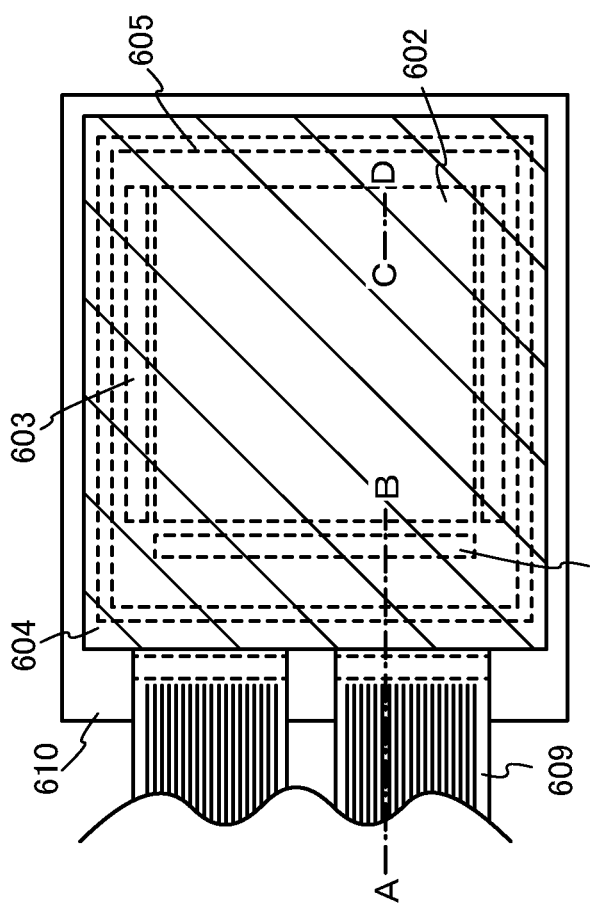
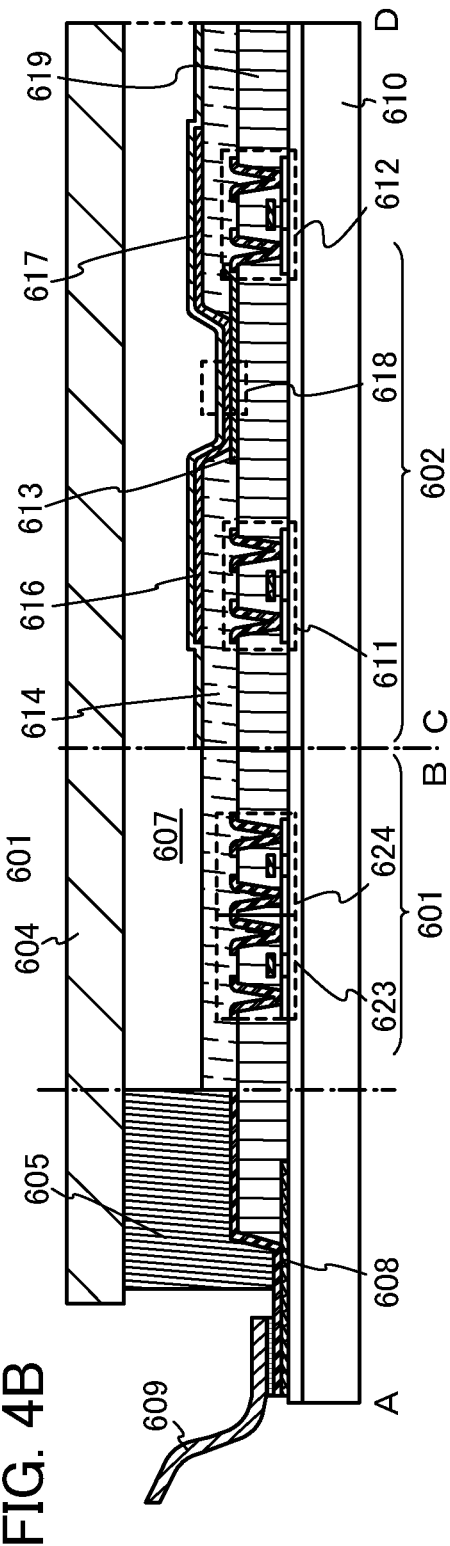
FIG. 4A
FIG. 4B

CARBAZOLE DERIVATIVE, LIGHT-EMITTING ELEMENT MATERIAL, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a carbazole derivative. In addition, the present invention relates to a material for a light-emitting element, a light-emitting element, an electronic device, and a lighting device each of which uses the carbazole derivative.

2. Description of the Related Art

In recent years, research and development have been extensively conducted on light-emitting elements utilizing, electroluminescence. In a basic structure of such a light-emitting element, a layer containing a light-emitting substance is interposed between a pair of electrodes. By voltage application to this element, light emission can be obtained from the light-emitting substance.

Since such a light-emitting element is a self-light-emitting type, it has advantages over a liquid crystal display in that visibility of pixels is high, a backlight is not required, and so on. Accordingly, such a light-emitting element is considered suitable as a flat panel display element. In addition, other advantages of such a light-emitting element are that it can be manufactured to be thin and lightweight and the response speed is very high.

Furthermore, since such a light-emitting element can be formed into a film form, planar light emission can be easily obtained by forming a large-area element. This feature cannot be easily obtained by point light sources typified by an incandescent lamp and an LED or linear light sources typified by a fluorescent lamp. Accordingly, the light-emitting element is extremely effective for use as a surface light source applicable to lighting and the like.

Light-emitting elements utilizing electroluminescence are broadly classified according to whether they use an organic compound or an inorganic compound as a light-emitting substance. When an organic compound is used as a light-emitting substance, by voltage application to a light-emitting element, electrons and holes are injected into a layer including the light-emitting organic compound from a pair of electrodes, whereby current flows. The carriers (electrons and holes) are recombined, and thus, the light-emitting organic compound is excited. The light-emitting organic compound returns to a ground state from the excited state, thereby emitting light.

Because of such a mechanism, the light-emitting element is referred to as a current-excitation light-emitting element. Note that the excited state of an organic compound can be either a singlet excited state or a triplet excited state, and light emission from the singlet excited state is referred to as fluorescence, and light emission from the triplet excited state is referred to as phosphorescence.

In improving element characteristics of such a light-emitting element, there are a lot of problems which depend on a substance, and in order to solve the problems, improvement of an element structure, development of a substance, and the like have been carried out (for example, see Non-Patent Document 1).

REFERENCE

[Non-Patent Document]

[Non-Patent Document 1] Meng-Huan Ho, Yao-Shan Wu and Chin H. Chen, 2005 SID International Symposium Digest of Technical Papers, Vol. XXXVI. pp. 802-805

SUMMARY OF THE INVENTION

Therefore, it is an object to provide a novel material having a hole-transporting property.

It is another object to provide a light-emitting element with high light emission efficiency.

It is another object to reduce power consumption of a light-emitting element, a light-emitting device, an electronic device, and a lighting device.

An aspect of the present invention is a carbazole derivative represented by the general formula (1).

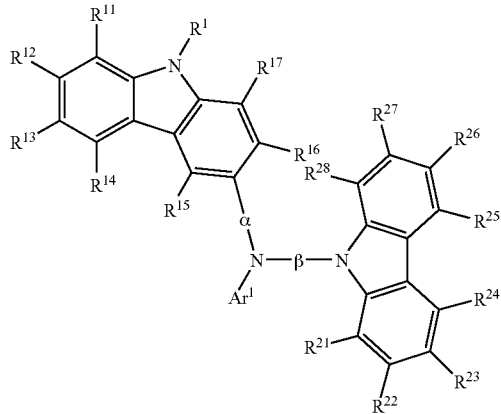

(1)

In the formula, $Ar^1$ represents a substituted or unsubstituted aryl group having 6 to 10 carbon atoms which form a ring; α and β independently represent a substituted or unsubstituted arylene group having 6 to 12 carbon atoms which form a ring; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

Another aspect of the present invention is a carbazole derivative represented by the general formula (2).

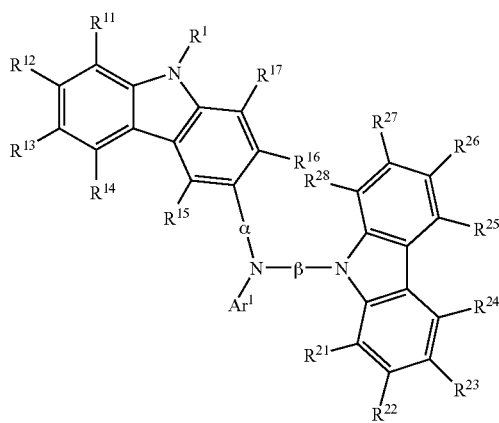

(2)

In the formula, $Ar^1$ represents a substituted or unsubstituted aryl group having 6 to 10 carbon atoms which form a ring; α and β independently represent a substituted or unsubstituted phenylene group; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or a substituted or unsubstituted aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

Another aspect of the present invention is a carbazole derivative represented by the general formula (3).

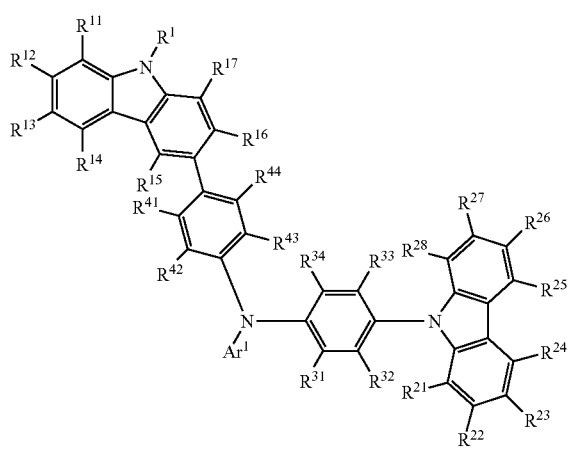

(3)

In the formula, $Ar^1$ represents a substituted or unsubstituted aryl group having 6 to 10 carbon atoms which form a ring; $R^1$ represents an alkyl group having 1 to 4 carbon atoms or a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; and $R^{31}$ to $R^{34}$ and $R^{41}$ to $R^{44}$ independently represent hydrogen or an alkyl group having 1 to 4 carbon atoms. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

Another aspect of the present invention is a carbazole derivative represented by the general formula (4).

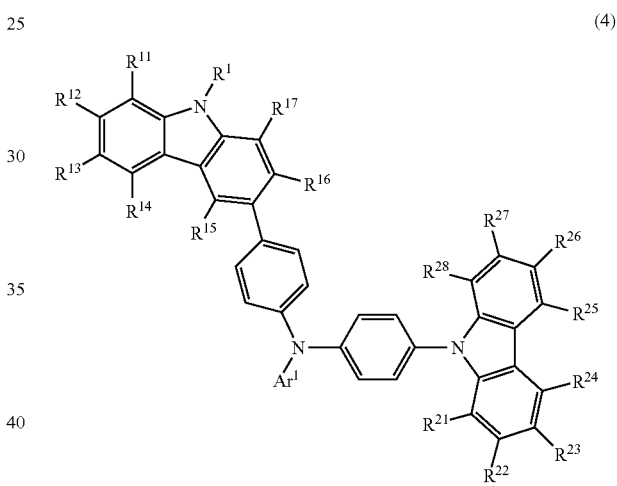

(4)

In the formula, $Ar^1$ represents a substituted or unsubstituted aryl group having 6 to 10 carbon atoms which form a ring; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

Another aspect of the present invention is a carbazole derivative represented by the general formula (5).

(5)

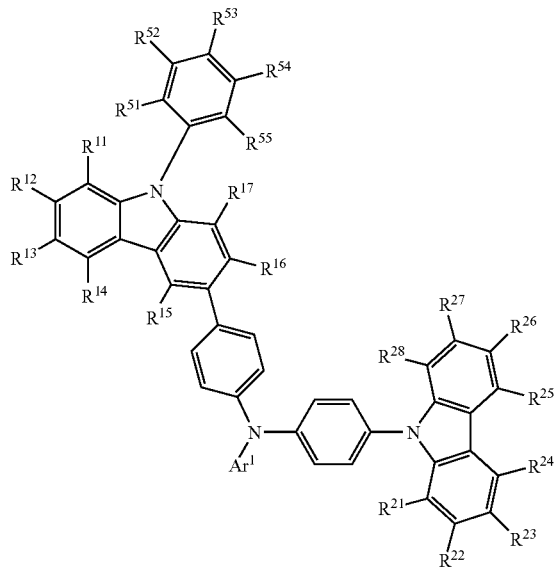

In the formula, $Ar^1$ represents a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; and $R^{51}$ to $R^{55}$ independently represent hydrogen, an alkyl group having 1 to 4 carbon atoms, or an aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

Another aspect of the present invention is a carbazole derivative represented by the general formula (6).

(6)

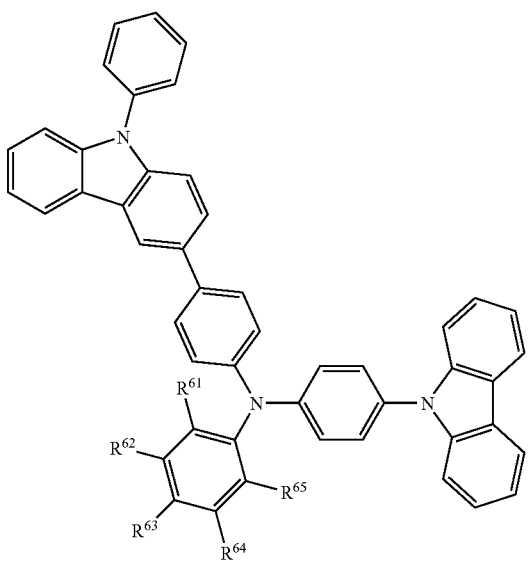

In the formula, $R^{61}$ to $R^{65}$ independently represent hydrogen, an alkyl group having 1 to 4 carbon atoms, or an aryl group having 6 to 10 carbon atoms which form a ring.

Another aspect of the present invention is a light-emitting element using any of the above carbazole derivatives. Specifically, the light-emitting element includes any of the above carbazole derivatives between a pair of electrodes.

Another aspect of the present invention is a light-emitting element including a light-emitting layer between a pair of electrodes, in which the light-emitting layer includes any of the above carbazole derivatives.

One embodiment of a light-emitting device of the present invention includes a light-emitting element in which a layer containing a light-emitting substance is included between a pair of electrodes and any of the above carbazole derivatives is included in the layer containing a light-emitting substance, and also includes a means for controlling light emission of the light-emitting element. Note that the light-emitting device in this specification includes an image display device, a light-emitting device, and a light source (including a lighting device). Further, the light-emitting device includes all of the following modules: modules in which a connector such as a flexible printed circuit (FPC), a tape automated bonding (TAB) tape, or a tape carrier package (TCP) is attached to a panel; modules having a TAB tape or a TCP provided with a printed wiring board at the end thereof; and modules having an integrated circuit (IC) directly mounted on a light-emitting element by a chip-on-glass (COG) method.

Further, an electronic device in which one embodiment of the light-emitting element of the present invention is used for a display portion is also included in the category of the present invention. Consequently, one embodiment of an electronic device of the present invention includes a display portion, in which the display portion is provided with the above light-emitting element and a means for controlling light emission of the light-emitting element.

Furthermore, a lighting device using one embodiment of the light-emitting device of the present invention is also included in the category of the present invention. Therefore, one embodiment of the lighting device of the present invention is provided with the above light-emitting device.

One embodiment of the carbazole derivative of the present invention is a material having a hole-transporting property.

One embodiment of the carbazole derivative of the present invention can be used as a hole-transporting layer of a light-emitting element.

Further, one embodiment of the carbazole derivative of the present invention can be used either as a light-emitting material (including a dopant material) or as a host material in a light-emitting layer of a light-emitting element.

In a light-emitting element using one embodiment of the carbazole derivative of the present invention, light emission from a light-emitting layer can be efficiently obtained.

Therefore, a light-emitting element, a light-emitting device, an electronic device, and a lighting device with reduced power consumption can be provided by using one embodiment of the carbazole derivative of the present invention.

BRIEF DESCRIPTION OF THE DRAWINGS

FIGS. 4A and 4B are views illustrating a light-emitting device.

DETAILED DESCRIPTION OF THE INVENTION

Figure 1A:
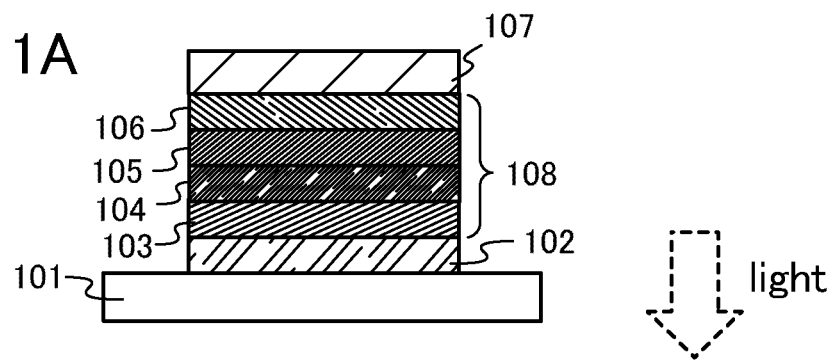
FIGS. 1A to 1C are views each illustrating a light-emitting element.

Hereinafter, embodiments and examples of the present invention will be described with reference to the drawings. Note that the present invention is not limited to the following description, and it will be easily understood by those skilled in the art that various changes and modifications can be made without departing from the spirit and scope of the present invention. Therefore, the present invention should not be construed as being limited to the description in the following embodiments and examples.

[Embodiment 1]

In this embodiment, one embodiment of a carbazole derivative of the present invention will be described.

A carbazole derivative according to this embodiment is represented by the general formula (1).

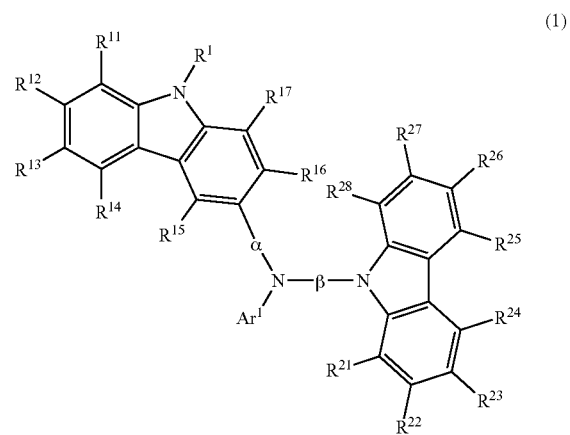

(1)

In the formula, $Ar^1$ represents a substituted or unsubstituted aryl group having 6 to 10 carbon atoms which form a ring; $\alpha$ and $\beta$ independently represent a substituted or unsubstituted arylene group having 6 to 12 carbon atoms which form a ring; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

A carbazole derivative according to this embodiment is represented by the general formula (2).

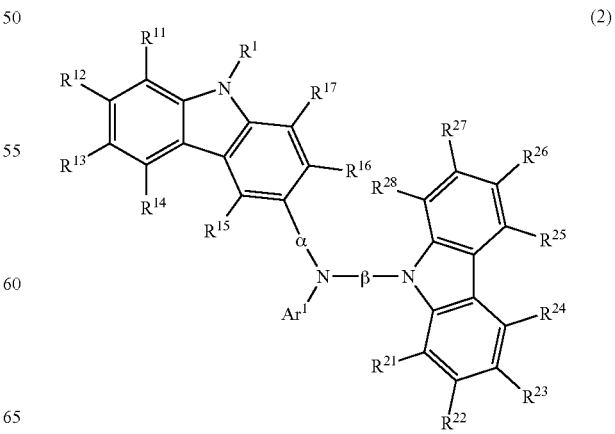

(2)

In the formula, $Ar^1$ represents a substituted or unsubstituted aryl group having 6 to 10 carbon atoms which form a ring; α and β independently represent a substituted or unsubstituted phenylene group; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or a substituted or unsubstituted aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

A carbazole derivative according to this embodiment is represented by the general formula (3).

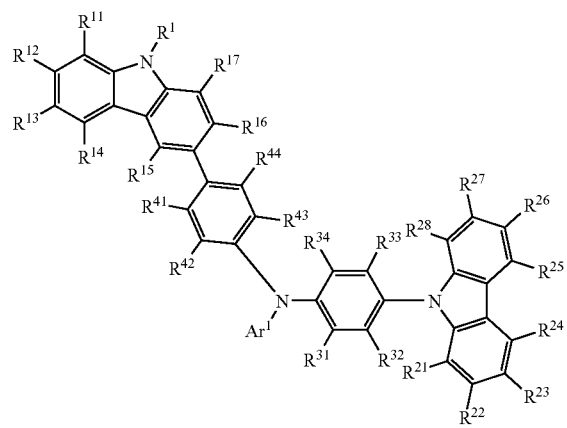

(3)

In the formula, $Ar^1$ represents a substituted or unsubstituted aryl group having 6 to 10 carbon atoms which form a ring; $R^1$ represents an alkyl group having 1 to 4 carbon atoms or a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; and $R^{31}$ to $R^{34}$ and $R^{41}$ to $R^{44}$ independently represent hydrogen or an alkyl group having 1 to 4 carbon atoms. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

A carbazole derivative according to this embodiment is represented by the general formula (4).

(4)

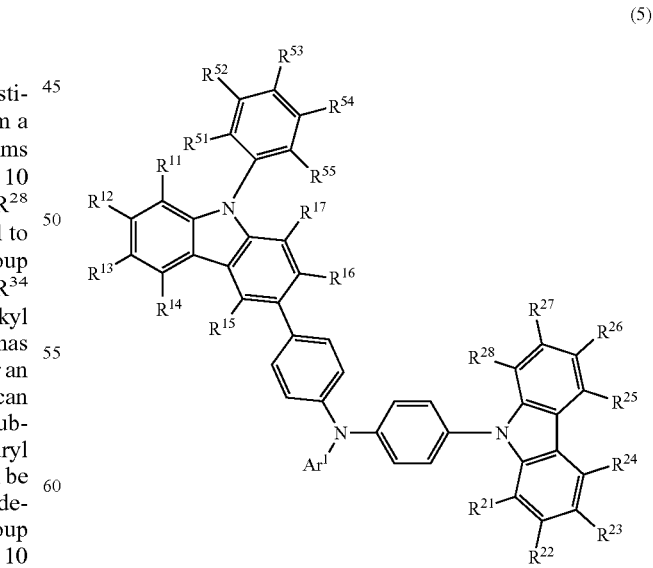

In the formula, $Ar^1$ represents a substituted or unsubstituted aryl group having 6 to 10 carbon atoms which form a ring; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. In the case where $R^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

A carbazole derivative according to this embodiment is represented by the general formula (5).

(5)

In the formula, $Ar^1$ represents a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; and $R^{51}$ to $R^{55}$ independently represent hydrogen, an alkyl group having 1 to 4 carbon atoms, or an aryl group having 6 to 10 carbon atoms which form a ring. In the case where $Ar^1$ has a substituent, an alkyl group having 1 to 4 carbon atoms or an aryl group having 6 to 10 carbon atoms which form a ring can be given as the substituent. $R^{11}$ to $R^{17}$ and $R^{21}$ to $R^{28}$ may independently have a substituent, and in that case, an alkyl group having 1 to 4 carbon atoms or an aryl group having 6 to 10 carbon atoms which form a ring can be given as the substituent.

A carbazole derivative according to this embodiment is represented by the general formula (6).

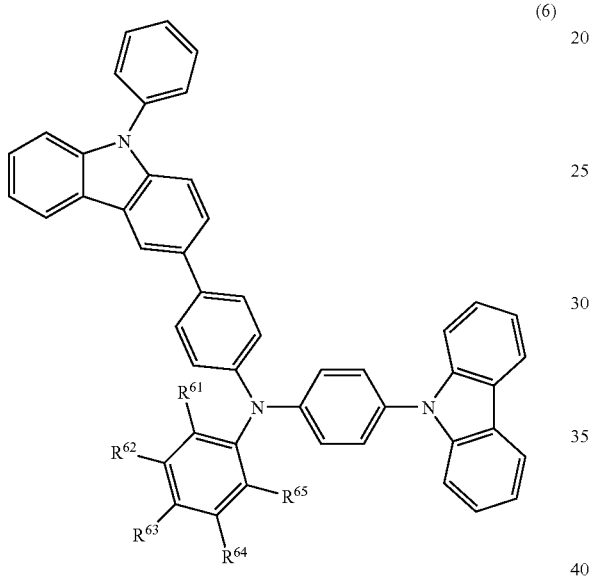

(6)

In the formula, $R^{61}$ to $R^{65}$ independently represent hydrogen, an alkyl group having 1 to 4 carbon atoms, or an aryl group having 6 to 10 carbon atoms which form a ring.

Note that the number of carbon atoms of the aryl group or the arylene group described in this specification represents the number of carbon atoms which form a ring of the main skeleton, and do not include the number of carbon atoms of a substituent bonded to the carbon atoms which form the ring of the main skeleton of the aryl group or the arylene group. An alkyl group having 1 to 4 carbon atoms or an aryl group having 6 to 10 carbon atoms can be given as the substituent bonded to the aryl group. Specifically, a methyl group, an ethyl group, a propyl group, a butyl group, a phenyl group, a naphthyl group, or the like can be given. An alkyl group having 1 to 4 carbon atoms can be given as the substituent bonded to the arylene group. Specifically, a methyl group, an ethyl group, a propyl group, a butyl group, or the like can be used. Note that the aryl group or the arylene group may have one substituent or more substituents.

In the general formulae (1) to (5), as specific examples of groups represented by $Ar^1$, substituents represented by the structural formulae (11-1) to (11-21) can be given, for example.

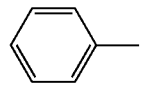
(11-1)

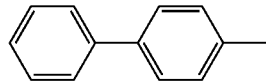
(11-2)

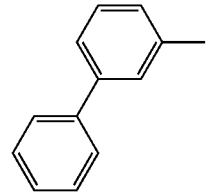
(11-3)

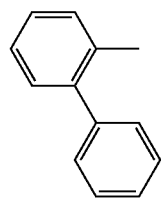
(11-4)

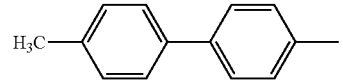
(11-5)

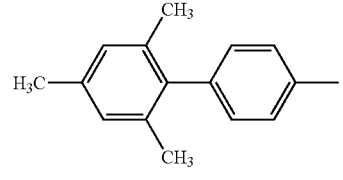
(11-6)

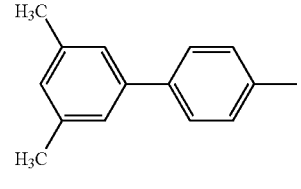
(11-7)

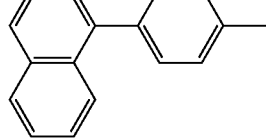
(11-8)

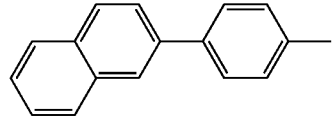
(11-9)

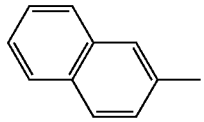
(11-10)

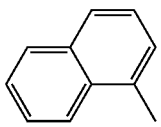
(11-11)

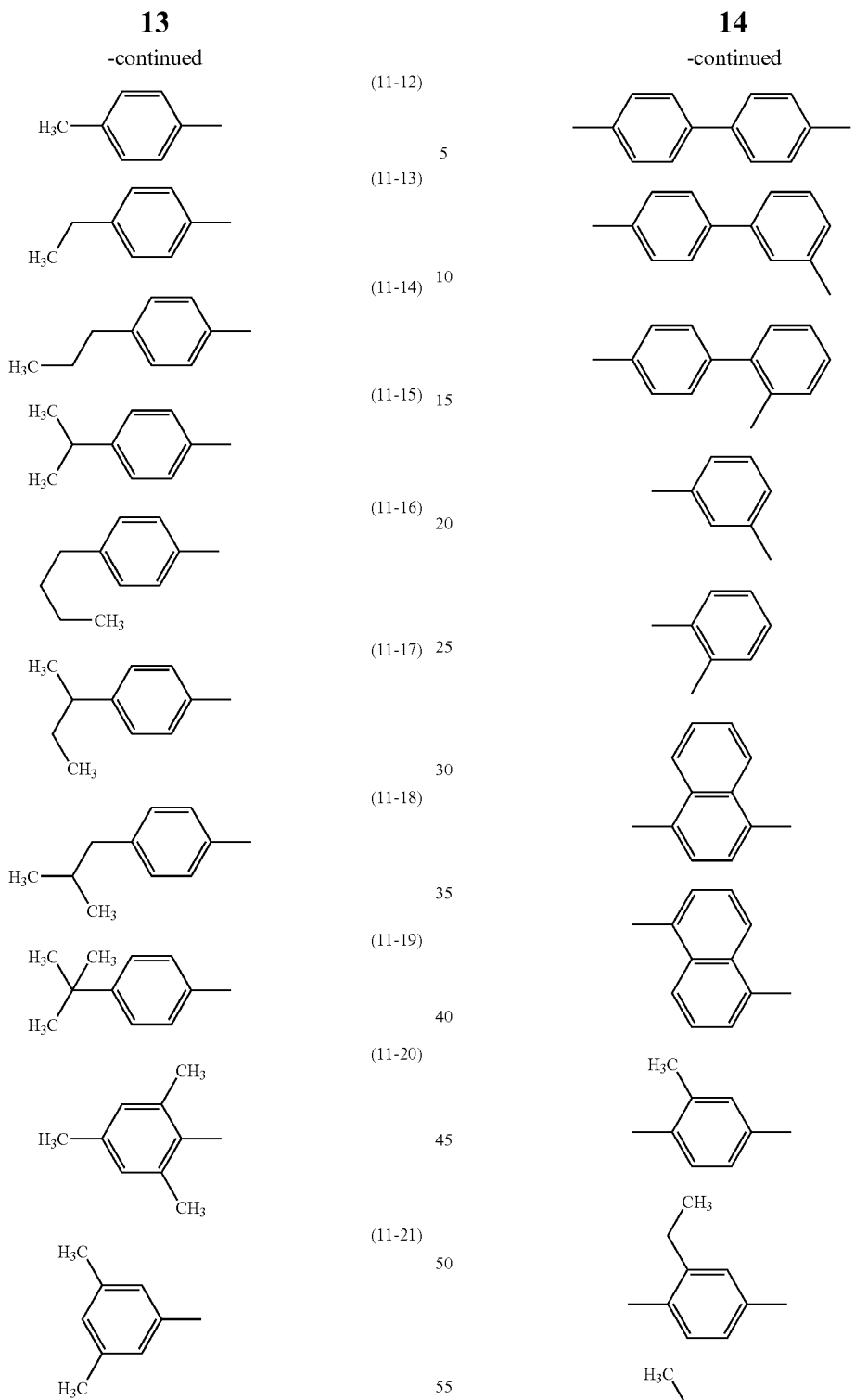
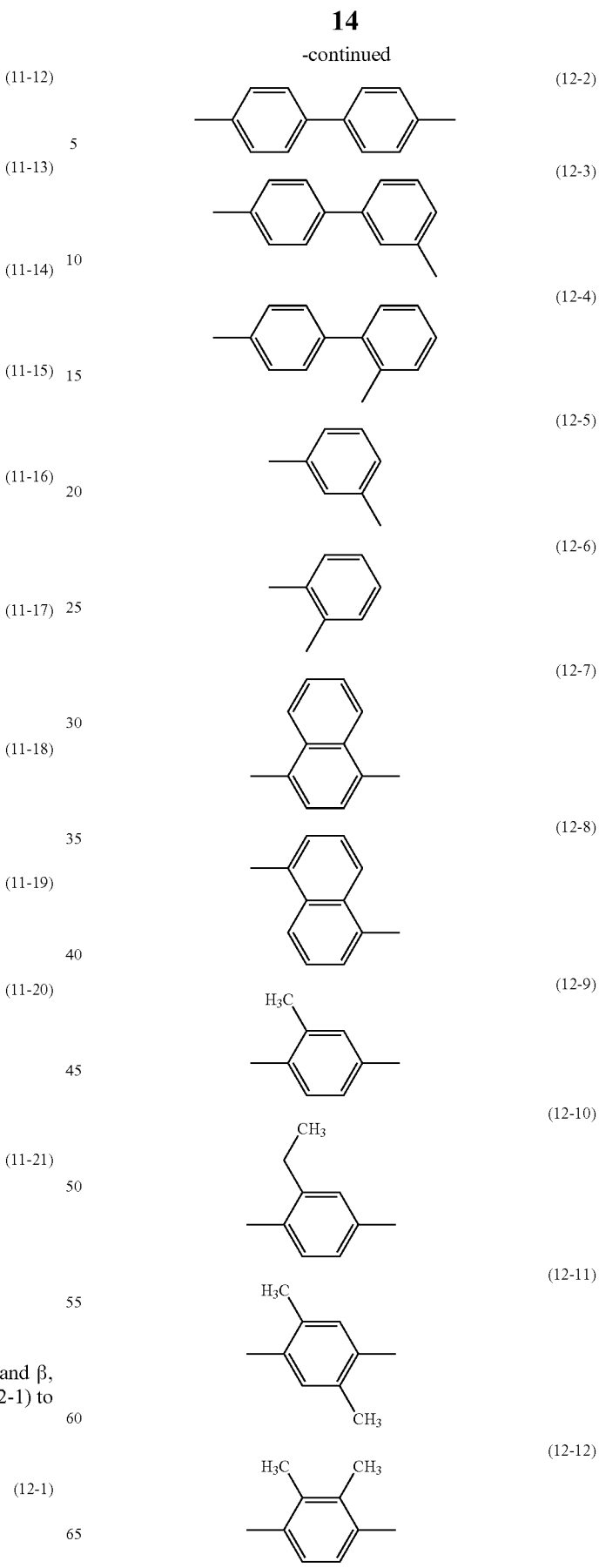
As specific examples of groups represented by α and β, substituents represented by the structural formulae (12-1) to (12-21) can be given, for example.

(12-13) 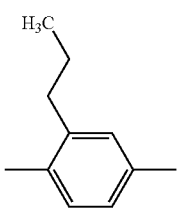
(12-14) 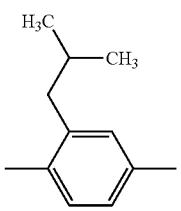
(12-15) 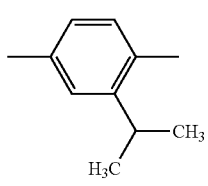
(12-16) 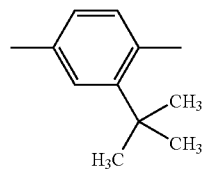
(12-17) 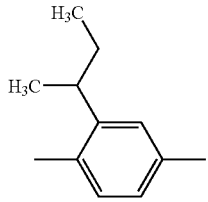
(12-18) 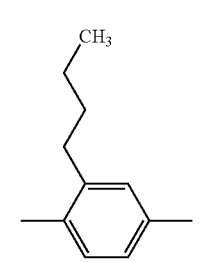
(12-19) 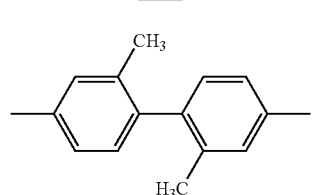
(12-20) 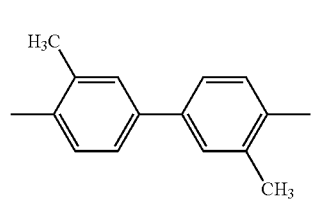
(12-21) 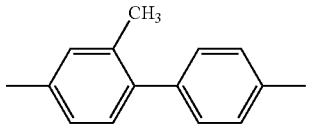
As specific examples of groups represented by $R^1$, substituents represented by the structural formulae (13-1) to (13-29) can be given, for example.
(13-1) 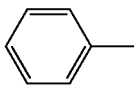
(13-2) 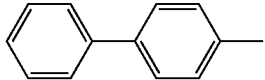
(13-3) 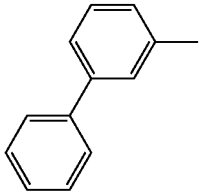
(13-4) 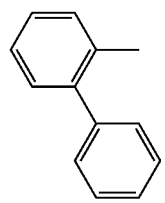
(13-5) 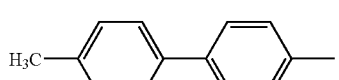
(13-6) 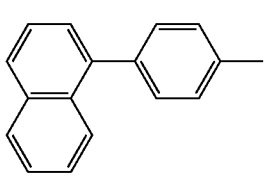
(13-7) 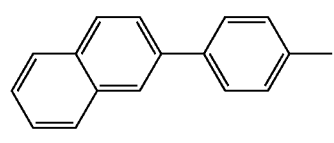
(13-8) 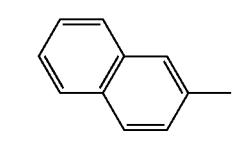
(13-9) 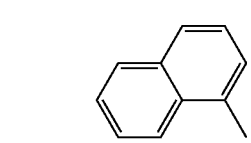

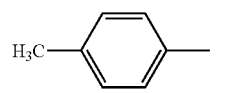 (13-10)
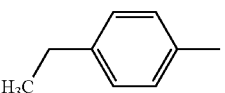 (13-11)
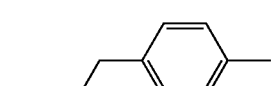 (13-12)
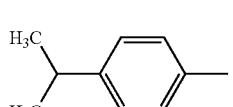 (13-13)
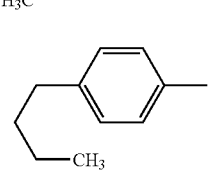 (13-14)
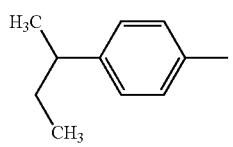 (13-15)
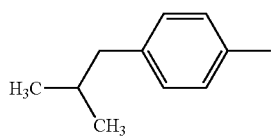 (13-16)
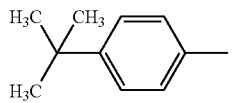 (13-17)
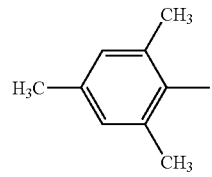 (13-18)
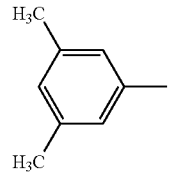 (13-19)
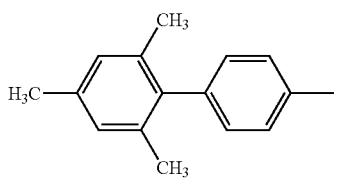 (13-20)
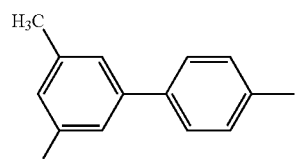 (13-21)
—CH$_3$ (13-22)
—CH$_2$—CH$_3$ (13-23)
$\begin{array}{c}H_2C—\\H_3C—CH_2\end{array}$ (13-24)
$\begin{array}{c}H_3C\\\phantom{H}CH—\\H_3C\end{array}$ (13-25)
(13-26)
(13-27)
(13-28)
(13-29)
As specific examples of groups represented by $R^{11}$ to $R^{17}$ and $R^{21}$ to $R^{28}$, substituents represented by the structural formulae (14-1) to (14-30) can be given, for example.
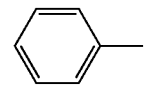 (14-1)
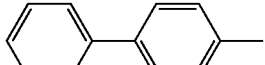 (14-2)
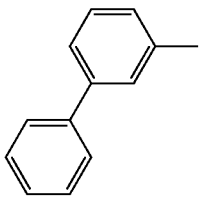 (14-3)

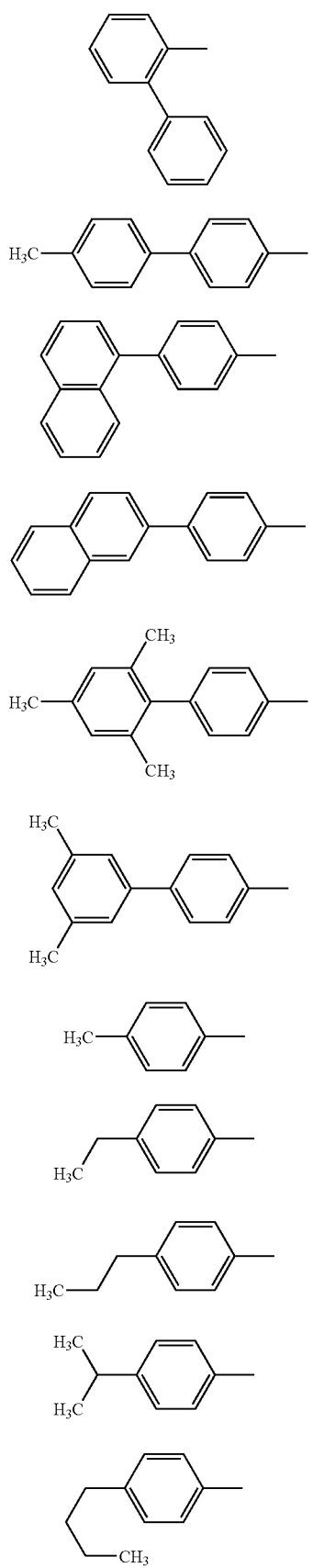
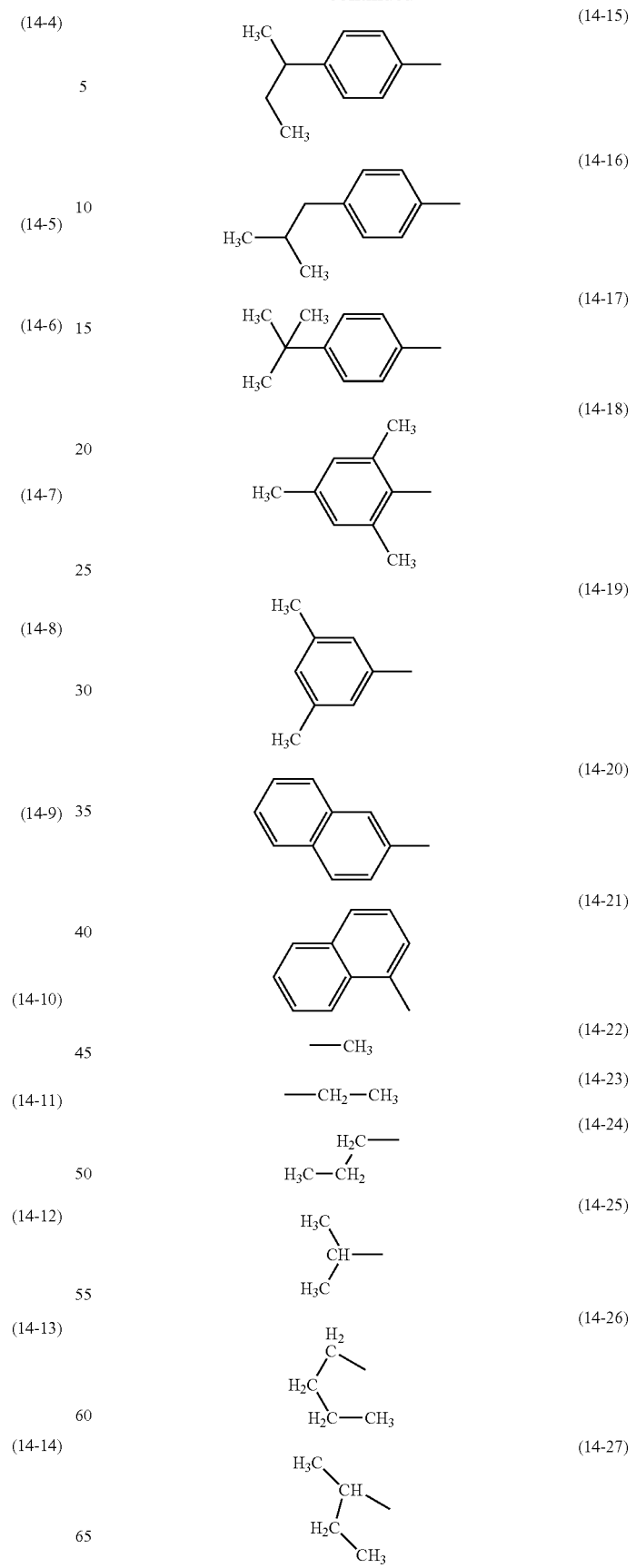

-continued

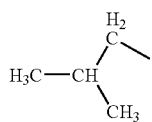 (14-28)

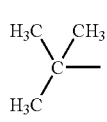 (14-29)

—H (14-30)

As specific examples of groups represented by $R^{51}$ to $R^{55}$, substituents represented by the structural formulae (15-1) to (15-22) can be given, for example.

H— (15-1)

H₃C— (15-2)

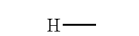 (15-3)

 (15-4)

 (15-5)

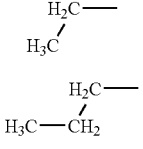 (15-6)

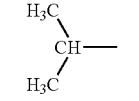 (15-7)

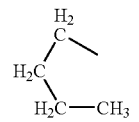 (15-8)

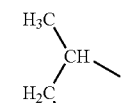 (15-9)

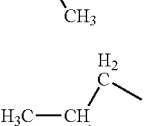 (15-10)

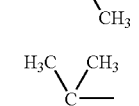 (15-11)

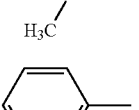 (15-12)

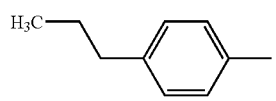 (15-13)

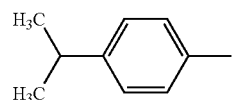 (15-14)

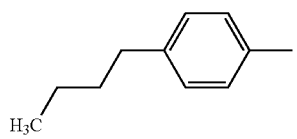 (15-15)

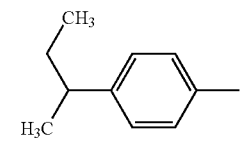 (15-16)

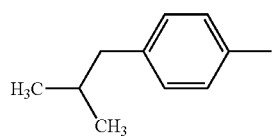 (15-17)

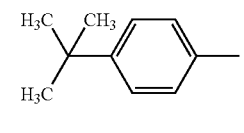 (15-18)

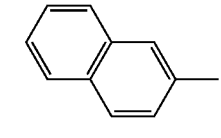 (15-19)

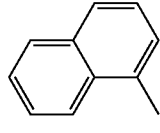 (15-20)

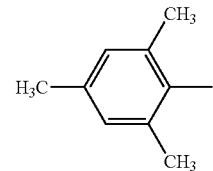 (15-21)

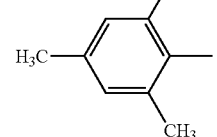 (15-22)

As specific examples of the carbazole derivatives represented by the general formulae (1) to (6), carbazole derivatives represented by the structural formulae (100) to (178) can be given, for example. However, the present invention is not limited thereto.

(100)
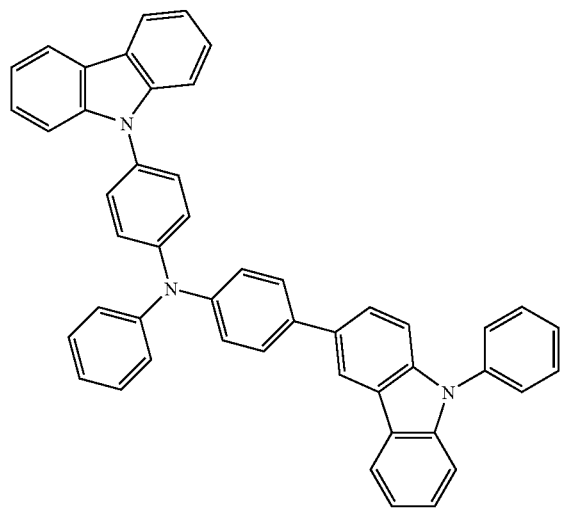
(101)
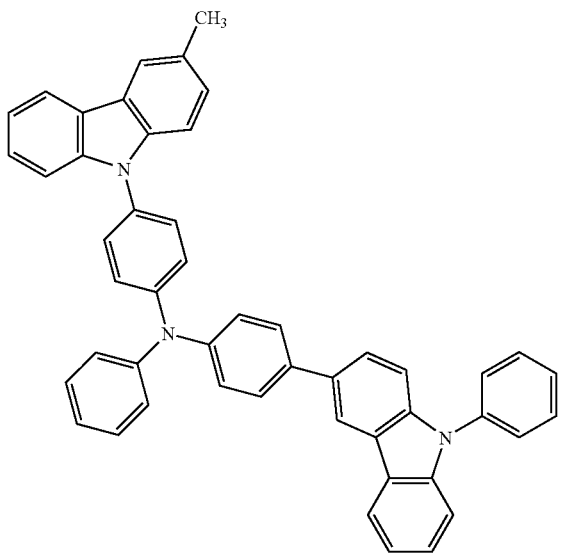
(102)
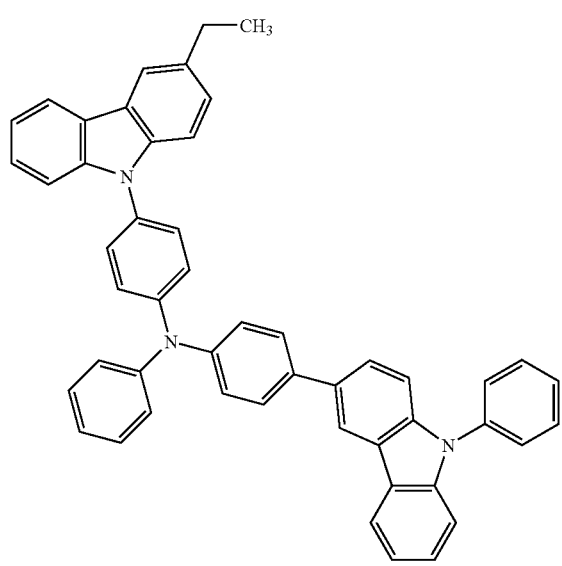
(103)
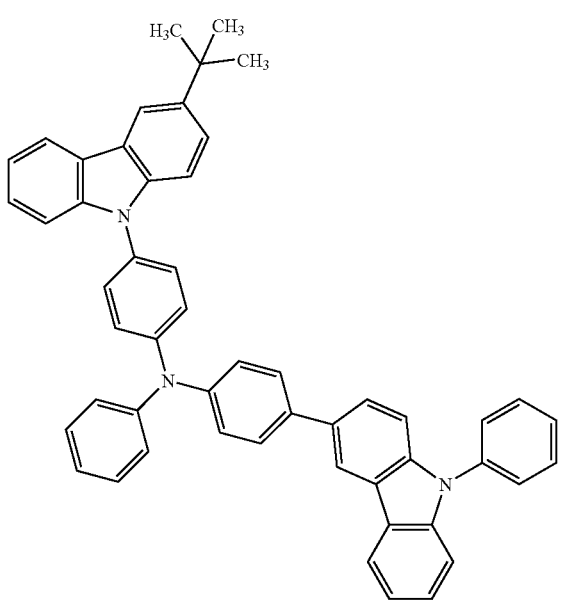

(104)
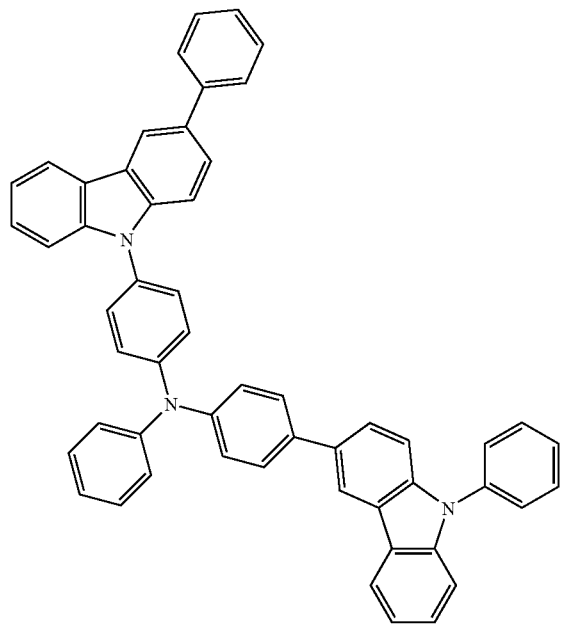
(105)
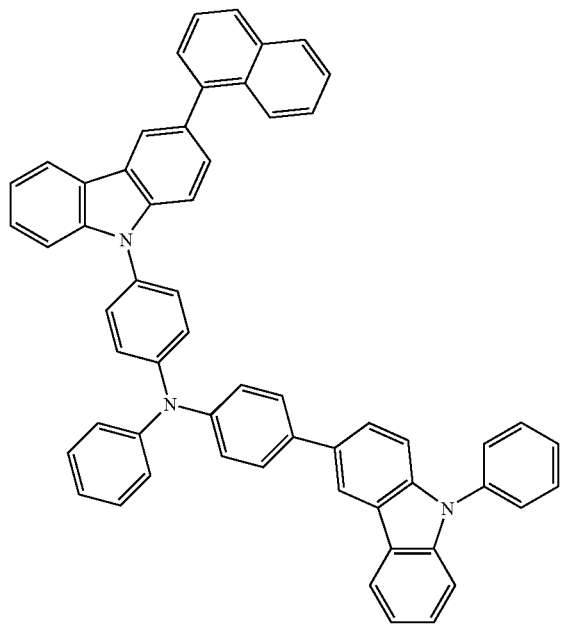
(106)
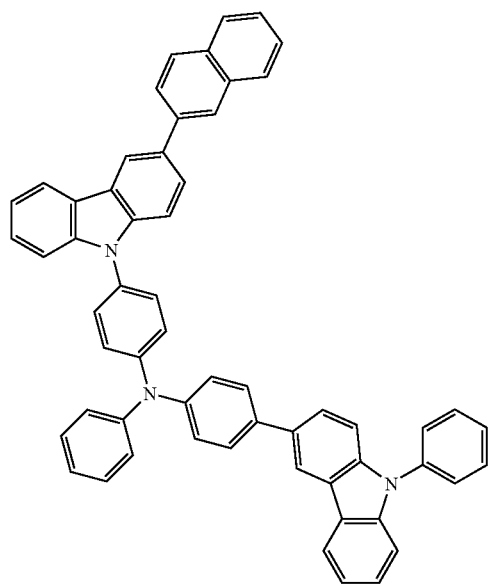
(107)
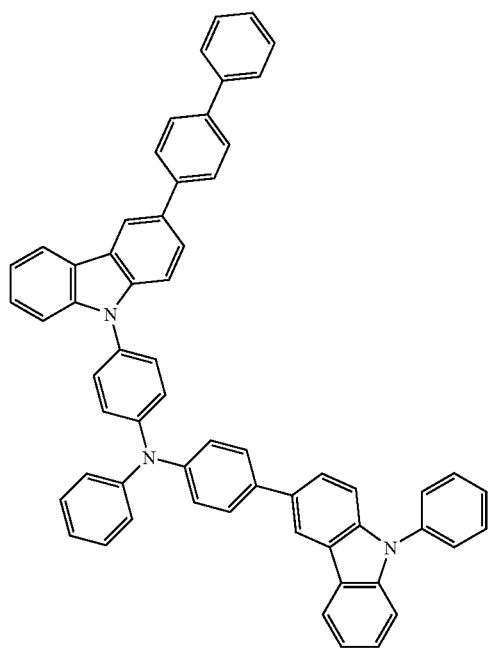

(108)
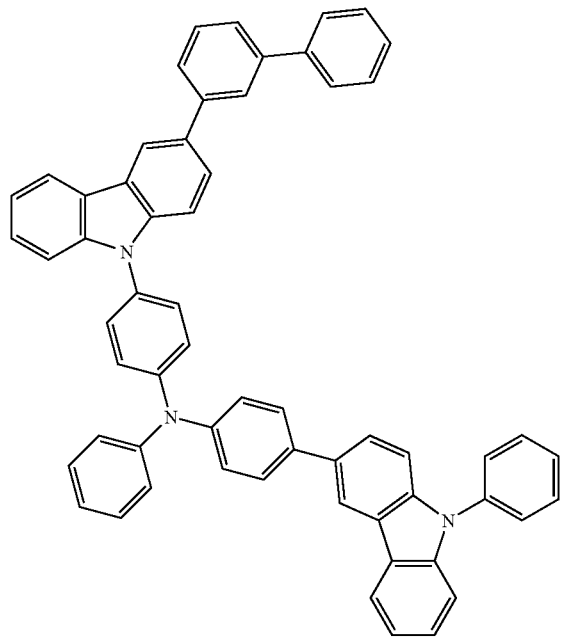
(109)
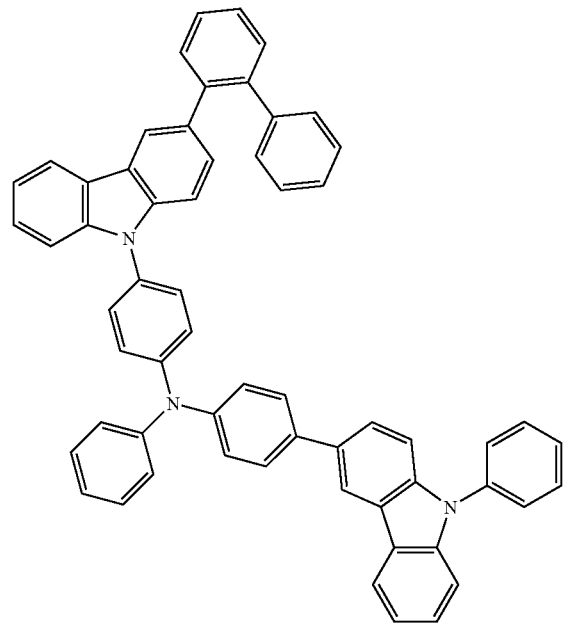
(110)
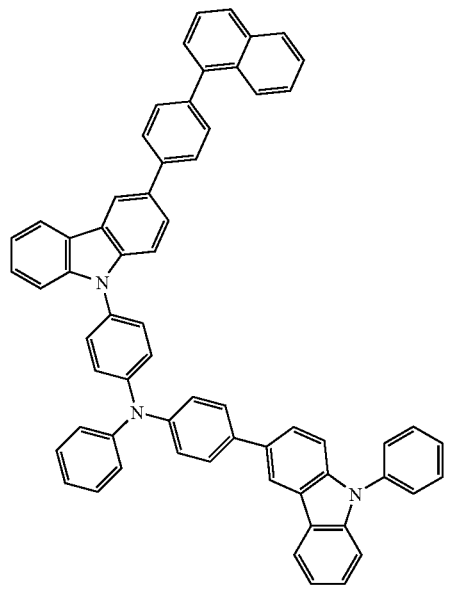
(111)
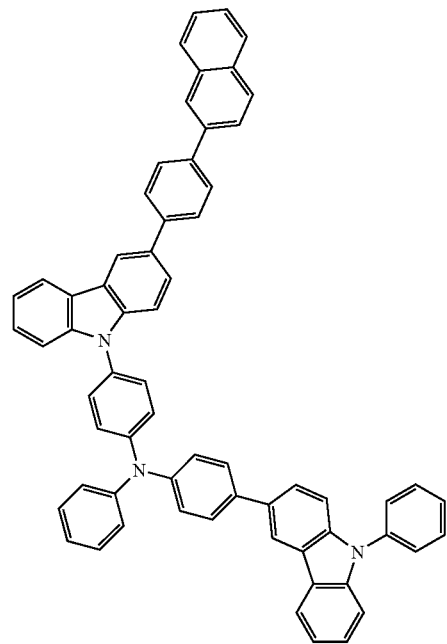

-continued
(112)
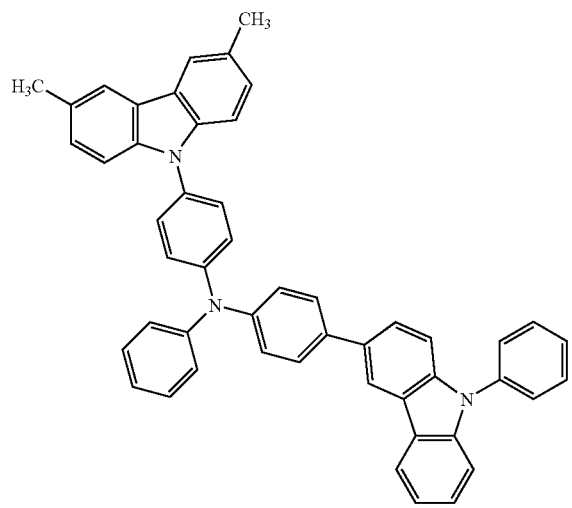
(113)
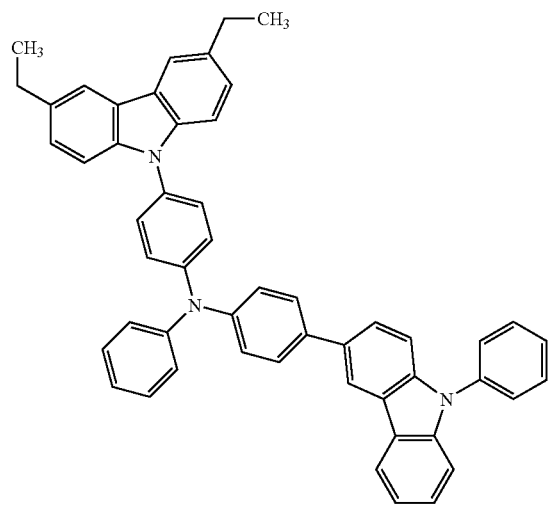
(114)
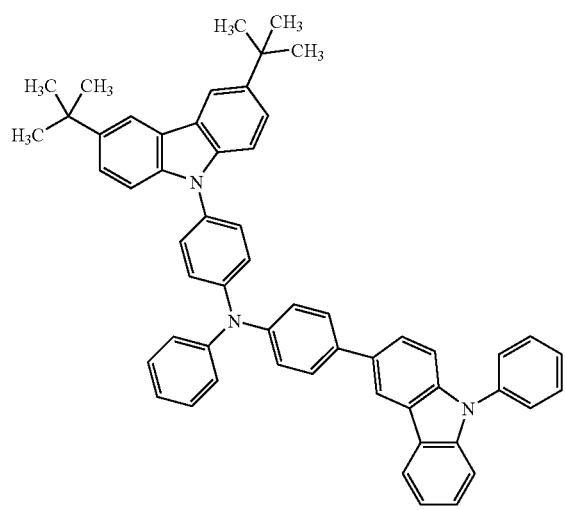
(115)
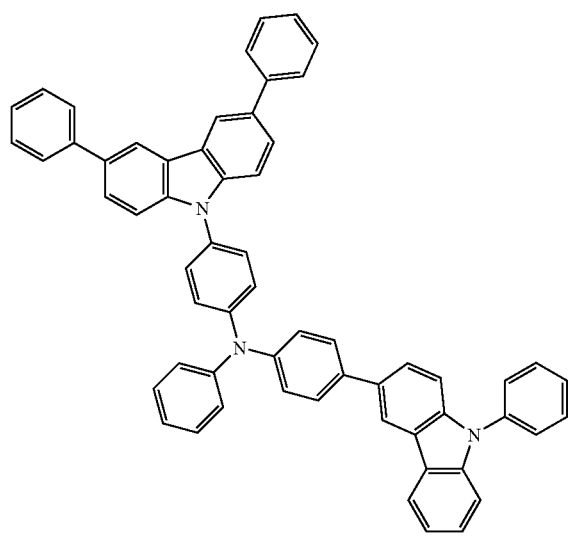
(116)
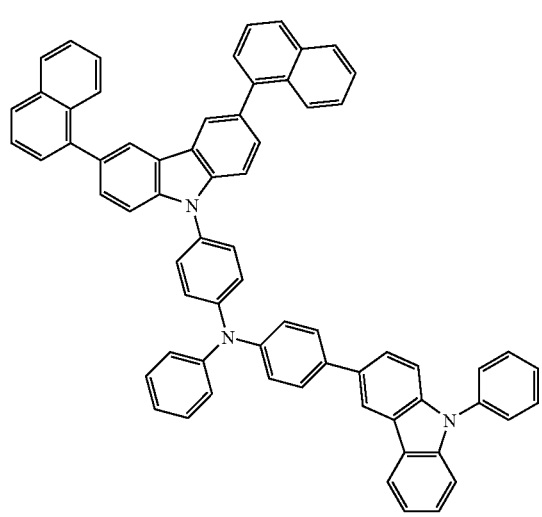
(117)
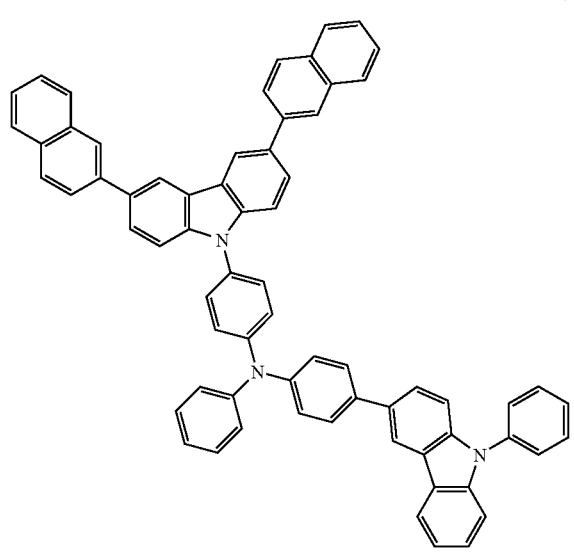

(118)
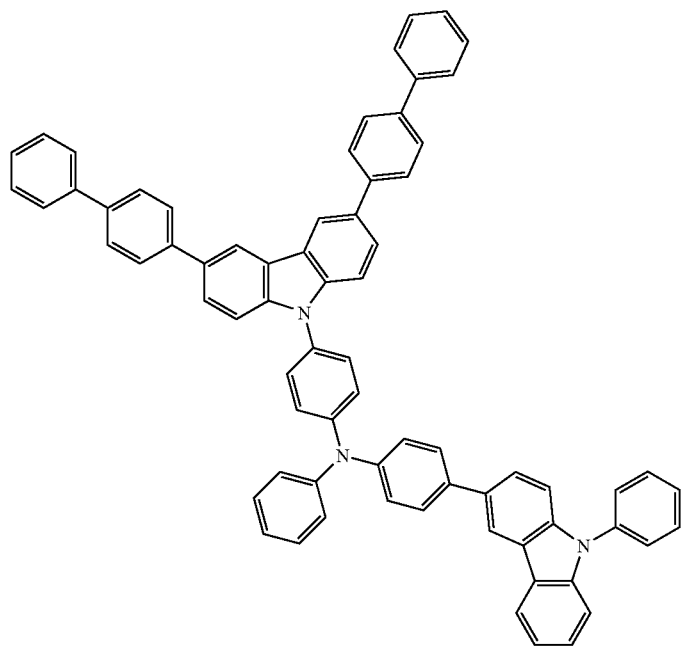
(119)
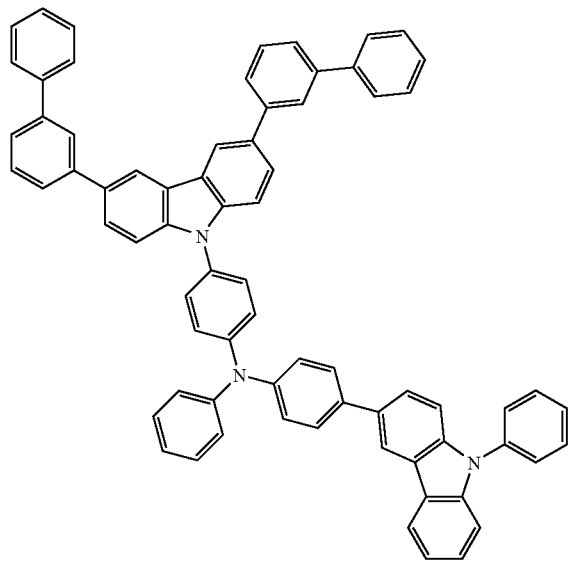
(120)
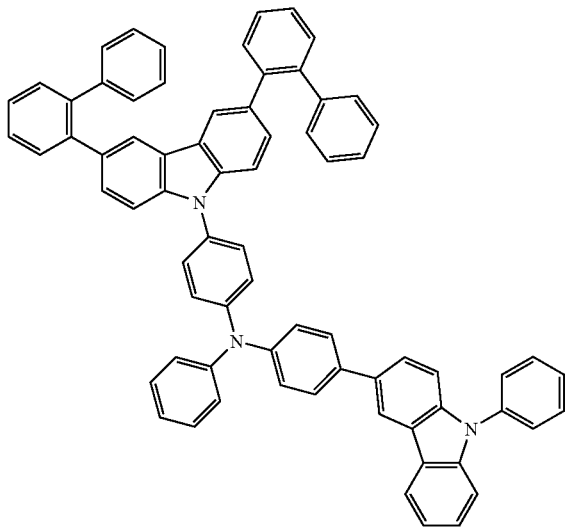

(121)
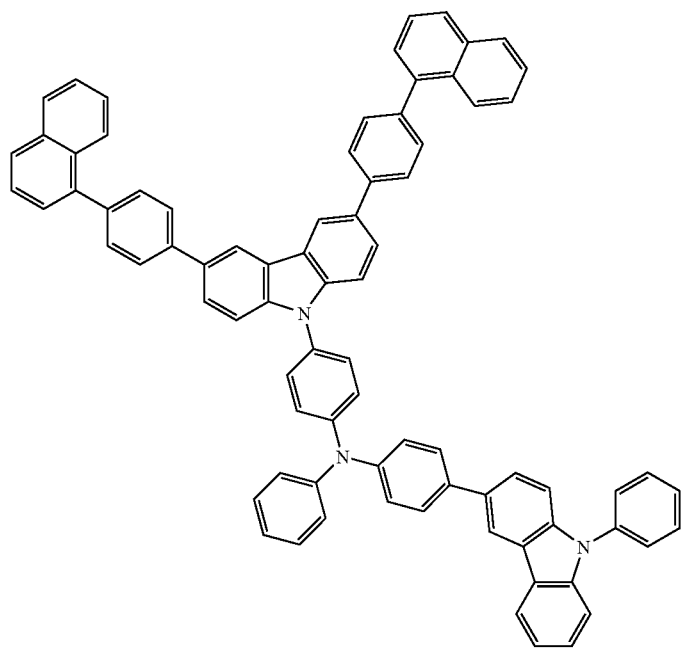
(122)
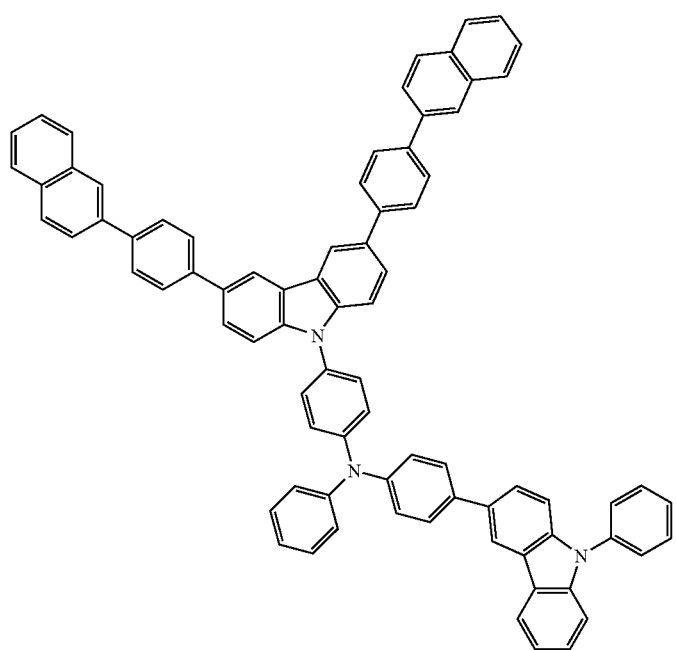

(123)
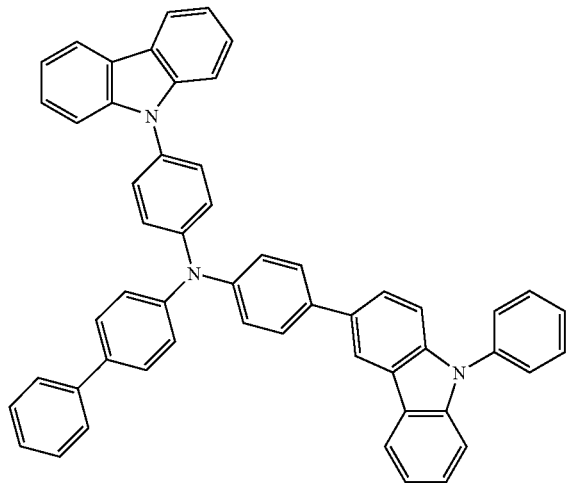
(124)
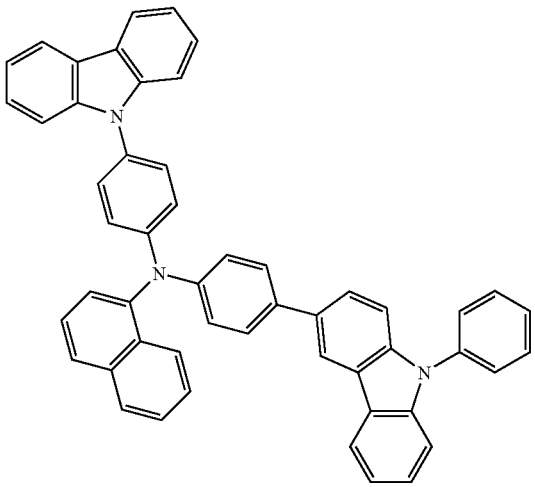
(125)
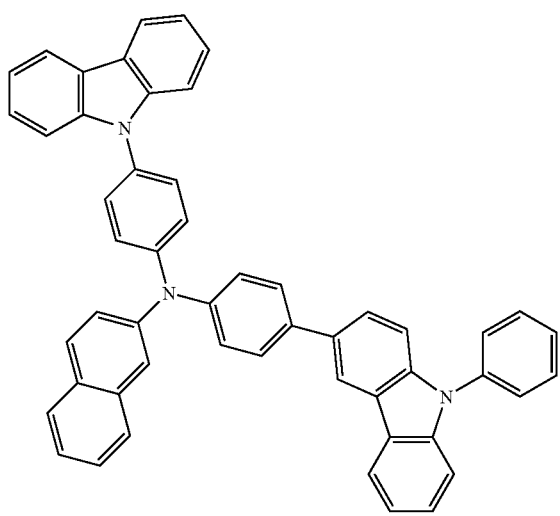
(126)
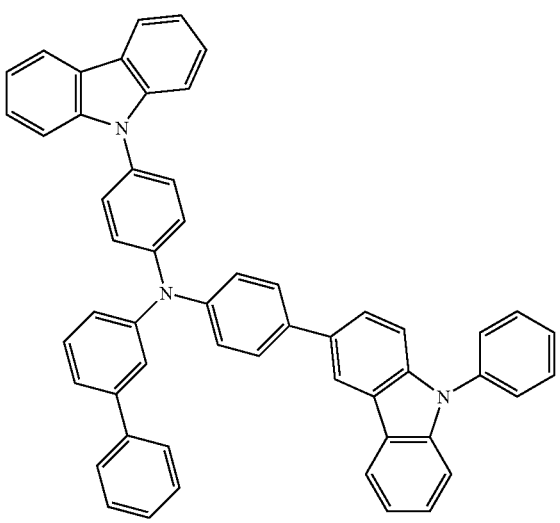
(127)
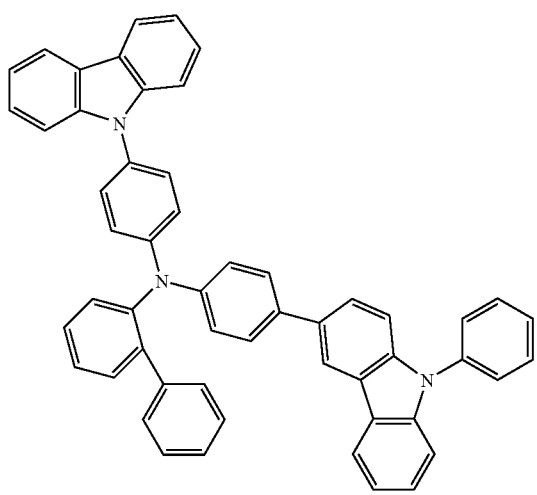
(128)
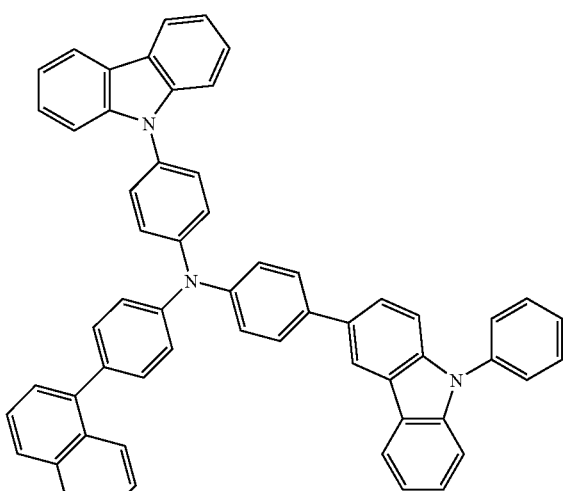

-continued
(129)
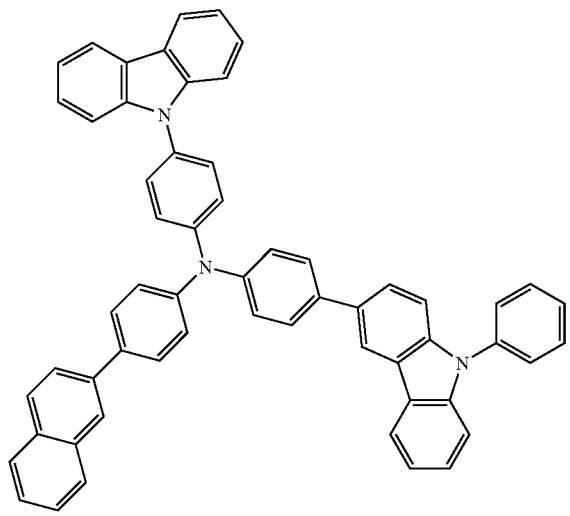
(130)
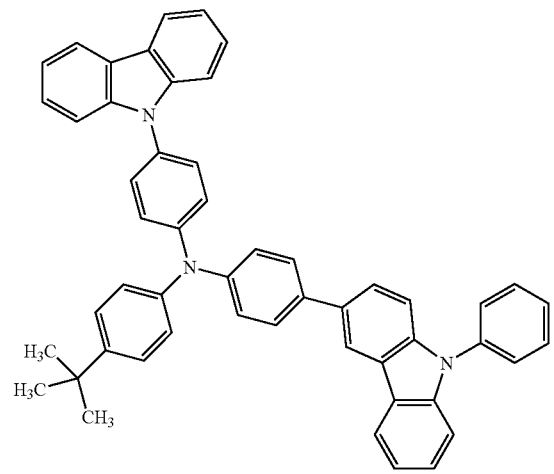
(131)
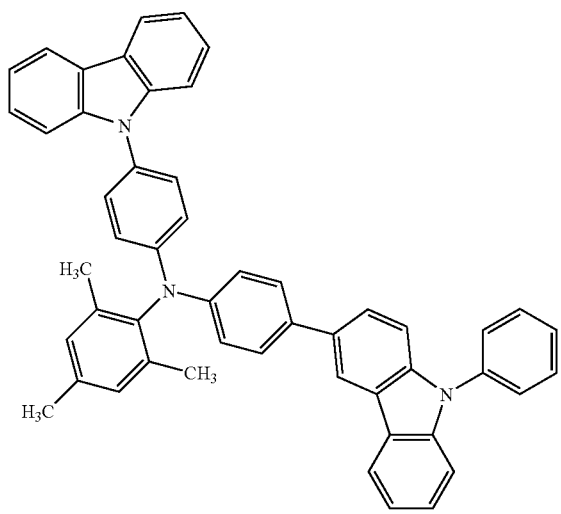
(132)
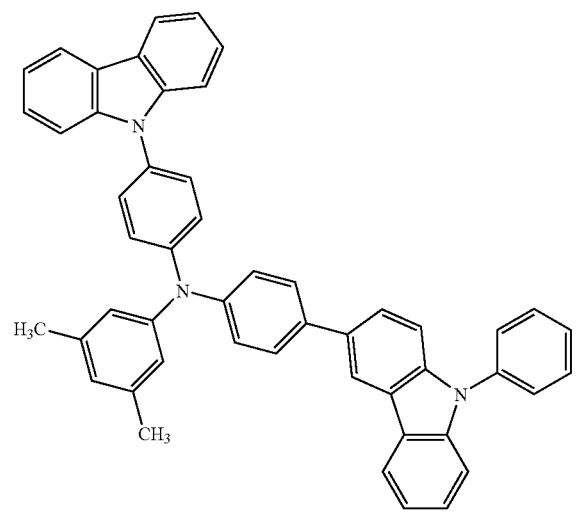
(133)
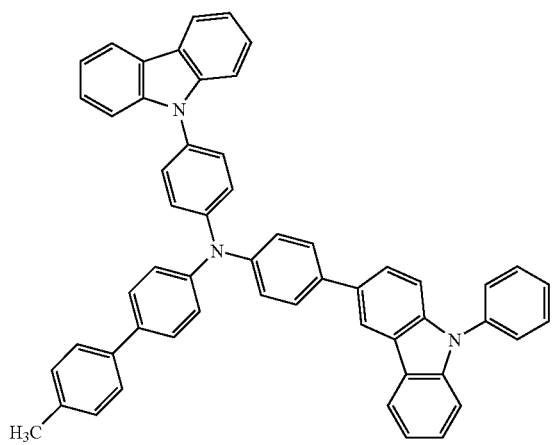
(134)
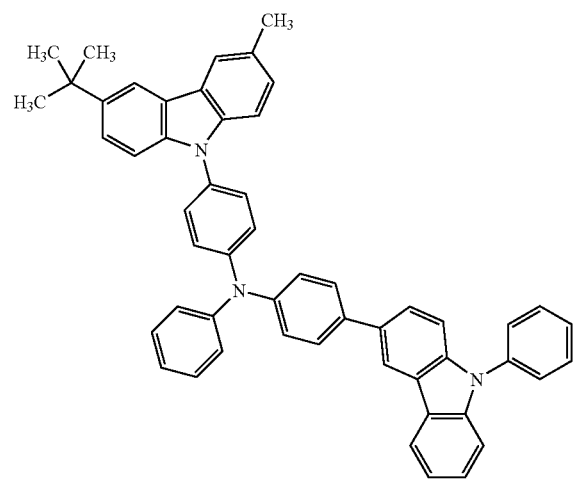

-continued
(135)
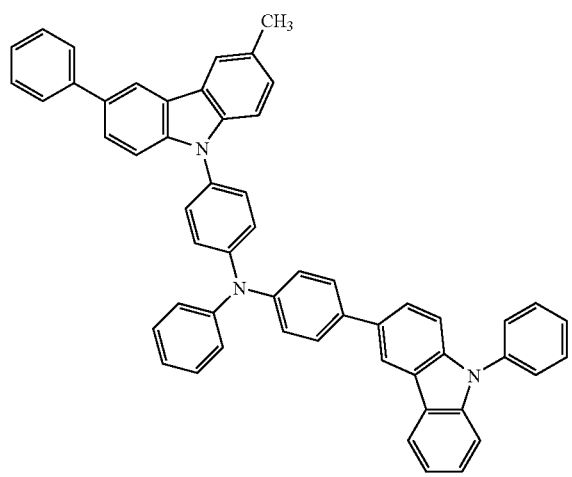
(136)
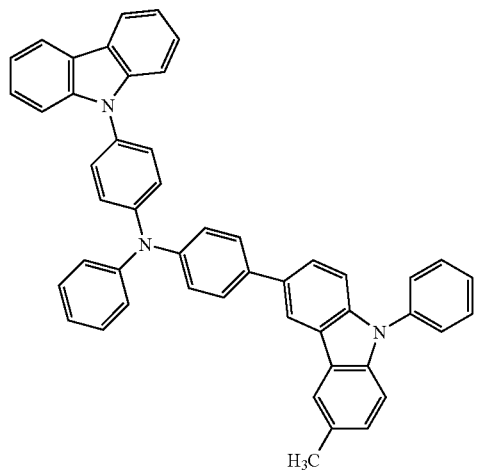
(137)
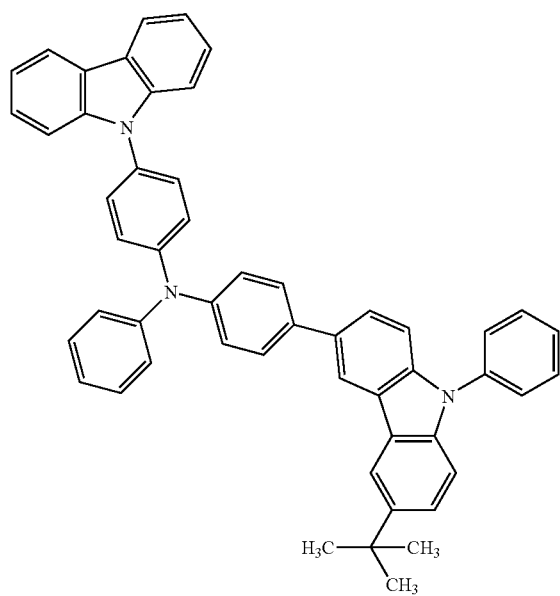
(138)
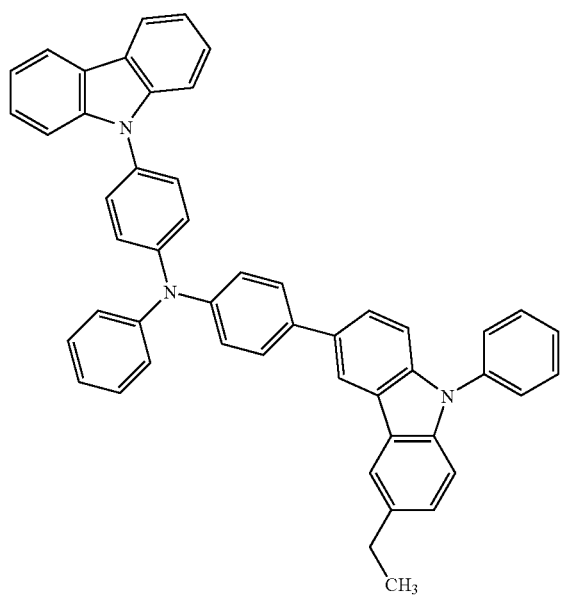

-continued
(139)
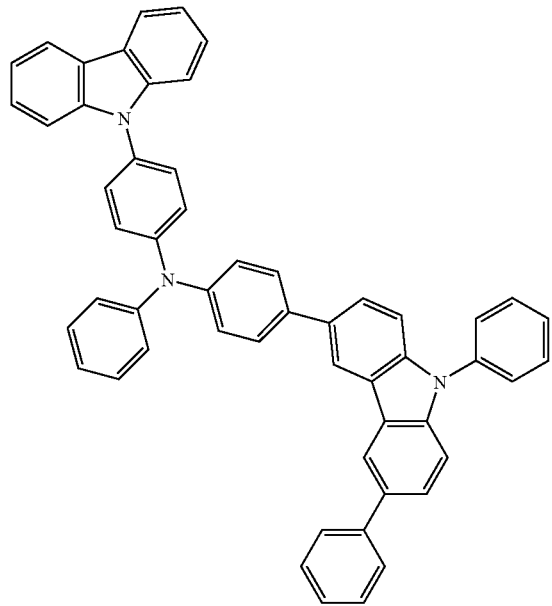
(140)
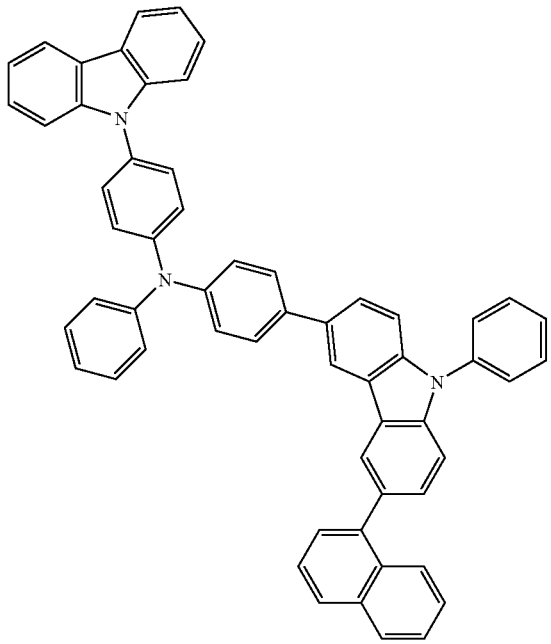
(141)
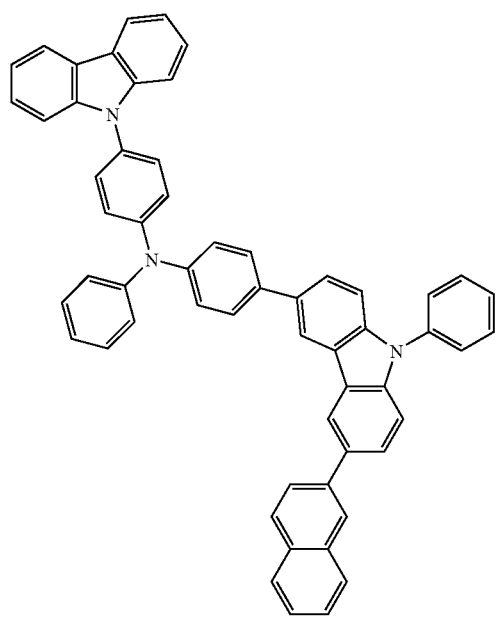
(142)
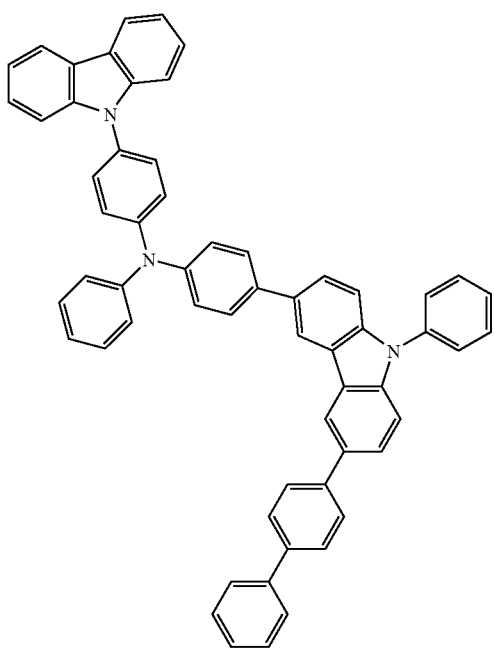

-continued
(143)
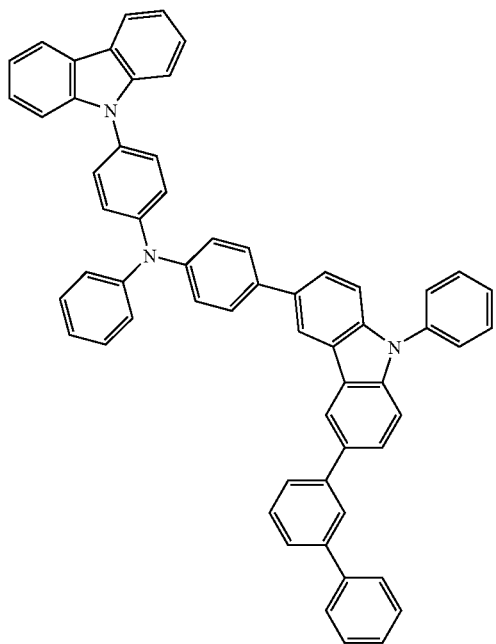
(144)
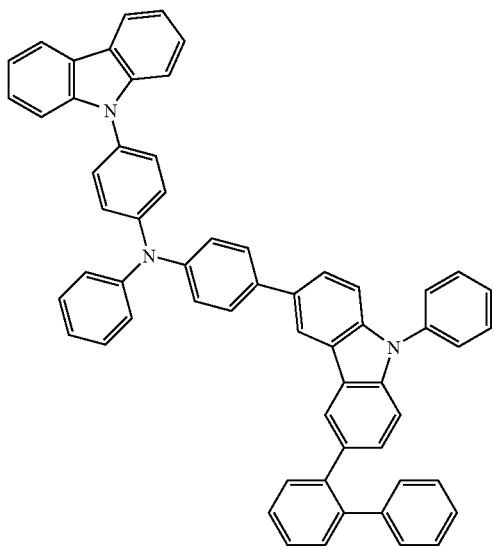
(145)
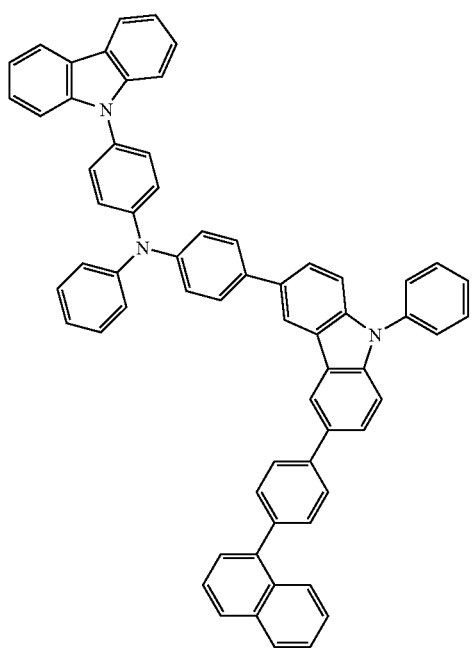
(146)
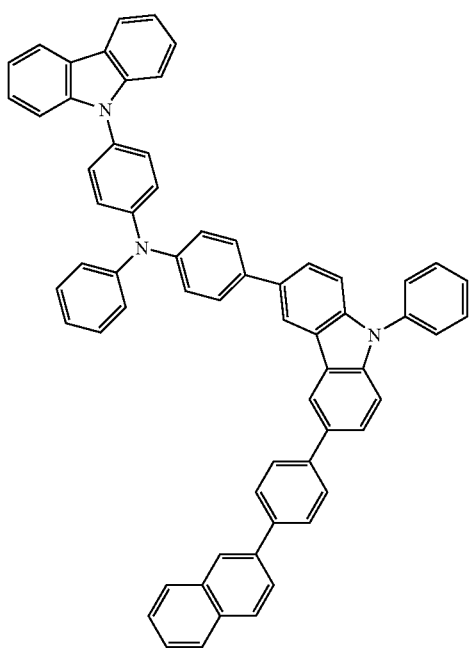

-continued
(147)
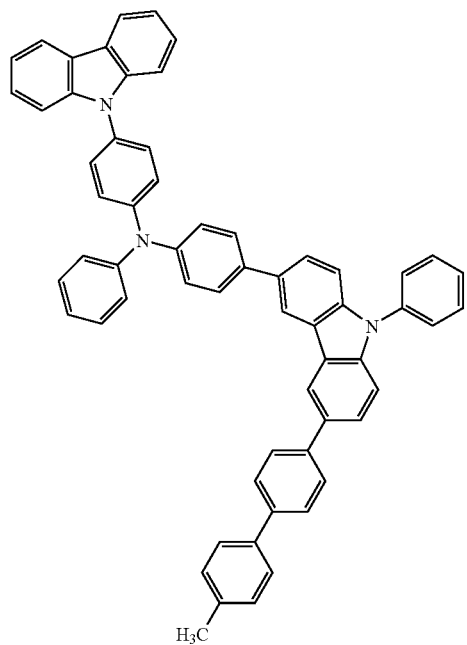
(148)
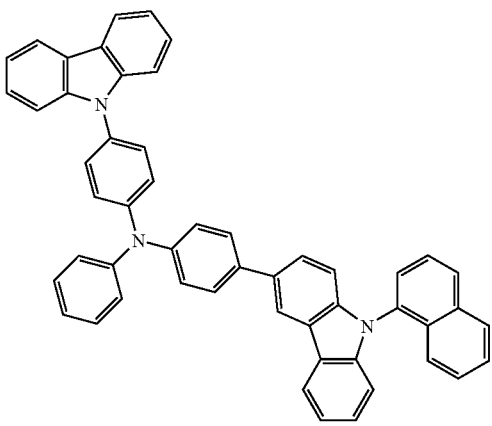
(149)
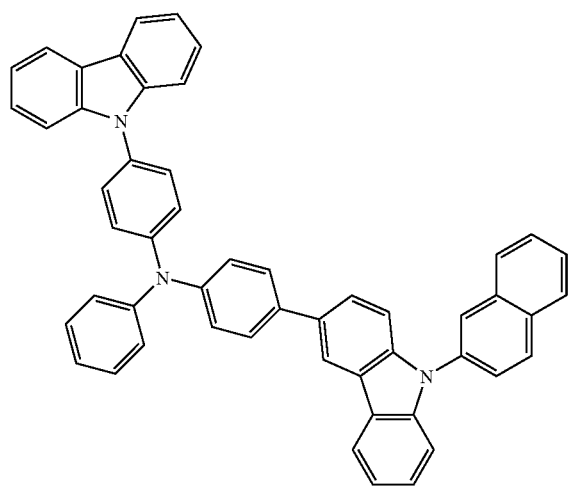
(150)
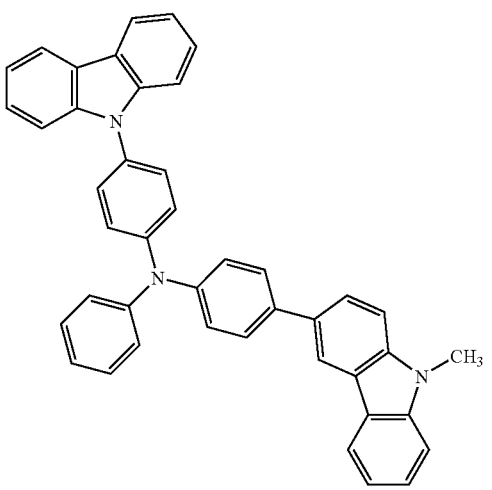
(151)
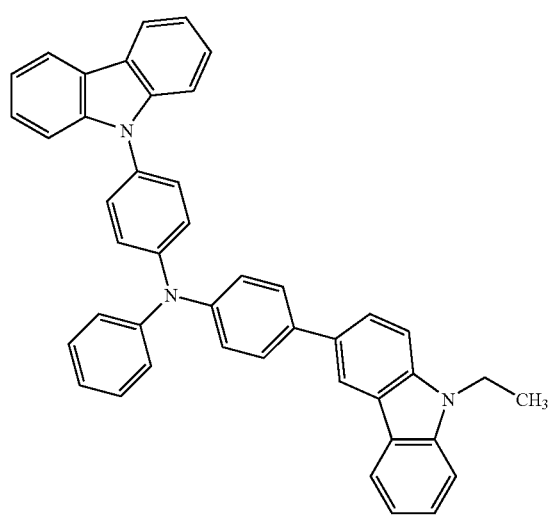
(152)
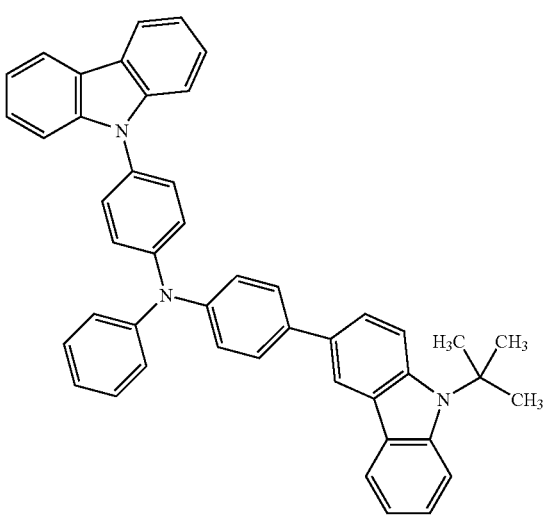

(153)
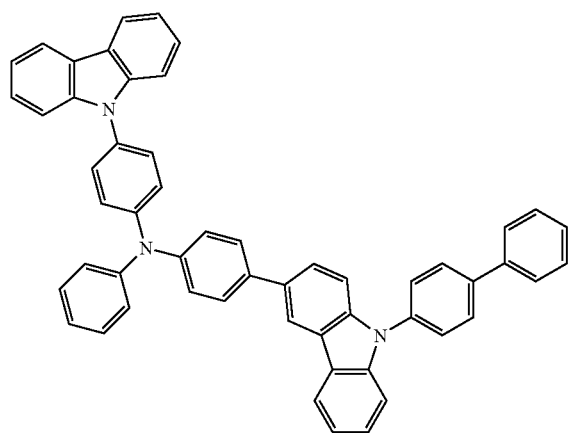
(154)
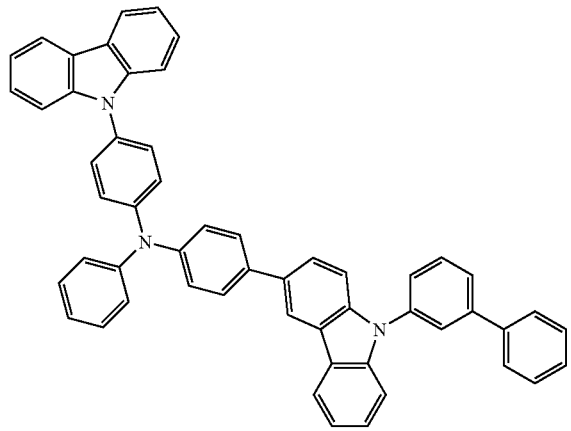
(155)
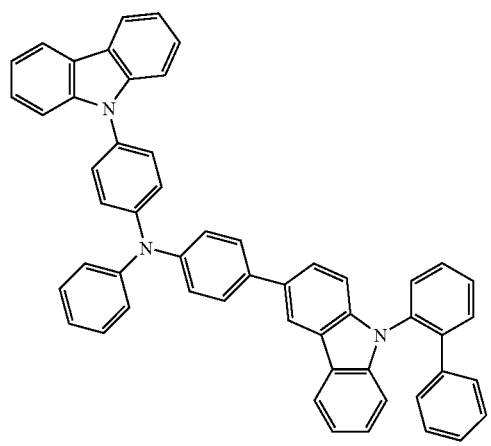
(156)
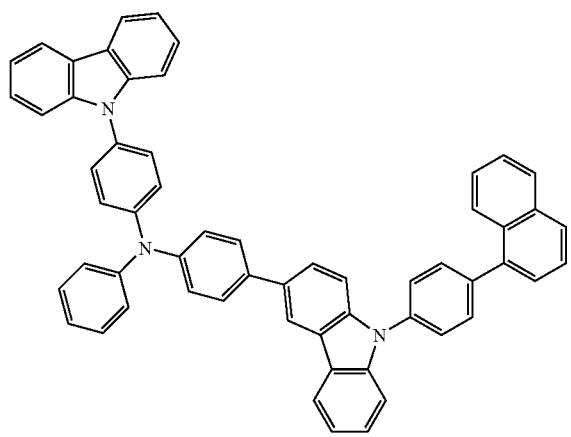
(157)
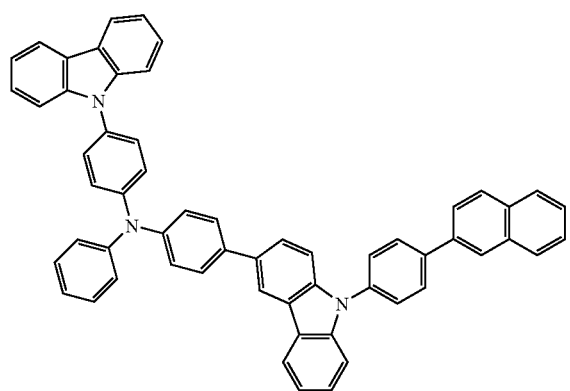
(158)
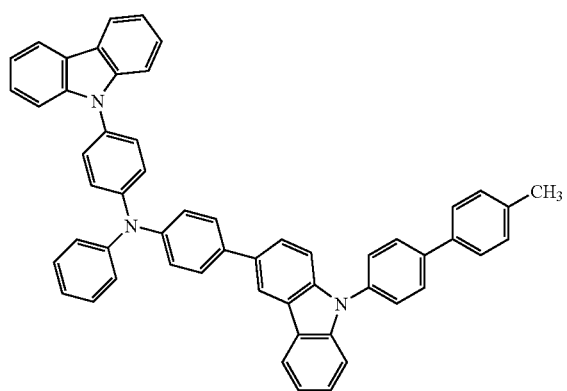

-continued
(159)
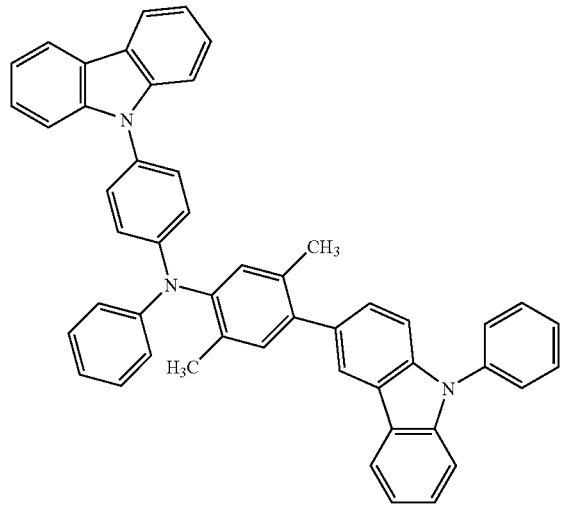
(160)
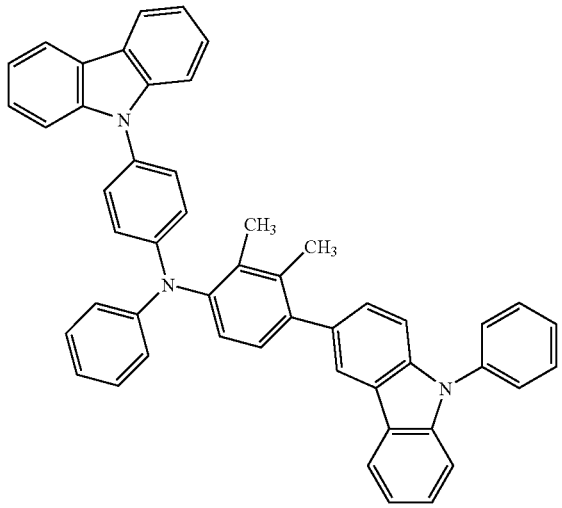
(161)
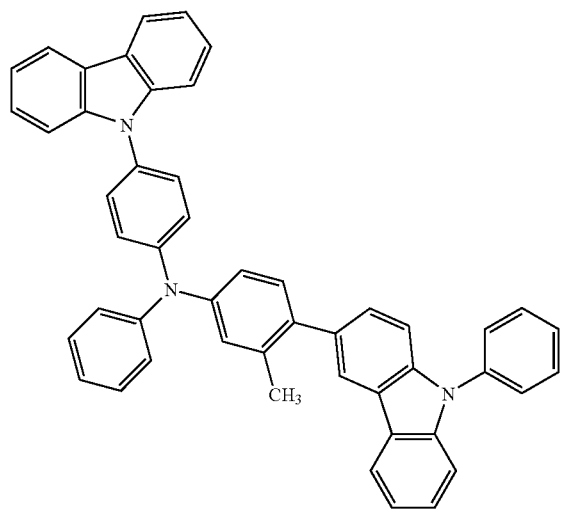
(162)
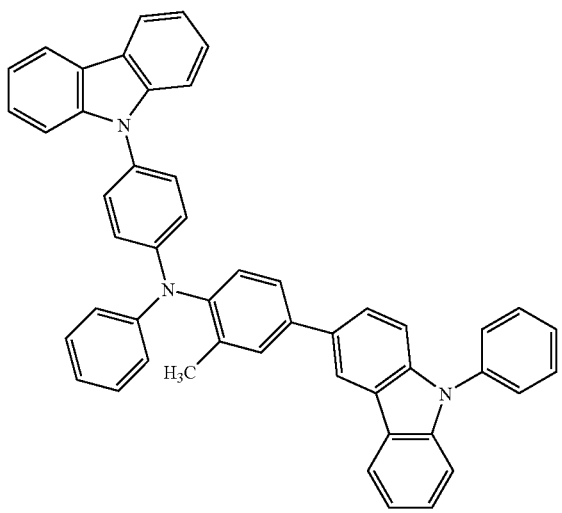
(163)
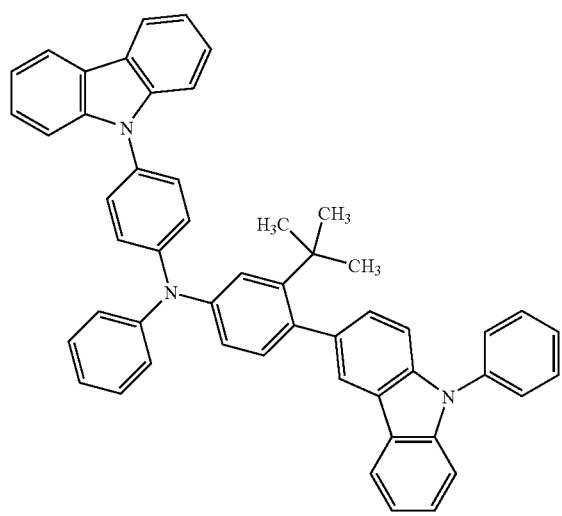
(164)
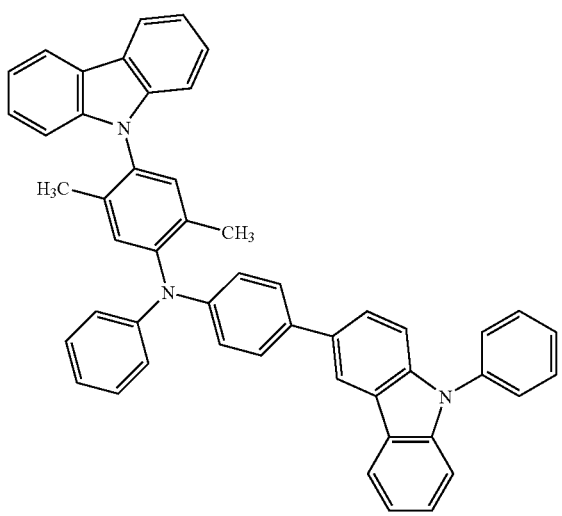

-continued
(165)
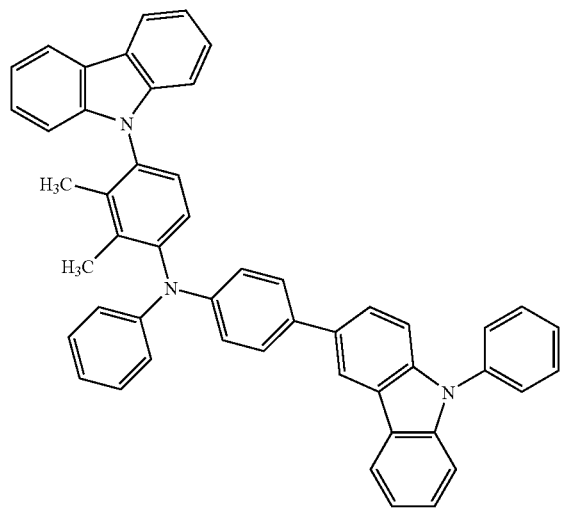
(166)
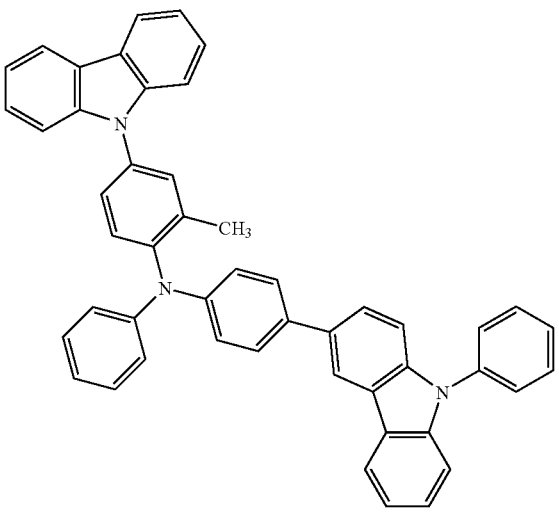
(167)
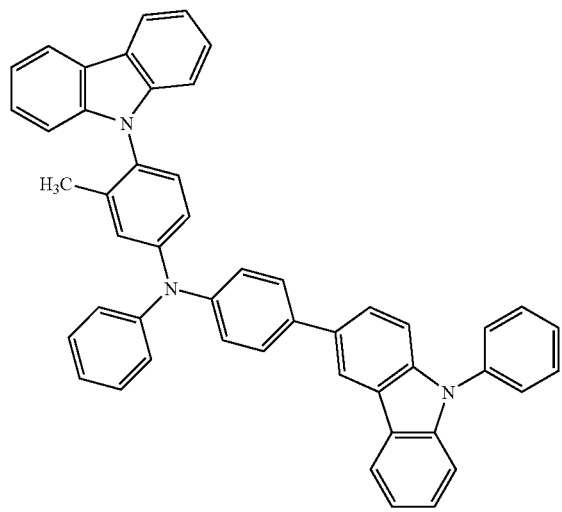
(168)
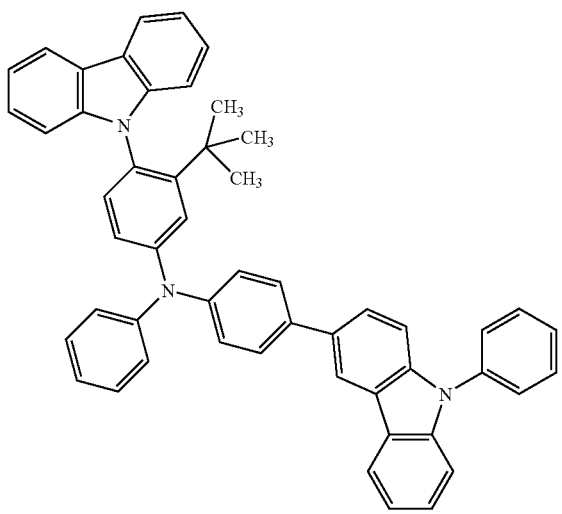
(169)
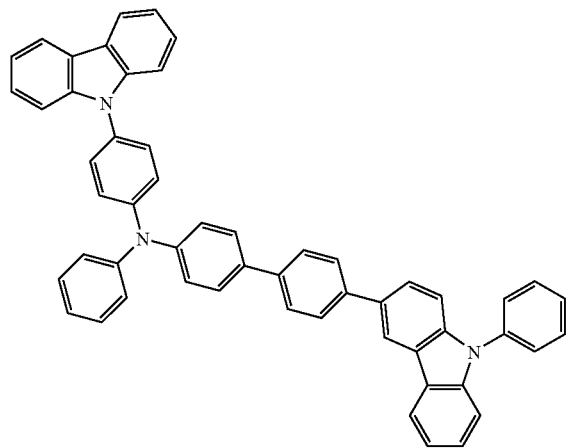
(170)
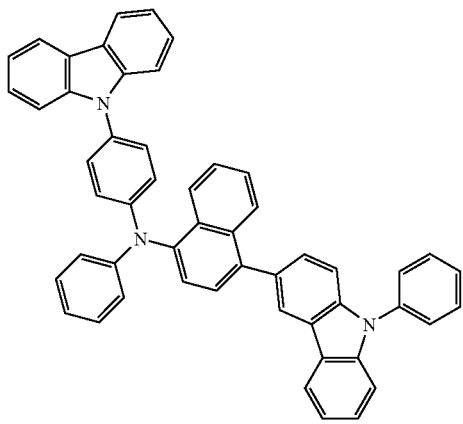

-continued
(171)
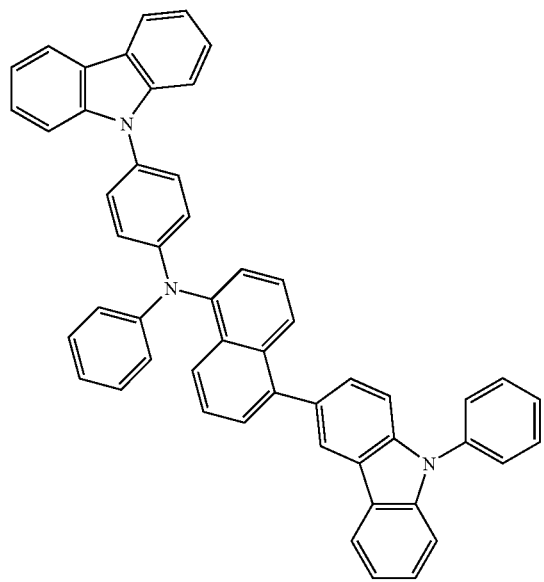
(172)
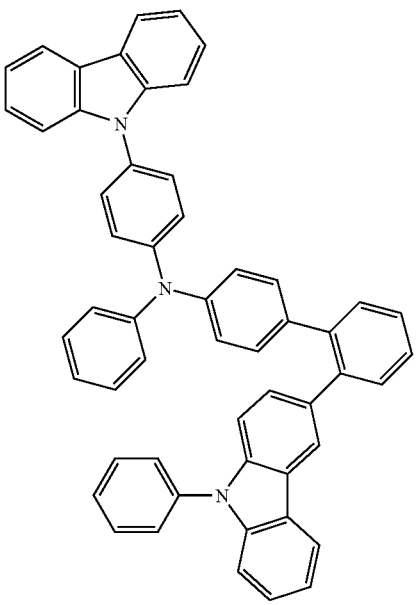
(173)
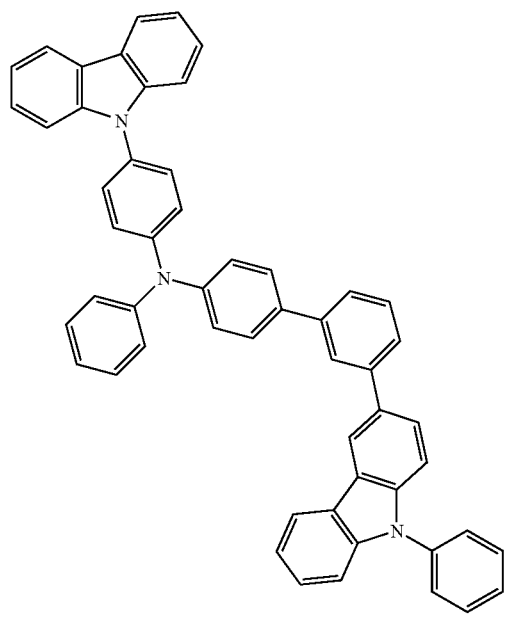
(174)
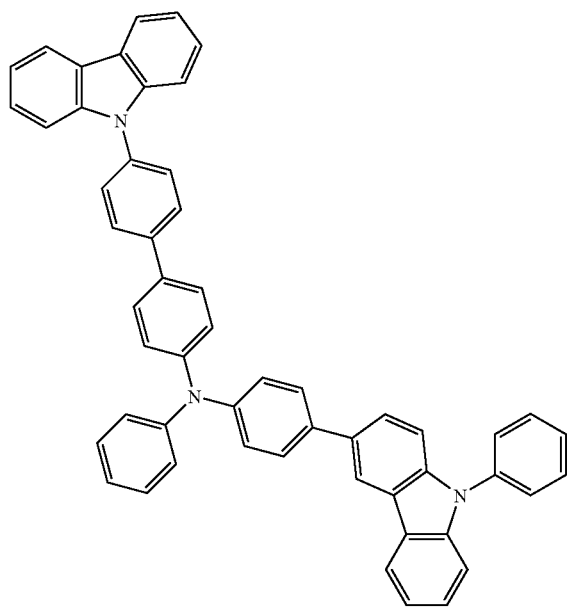

-continued
(175)
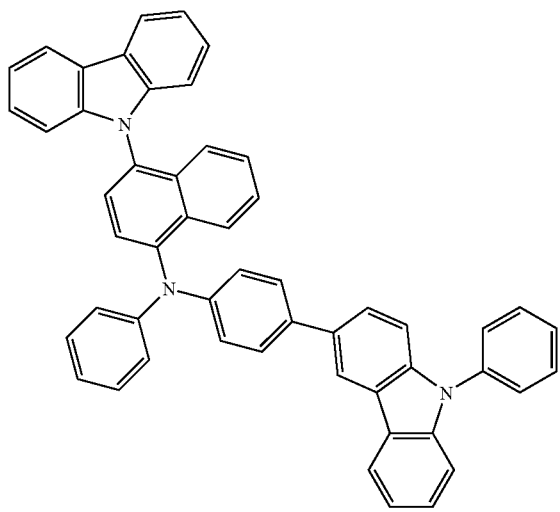
(176)
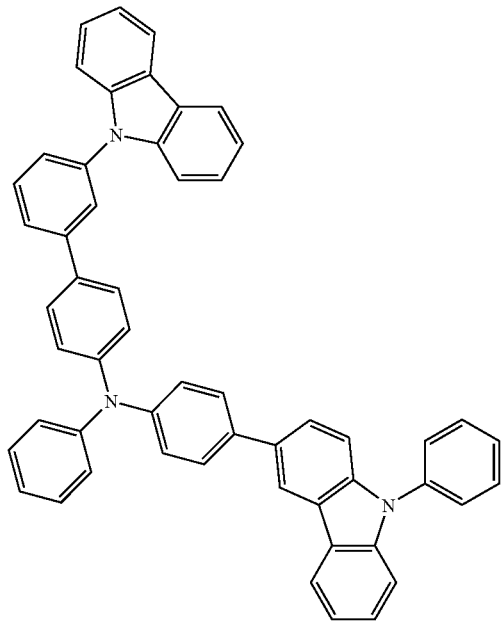
(177)
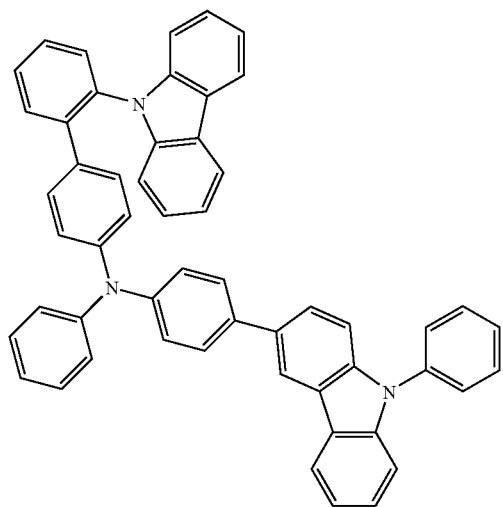
(178)
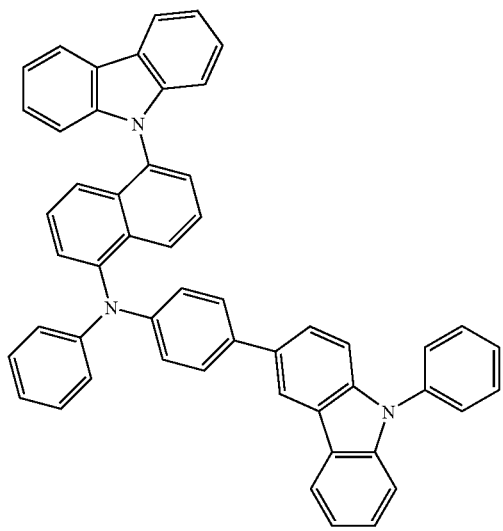

As a synthesis method of a carbazole derivative of the present invention, various reactions can be applied. For example, a carbazole derivative of the present invention can be synthesized by conducting a synthesis reaction shown in the following reaction formula (Z-1).

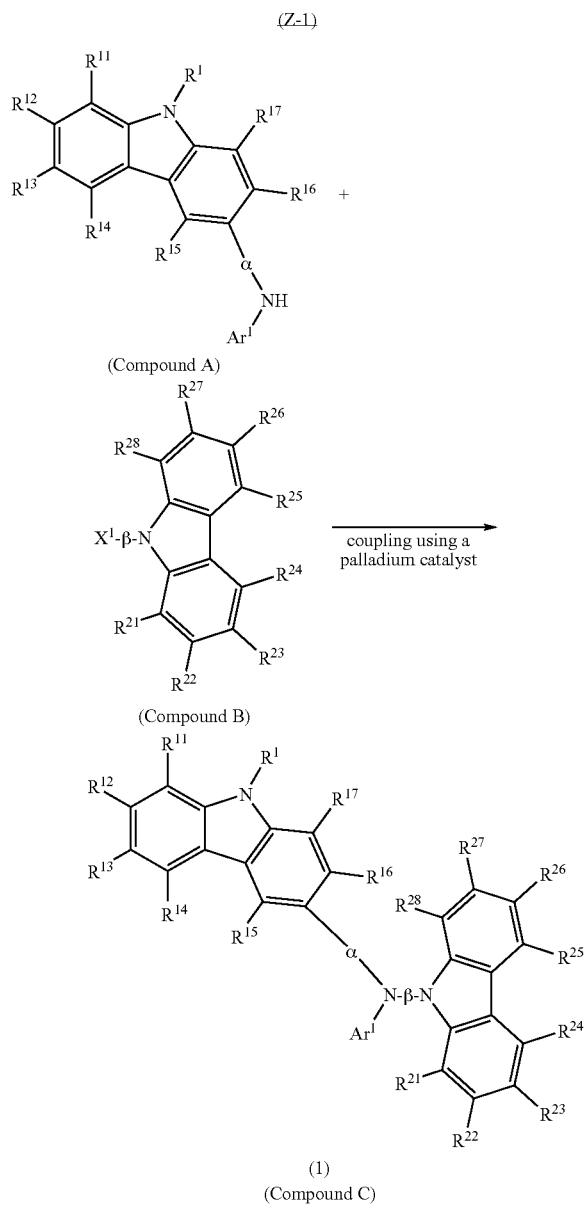

(Compound A)

(Compound B)

(1)
(Compound C)

An organic compound (Compound C) represented by the general formula (1) shown in this embodiment can be obtained in such a manner that an amine compound including carbazole (Compound A) and a halide carbazole derivative (Compound B) are coupled in the presence of a base through a Hartwig-Buchwald reaction using a palladium catalyst or through an Ullmann reaction using copper or a copper compound (the reaction formula (Z-1)).

In the reaction formula (Z-1), $X^1$ represents a halogen, preferably iodine or bromine.

In the case where the Hartwig-Buchwald reaction is carried out in the reaction formula (Z-1), bis(dibenzylideneacetone)palladium(0), palladium(II) acetate, or the like can be used as the palladium catalyst. Examples of ligands of the palladium catalysts that can be used in the reaction formula (Z-1) are tri(tert-butyl)phosphine, tri(n-hexyl)phosphine, tricyclohexylphosphine, and the like. Examples of bases that can be used in the reaction formula (Z-1) are organic bases such as sodium tert-butoxide, inorganic bases such as potassium carbonate, and the like. The solvents that can be used in the reaction formula (Z-1) are toluene, xylene, benzene, tetrahydrofuran, and the like.

The case of performing the Ullmann reaction in the reaction formula (Z-1) is described. In the reaction formula (Z-1), copper(I) iodide, copper(II) acetate, or the like can be used as the copper compound. Further, copper can be used other than the copper compound. As a base that can be used in the reaction formula (Z-1), inorganic bases such as potassium carbonate are given. Examples of solvents that can be used in the reaction formula (Z-1) are 1,3-dimethyl-3,4,5,6-tetrahydro-2(1H)pyrimidinone (DMPU), toluene, xylene, benzene, and the like. In the Ullmann reaction, the desired substance can be obtained in a shorter time and in a higher yield when the reaction temperature is 100° C. or higher; therefore, it is preferable to use DMPU or xylene that has a high boiling point. Because the reaction temperature is further preferably 150° C. or higher, DMPU is more preferably used.

In the above manner, the carbazole derivative of this embodiment can be synthesized.

The carbazole derivative of this embodiment is a material having a hole-transporting property.

One embodiment of the carbazole derivative of the present invention can be used as a hole-transporting material for a functional layer of a light-emitting element. For example, one embodiment of the carbazole derivative of the present invention can be used for a hole-transporting layer or a hole-injecting layer.

The carbazole derivative of this embodiment can be used alone as a light emission center material in a layer containing a light-emitting substance (a light-emitting layer). Alternatively, the carbazole derivative of this embodiment can also be used as a host material. Light emission from a dopant material functioning as a light-emitting substance can be obtained with a structure in which the dopant material functioning as a light-emitting substance is dispersed in the carbazole derivative of this embodiment. When the carbazole derivative of this embodiment is used as a host material, light emission from a dopant material can be efficiently obtained.

Further, a layer in which the carbazole derivative of this embodiment is dispersed in a (host) material having a larger band gap than the carbazole derivative of this embodiment can be used as a layer containing a light-emitting substance. In that case, light emission from the carbazole derivative of this embodiment can be obtained. That is, the carbazole derivative of this embodiment can also function as a dopant material.

[Embodiment 2]

One embodiment of a light-emitting element using a carbazole derivative of the present invention will be described with reference to FIG. 1A.

In one embodiment of the light-emitting element of the present invention, an EL layer including at least a layer containing a light-emitting substance (the layer is also referred to as a light-emitting layer) is provided between a pair of electrodes. The EL layer may also include a plurality of layers in addition to the layer containing a light-emitting substance. The plurality of layers are a combination of layers formed from a substance having a high carrier-injecting property and a substance having a high carrier-transporting property. Those layers are stacked so that a light-emitting region is formed in a region away from the electrodes, that is, carriers are recombined in a region away from the electrodes. In this specification, the layer formed from a substance having a high carrier-injecting property or a substance having a high carrier-transporting property is also referred to as a functional layer functioning to inject or transport carriers or the like. For the functional layer, it is possible to use a layer containing a substance having a high hole-injecting property (also referred to as a hole-injecting layer), a layer containing a substance having a high hole-transporting property (also referred to as a hole-transporting layer), a layer containing a substance having a high electron-injecting property (also referred to as an electron-injecting layer), a layer containing a substance having a high electron-transporting property (also referred to as an electron-transporting layer), and the like.

Figure 1B:
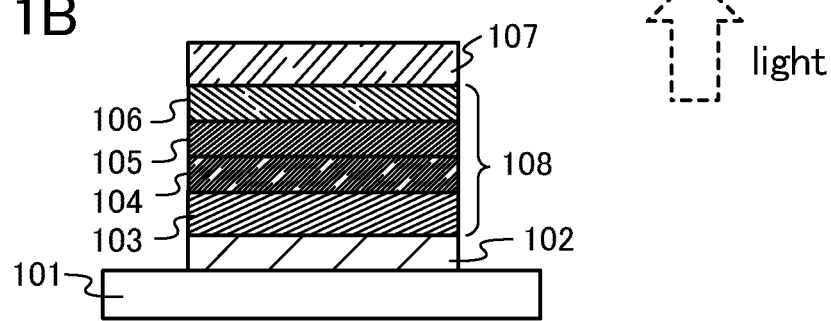
Figure 1C:
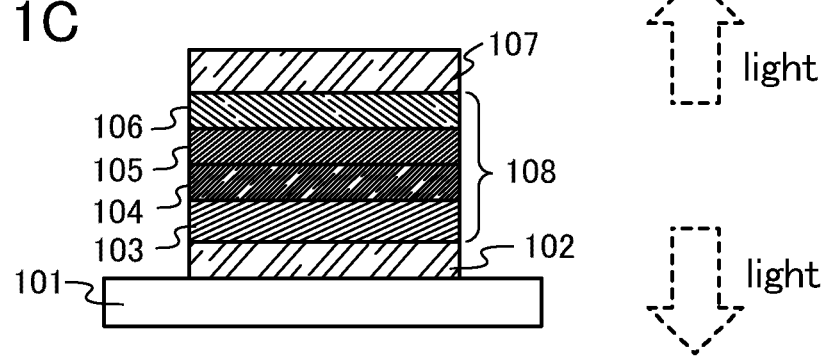

In a light-emitting element of this embodiment illustrated in each of FIGS. 1A to 1C, an EL layer 108 is provided between a pair of electrodes: a first electrode 102 and a second electrode 107. The EL layer 108 has a first layer 103, a second layer 104, a third layer 105, and a fourth layer 106. The light-emitting element in each of FIGS. 1A to 1C includes the first electrode 102 over a substrate 101; the first layer 103, the second layer 104, the third layer 105, and the fourth layer 106 stacked in this order over the first electrode 102; and the second electrode 107 provided thereover. Note that in this embodiment, the following description will be made on the assumption that the first electrode 102 functions as an anode and that the second electrode 107 functions as a cathode.

The substrate 101 is used as a support of the light-emitting element. For the substrate 101, glass, quartz, plastic, or the like can be used, for example. Alternatively, a flexible substrate may be used. A flexible substrate is a substrate that can be bent, such as a plastic substrate made of polycarbonate, polyarylate, or polyether sulfone, for example. Alternatively, a film (made of polypropylene, polyester, vinyl, polyvinyl fluoride, vinyl chloride, or the like), an inorganic film formed by evaporation, or the like can be used. Note that other substrates may also be used as long as they function as a support in a manufacturing process of the light-emitting element.

The first electrode 102 is preferably formed using a metal, an alloy, a conductive compound, a mixture of these, or the like each having a high work function (specifically, a work function of 4.0 eV or higher). Specifically, for example, indium tin oxide (ITO), indium tin oxide containing silicon or silicon oxide, indium zinc oxide (IZO), indium oxide containing tungsten oxide and zinc oxide (IWZO), and the like are given. Films of those conductive metal oxides are generally formed by sputtering, but they may be formed by a sol-gel method or the like. For example, a film of indium zinc oxide (IZO) can be formed by a sputtering method using a target in which zinc oxide is added to indium oxide at 1 wt % to 20 wt %. A film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like can be used.

The first layer 103 contains a substance having a high hole-injecting property. Molybdenum oxide, vanadium oxide, ruthenium oxide, tungsten oxide, manganese oxide, or the like can be used. Alternatively, the first layer 103 can be formed using any of the following materials: phthalocyanine-based compounds such as phthalocyanine (abbreviation: $H_2Pc$) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis[4-[bis(3-methylphenyl)amino]phenyl]-N,N'-diphenyl-[1,1'-biphenyl]-4,4'-diamine (abbreviation: DNTPD); high molecular compounds such as poly(3,4-ethylenedioxythiophene)/poly(styrenesulfonic acid) (PEDOT/PSS); and the like.

Further, the first layer 103 can be formed from a composite material formed by a composition of an organic compound and an inorganic compound. In particular, a composite material which contains an organic compound and an inorganic compound showing an electron-accepting property to the organic compound is excellent in a hole-injecting property and a hole-transporting property since electrons are transferred between the organic compound and the inorganic compound and carrier density is increased.

In the case where the first layer 103 is formed using a composite material formed by a composition of an organic compound and an inorganic compound, ohmic contact with the first electrode 102 becomes possible, and the material for the first electrode can be selected regardless of its work function.

As the inorganic compound used for the composite material, an oxide of a transition metal is preferably used. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among them, molybdenum oxide is especially preferable because it is stable in the air, has a low hygroscopic property, and is easily handled.

As the organic compound used for the composite material, various compounds such as an aromatic amine compound, a carbazole derivative, aromatic hydrocarbon, and a high molecular compound (such as oligomer, dendrimer, or polymer) can be used. Note that the organic compound used for the composite material is preferably an organic compound having a high hole-transporting property. Specifically, a substance having a hole mobility of $10^{-6}$ cm$^2$/Vs or higher is preferable. As the organic compound that can be used for the composite material, one embodiment of the carbazole derivative of the present invention can be used. The organic compounds that can be used for the composite material is specifically given below.

As aromatic amine compounds, for example, N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis[4-[bis(3-methylphenyl)amino]phenyl]-N,N'-diphenyl-[1',1'-biphenyl]-4,4'-diamine (abbreviation: DNTPD), 1,3,5-tris[N-(4-diphenylaminophenyl)-N-phenylamino]benzene (abbreviation: DPA3B), and the like can be given.

As carbazole derivatives that can be used for the composite material, for example, 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like can be given.

As other examples of carbazole derivatives that can be used for the composite material, for example, 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), 1,4-bis[4-(N-carbazolyl)phenyl]-2,3,5,6-tetraphenylbenzene, and the like can be given.

As aromatic hydrocarbon that can be used for the composite material, for example, 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like can be given. Alternatively, pentacene, coronene, or the like can also be used. As described above, aromatic hydrocarbon having a hole mobility of $1 \times 10^{-6}$ cm$^2$/Vs or higher and 14 to 42 carbon atoms is more preferable.

The aromatic hydrocarbon that can be used for the composite material may have a vinyl skeleton. As the aromatic hydrocarbon having a vinyl group, for example, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like can be given.

Moreover, a high molecular compound such as poly(N-vinylcarbazole) (abbreviation: PVK) or poly(4-vinyltriphenylamine) (abbreviation: PVTPA) can also be used.

The second layer 104 can be formed using a substance having a high hole-transporting property. In this embodiment, the second layer 104 can be formed using the carbazole derivative of the present invention which is described in Embodiment 1. Note that the second layer 104 is not limited to a single layer, and may be a mixed layer or a stack of two or more layers including a substance which has a higher hole-transporting property than an electron-transporting property and whose hole mobility is mainly $10^{-6}$ cm$^2$/Vs or higher.

The second layer 104 is preferably formed using a substance having a high hole-transporting property, specifically, an aromatic amine compound (that is, a compound having a benzene ring—nitrogen bond). As examples of materials which are widely used, 4,4'-bis[N-(3-methylphenyl)-N-phenylamino]biphenyl, a derivative thereof such as 4,4'-bis[N-(1-napthyl)-N-phenylamino]biphenyl (hereinafter referred to as NPB), a starburst aromatic amine compound such as 4,4',4''-tris(N,N-diphenyl-amino)triphenylamine, 4,4',4''-tris[N-(3-methylphenyl)-N-phenylamino]triphenylamine, and the like can be given. Most of the substances mentioned here have a hole mobility of $10^{-6}$ cm$^2$/Vs or higher. Note that the second layer 104 is not limited to a single layer, and may be a mixed layer or a stack of two or more layers including the aforementioned substances.

Alternatively, a material having a hole-transporting property may be added to a high molecular compound that is electrically inactive, such as PMMA.

Further alternatively, a high molecular compound such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N'-phenylamino}phenyl)methacrylamide] (abbreviation: PTPDMA), or poly[N,N-bis(4-butylphenyl)-N,N-bis(phenyl)benzidine (abbreviation: Poly-TPD) may be used, and further, the material having a hole-transporting property may be added to the above high molecular compound, as appropriate.

The third layer 105 contains a light-emitting substance (the layer is also referred to as a light-emitting layer). A carbazole derivative of the present invention exhibits blue light emission, and thus can be used as a light-emitting substance in a light-emitting element.

Alternatively, in the third layer 105, a carbazole derivative of the present invention can also be used as a host material. Light emission from a dopant material functioning as a light-emitting substance can be obtained with a structure in which the dopant material functioning as a light-emitting substance is dispersed in a carbazole derivative of the present invention.

A carbazole derivative of the present invention is a material having a hole-transporting property.

When a carbazole derivative of the present invention is used as a material in which another light-emitting substance is dispersed, an emission color originating from the light-emitting substance can be obtained. Further, it is possible to obtain a mixed color of an emission color originating from the carbazole derivative of the present invention and an emission color originating from the light-emitting substance which is dispersed in the carbazole derivative.

Further, a layer in which a carbazole derivative of the present invention is dispersed in a (host) material having a larger band gap than the carbazole derivative of the present invention can be used as a layer containing a light-emitting substance; thus, light emission from the carbazole derivative of the present invention can be obtained. That is, a carbazole derivative of the present invention also functions as a dopant material. In this case, a light-emitting element that can exhibit blue light emission can be manufactured by utilizing light emission of the carbazole derivative of the present invention.

Here, any of a variety of materials can be used as a light-emitting substance that is to be dispersed in a carbazole derivative of the present invention. Specifically, a fluorescent substance that emits fluorescence can be used, for example: N,N''-(2-tert-butylanthracene-9,10-diyldi-4,1-phenylene)bis[N,N,N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10,-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]

quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), or the like.

Alternatively, a phosphorescent substance that emits phosphorescence can be used, for example: bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis[2-(4'-perfluorophenylphenyl)pyridinato]iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$ (acac)), bis[2-(2'-benzo[4,5-a]thienyl)pyridinato-N,C$^{3'}$]iridium(III) acetylacetonate (abbreviation: Ir(btp)$_2$ (acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$ (acac)), 2,3,7,8,12,13,17,18-octaethyl-21H,23H-porphyrin platinum(II) (abbreviation: PtOEP), tris(1,3-diphenyl-1,3-propanedionato)(monophenanthroline)europium(III) (abbreviation: Eu(DBM)$_3$(Phen)), tris[1-(2-thenoyl)-3,3,3-trifluoroacetonato](monophenanthroline)europium(III) (abbreviation: Eu(TTA)$_3$(Phen)), or the like.

The fourth layer 106 can be formed using a substance having a high electron-transporting property. For example, the fourth layer 106 is formed using a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq). Other examples that can be used are metal complexes having an oxazole-based ligand or a thiazole-based ligand, such as bis[2-(2-hydroxyphenyl)benzoxazolato]zinc (abbreviation: Zn(BOX)$_2$) and bis[2-(2-hydroxyphenyl)benzothiazolato]zinc (abbreviation: Zn(BTZ)$_2$). Furthermore, as an alternative to metal complexes, the following can also be used: 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: Bphen), bathocuproine (abbreviation: BCP), and the like. Most of the substances mentioned here have an electron mobility of 10$^{-6}$ cm$^2$/Vs or higher. Further, the electron-transporting layer is not limited to a single layer, and may be a stack of two or more layers each containing any of the above substances.

Further, a layer having a function of promoting electron injection (an electron-injecting layer) may be provided between the fourth layer 106 and the second electrode 107. For the layer having a function of promoting electron injection, an alkali metal, an alkaline earth metal, or a compound thereof, such as lithium fluoride (LiF), cesium fluoride (CsF), or calcium fluoride (CaF$_2$) can be used.

Further, a composite material formed by a composition of an organic compound and an inorganic compound can be used for the layer having a function of promoting electron injection. For example, a layer of a substance having an electron-transporting property which further includes an alkali metal, an alkaline earth metal, or a compound thereof, such as a layer of Alq which further includes magnesium (Mg) can be used. Note that as the electron-injecting layer, it is preferable to use the layer formed of a substance having an electron-transporting property which further includes an alkali metal or an alkaline earth metal because electrons can be efficiently injected from the second electrode 107.

As a substance for forming the second electrode 107, a metal, an alloy, an electrically conductive compound, a mixture thereof, or the like each having a low work function (specifically, 3.8 eV or lower) can be used. As specific examples of such a cathode material, an element belonging to Group 1 or Group 2 of the periodic table, that is, an alkali metal such as lithium (Li) or cesium (Cs); an alkaline-earth metal such as magnesium (Mg), calcium (Ca), or strontium (Sr); an alloy containing the element belonging to Group 1 or Group 2 (MgAg, AlLi); a rare-earth metal such as europium (Eu) or ytterbium (Yb); an alloy thereof; and the like can be given. However, when a layer having a function of promoting electron injection is provided between the second electrode 107 and the fourth layer 106 so as to be stacked with the second electrode, various conductive materials such as Al, Ag, ITO, or ITO containing silicon or silicon oxide can be used for the second electrode 107 regardless of the work function.

A carbazole derivative of the present invention can also be used for a functional layer of a light-emitting element.

Further, for the formation of the first layer 103, the second layer 104, the third layer 105, and the fourth layer 106, any of a variety of methods such as an evaporation method, a sputtering method, a droplet discharging method (an inkjet method), a spin coating method, or a printing method can be employed. A different formation method may be employed for each electrode or each layer.

When a wet process is employed to form a thin film using a liquid composition which is obtained by dissolving a carbazole derivative of the present invention in a solvent, the thin film is formed in such a manner that a material for forming the thin film which includes the carbazole derivative of the present invention is dissolved in the solvent, the liquid composition is attached to a region where the thin film is to be formed, the solvent is removed, and the resulting material is solidified.

For the wet process, any of the following methods can be employed: a spin coating method, a roll coating method, a spray method, a casting method, a dipping method, a droplet discharging (ejection) method (an inkjet method), a dispenser method, a variety of printing methods (a method by which a thin film can be formed in a desired pattern, such as screen (stencil) printing, offset (planographic) printing, letterpress printing, or gravure (intaglio) printing, or the like. Note that without limitation to the above methods, the compositions of the present invention can be used as long as a method in which a liquid composition is used is employed.

In the above composition, a variety of solvents can be used. For example, the carbazole derivative can be dissolved in a solvent that has an aromatic ring (e.g., a benzene ring), such as toluene, xylene, methoxybenzene (anisole), dodecylbenzene, or a mixed solvent of dodecylbenzene and tetralin. Further, the above carbazole derivative can also be dissolved in an organic solvent which does not include an aromatic ring, such as dimethylsulfoxide (DMSO), dimethylformamide (DMF), or chloroform.

As other examples of the solvents, there are ketone-based solvents such as acetone, methyl ethyl ketone, diethyl ketone, n-propyl methyl ketone, and cyclohexanone; ester-based solvents such as ethyl acetate, n-propyl acetate, n-butyl acetate, ethyl propionate, γ-butyrolactone, and diethyl carbonate; ether-based solvents such as diethyl ether, tetrahydrofuran, and dioxane; alcohol-based solvents such as ethanol, isopropanol, 2-methoxyethanol, and 2-ethoxyethanol; and the like.

Further, a composition which is described in this embodiment may also contain another organic material. As the organic material, an aromatic compound or a heteroaromatic compound which is solid at room temperature can be given. For the organic material, a low molecular compound or a high molecular compound can be used. When a low molecular compound is used, a low molecular compound (which may be referred to as a medium molecular compound) including a substituent that can increase the solubility in a solvent is preferably used.

The composition may further include a binder in order to improve the quality of a film which is formed. A high molecular compound that is electrically inactive is preferably used as the binder. Specifically, polymethylmethacrylate (abbreviation: PMMA), polyimide, or the like can be used.

In the light-emitting element of this embodiment which has the structure as described above, the potential difference between the first electrode 102 and the second electrode 107 makes current flow, whereby holes and electrons recombine in the third layer 105 containing a substance having a high light-emitting property and thus light is emitted. That is, a light-emitting region is formed in the third layer 105.

Emitted light is extracted to the outside through one or both of the first electrode 102 and the second electrode 107. Accordingly, one or both of the first electrode 102 and the second electrode 107 is/are formed using a substance having a light-transmitting property. When only the first electrode 102 is formed using a substance having a light-transmitting property, emitted light is extracted from the substrate side through the first electrode 102, as illustrated in FIG. 1A. In contrast, when only the second electrode 107 is formed using a substance having a light-transmitting property, emitted light is extracted from the side opposite to the substrate through the second electrode 107, as illustrated in FIG. 1B. When both the first electrode 102 and the second electrode 107 are formed using a substance having a light-transmitting property, emitted light is extracted from both the substrate side and the side opposite to the substrate through the first electrode 102 and the second electrode 107, as illustrated in FIG. 1C.

Note that the structure of the layers provided between the first electrode 102 and the second electrode 107 is not limited to the above. A structure other than the above may alternatively be employed as long as a light-emitting region in which holes and electrons are recombined is provided in a portion away from the first electrode 102 and the second electrode 107 in order to prevent quenching due to proximity of the light-emitting region to a metal.

In other words, there is no particular limitation on the stack structure of the layers as long as the hole-transporting layer or the light-emitting layer which contains a carbazole derivative of the present invention is freely combined with the layer containing a substance having a high electron-transporting property, the layer containing a substance having a high hole-transporting property, the layer containing a substance having a high electron-injecting property, the layer containing a substance having a high hole-injecting property, the layer containing a bipolar substance (a substance having a high electron-transporting and a high hole-transporting property), the layer containing a hole-blocking material, and the like.

Figure 2:
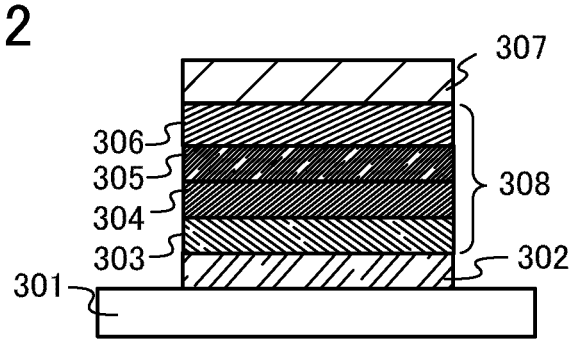
FIG. 2 is a view illustrating a light-emitting element.

In a light-emitting element illustrated in FIG. 2, over a substrate 301, an EL layer 308 is provided between a pair of electrodes: a first electrode 302 and a second electrode 307. The EL layer 308 includes a first layer 303 formed from a substance having a high electron-transporting property, a second layer 304 containing a light-emitting substance, a third layer 305 formed from a substance having a high hole-transporting property, and a fourth layer 306 formed from a substance having a high hole-injecting property. The first electrode 302 which functions as a cathode, the first layer 303 formed from a substance having a high electron-transporting property, the second layer 304 containing a light-emitting substance, the third layer 305 formed from a substance having a high hole-transporting property, the fourth layer 306 formed from a substance having a high hole-injecting property, and the second electrode 307 which functions as an anode are stacked in that order.

A specific method for forming a light-emitting element is described below.

In a light-emitting element of the present invention, an EL layer is interposed between a pair of electrodes. The EL layer includes at least a layer containing a light-emitting substance (the layer is also referred to as a light-emitting layer). Furthermore, in addition to the layer containing a light-emitting substance, the EL layer may include another functional layer (e.g., a hole-injecting layer, an electron-transporting layer, and/or an electron-injecting layer). The electrodes (the first electrode and the second electrode), the layer containing a light-emitting substance, and the functional layer may be formed by a wet process such as a droplet discharge method (an inkjet method), a spin coating method, or a printing method, or by a dry process such as a vacuum evaporation method, a CVD method, or a sputtering method. The use of a wet process enables the formation at atmospheric pressure using a simple apparatus and process, and thus advantageous effects of simplifying the process and improving the productivity can be obtained. In contrast, in a dry process, dissolution of a material is not needed, and thus, a material that has low solubility in a solution can be used, which leads to expansion of material choices.

All the thin films included in the light-emitting element may be formed by a wet process. In this case, the light-emitting element can be manufactured with only facilities needed for a wet process. Alternatively, formation of the stacked layers up to formation of the layer containing a light-emitting substance may be performed by a wet process whereas the functional layer, the second electrode, and the like which are stacked over the layer containing a light-emitting substance may be formed by a dry process. Further alternatively, the first electrode and the functional layer may be formed by a dry process before the formation of the layer containing a light-emitting substance whereas the layer containing a light-emitting substance, the functional layer stacked thereover, and the second electrode may be formed by a wet process. It is needless to say that the present invention is not limited thereto. The light-emitting element can be formed by appropriate selection from a wet process and a dry process depending on a material that is to be used, a required film thickness, and an interface state.

In this embodiment, the light-emitting element is manufactured over a substrate made of glass, plastic, or the like. When a plurality of such light-emitting elements are manufactured over one substrate, a passive matrix light-emitting device can be manufactured. Alternatively, for example, thin film transistors (TFTs) are formed over a substrate made of glass, plastic, or the like, and then, light-emitting elements may be manufactured over an electrode that is electrically connected to the TFTs. Thus, an active matrix light-emitting device in which drive of the light-emitting elements is controlled by the TFTs can be manufactured. Note that there is no particular limitation on the structure of the TFT. Either a staggered TFT or an inverted staggered TFT may be employed. Further, there is no particular limitation on the crystallinity of a semiconductor used for forming the TFTs, and an amorphous semiconductor or a crystalline semiconductor may be used. In addition, a driver circuit formed over a TFT substrate may be formed using n-channel and p-channel TFTs, or using either n-channel or p-channel TFTs.

One embodiment of the carbazole derivative of the present invention is a material having a hole-transporting property.

One embodiment of the carbazole derivative of the present invention can be used for a hole-transporting layer.

In addition, one embodiment of the carbazole derivative of the present invention can be used either as a light-emitting material (including a dopant material) or as a host material in a light-emitting layer of a light-emitting element.

Light emission can be efficiently obtained from a light-emitting element in which one embodiment of the carbazole derivative of the present invention is used as a hole-transporting layer.

Therefore, a light-emitting element, a light-emitting device, and an electronic device with reduced power consumption can be provided by using one embodiment of the carbazole derivative of the present invention.

[Embodiment 3]

Figure 11A:
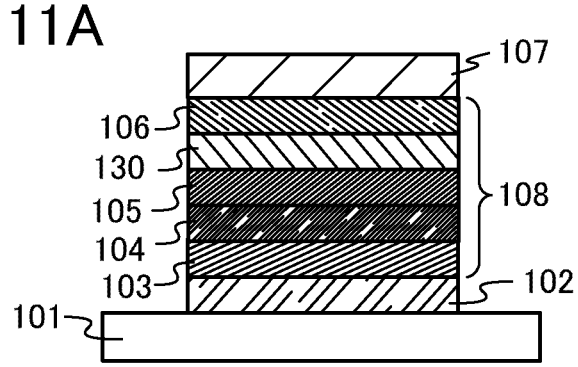
FIGS. 11A and 11B are views each illustrating a light-emitting element.
Figure 11B:
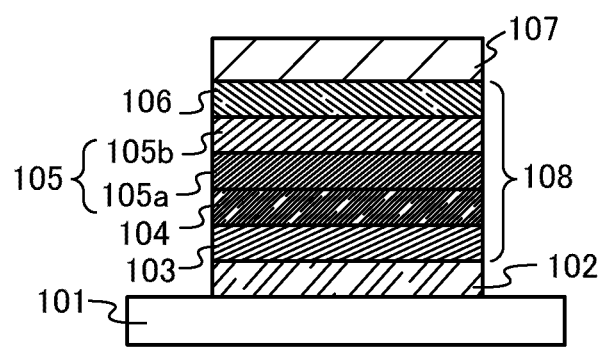

In this embodiment, a light-emitting element having a different structure from the structure described in Embodiment 2 will be described with reference to FIGS. 11A and 11B.

A layer which controls movement of electron carriers may be provided between an electron-transporting layer and a light-emitting layer. FIG. 11A illustrates a structure in which a layer 130 which controls movement of electron carriers is provided between a fourth layer 106 which functions as an electron-transporting layer and a third layer 105 which functions as a light-emitting layer (the third layer 105 is also referred to as a light-emitting layer 105). The layer 130 which controls movement of electron carriers is a layer which is formed by adding a small amount of substance having a high electron-trapping property to the above material having a high electron-transporting property, or a layer formed by adding a material having a hole-transporting property with a low lowest unoccupied molecular orbital (LUMO) energy level to a material having a high electron-trapping property. With such a layer, movement of electron carriers is controlled, whereby carrier balance can be adjusted. Such a structure is very effective in suppressing a problem (such as shortening of element lifetime) caused when electrons pass through the third layer 105.

Further, another structure may be employed in which the light-emitting layer 105 includes two or more layers. FIG. 11B illustrates an example in which the light-emitting layer 105 includes two layers: a first light-emitting layer 105a and a second light-emitting layer 105b.

If the first light-emitting layer 105a and the second light-emitting layer 105b are stacked in that order over the second layer 104 which functions as a hole-transporting layer to form the light-emitting layer 105, for example, a substance having a hole-transporting property can be used as a host material of the first light-emitting layer 105a and a substance having an electron-transporting property can be used for the second light-emitting layer 105b.

A carbazole derivative of the present invention can be used alone for a light-emitting layer. Further, a carbazole derivative of the present invention can also be used either as a host material or as a dopant material.

If a carbazole derivative of the present invention is used as a host material, light emission from a dopant material that functions as a light-emitting substance can be obtained with a structure in which the dopant material that functions as a light-emitting substance is dispersed in the carbazole derivative of the present invention.

On the other hand, when a carbazole derivative of the present invention is used as a dopant material, light emission from the carbazole derivative of the present invention can be obtained with a structure in which the carbazole derivative of the present invention is added to a layer formed from a (host) material which has a larger band gap than the carbazole derivative of the present invention.

A carbazole derivative of the present invention can be used for the first light-emitting layer 105a and the second light-emitting layer 105b, and can be used as a dopant material of each layer. In the case where a carbazole derivative of the present invention is used alone as a light-emitting layer or used as a host material, the carbazole derivative of the present invention can be used for the first light-emitting layer 105a having a hole-transporting property.

Note that this embodiment can be combined as appropriate with another embodiment.

[Embodiment 4]

In this embodiment, one mode of a light-emitting element having a structure in which a plurality of light-emitting units according to the present invention are stacked (hereinafter this type of light-emitting element is referred to as a stacked element) will be described with reference to FIG. 3. This light-emitting element has a plurality of light-emitting units between a first electrode and a second electrode.

Figure 3:
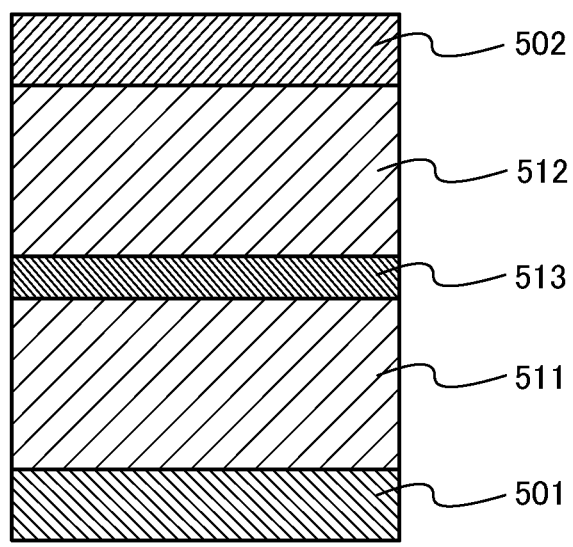
FIG. 3 is a view illustrating a light-emitting element.

In FIG. 3, a first light-emitting unit 511 and a second light-emitting unit 512 are stacked between a first electrode 501 and a second electrode 502. In the formation of each the first electrode 501 and the second electrode 502, electrodes similar to those described in Embodiment 2 can be used. The structures of the first light-emitting unit 511 and the second light-emitting unit 512 may be the same or different. Their structures can be similar to that described in Embodiment 2.

A charge generation layer 513 contains a composite material of an organic compound and a metal oxide. This composite material of an organic compound and a metal oxide is a composite material described in Embodiment 2 and includes an organic compound and a metal oxide such as $V_2O_5$, $MoO_3$ or $WO_3$. As the organic compound, various compounds such as an aromatic amine compound, a carbazole derivative, aromatic hydrocarbon, and a high molecular compound (oligomer, dendrimer, polymer, or the like) can be given. An organic compound having a hole mobility of $10^{-6}$ cm$^2$/Vs or higher is preferably used as a hole-transporting organic compound. Note that any organic compound other than the above substance may also be used as long as its hole-transporting property is higher than its electron-transporting property. The composite material of an organic compound and a metal oxide is excellent in a carrier-injecting property and a carrier-transporting property; therefore, low-voltage driving and low-current driving can be achieved.

Note that the charge generation layer 513 may be formed by a combination of a composite material of an organic compound and a metal oxide and another material. For example, a layer containing the composite material of an organic compound and a metal oxide may be used in combination with a layer containing a compound selected from an electron-donating substance and a compound having a high electron-transporting property. Further, a layer containing the composite material of an organic compound and a metal oxide may be used in combination with a transparent conductive film.

In any case, any layer can be employed as the charge generation layer 513 provided between the first light-emitting unit 511 and the second light-emitting unit 512 as long as the layer injects electrons into one of these light-emitting units and holes into the other when voltage is applied to the first electrode 501 and the second electrode 502.

Although the light-emitting element having two light-emitting units is described in this embodiment, a light-emitting element in which three or more light-emitting units are stacked can be employed in a similar way. When the charge generation layer is provided between the pair of electrodes so as to partition the plural light-emitting units like in the light-emitting element of this embodiment, light emission from a high luminance region can be achieved while the current density is kept low. Accordingly, an element with a long lifetime can be realized. Further, in the case where the light-emitting element is applied to a lighting device, voltage drop due to resistance of an electrode material can be reduced. Accordingly, light can be uniformly emitted from a large area. Moreover, a light-emitting device of low power consumption that can be driven at low voltage can be achieved.

Note that this embodiment can be combined as appropriate with another embodiment.

[Embodiment 5]

In this embodiment, a light-emitting device manufactured using one embodiment of the carbazole derivative of the present invention will be described.

In this embodiment, a light-emitting device manufactured using one embodiment of the carbazole derivative of the present invention will be described with reference to FIGS. 4A and 4B. Note that FIG. 4A is a top view of the light-emitting device, and FIG. 4B is a cross-sectional view taken along lines A-B and C-D of FIG. 4A. Reference numerals 601, 602, and 603 denote a driver circuit portion (a source side driver circuit), a pixel portion, and a driver circuit portion (a gate side driver circuit), respectively, which are indicated by dotted lines. Further, reference numeral 604 denotes a sealing substrate and reference numeral 605 denotes a sealant. A portion surrounded by the sealant 605 is a space 607.

Note that a lead wiring 608 is a wiring for transmitting signals to be input into the source side driver circuit 601 and the gate side driver circuit 603 and for receiving signals such as a video signal, a clock signal, a start signal, and a reset signal from an FPC (flexible printed circuit) 609 serving as an external input terminal. Although only the FPC is illustrated here, this FPC may be provided with a printed wiring board (PWB). The light-emitting device in this specification includes, in its category, not only a light-emitting device itself but also a light-emitting device provided with an FPC or a PWB.

Next, a cross-sectional structure is described with reference to FIG. 4B. The driver circuit portions and the pixel portion are formed over an element substrate 610, but only the source side driver circuit portion 601, which is a driver circuit portion, and one pixel of the pixel portion 602 are illustrated in FIG. 4B.

Note that a CMOS circuit in which an n-channel TFT 623 and a p-channel TFT 624 are formed in combination is formed in the source side driver circuit 601. The driver circuit may be formed by a variety of CMOS circuits, PMOS circuits, or NMOS circuits. Although the driver integrated device which has the driver circuit formed over the substrate is described in this embodiment, the driver circuit does not always have to be formed over the substrate. It is also possible to form the driver circuit not over the substrate but outside the substrate.

Moreover, the pixel portion 602 includes a plurality of pixels including a switching TFT 611, a current control TFT 612, and a first electrode 613 electrically connected to a drain of the current control TFT 612. Note that an insulator 614 is formed covering an end of the first electrode 613. Here, a positive photosensitive acrylic resin film is used for the insulator 614.

In order to improve the coverage, the insulator 614 is formed to have a curved surface with curvature at its upper or lower end portion. For example, in the case of using positive photosensitive acrylic for the insulator 614, only the upper end portion of the insulator 614 preferably has a curved surface with a radius of curvature (0.2 μm to 0.3 μm). Further, the insulator 614 can be formed using either a negative type that becomes insoluble in an etchant by light irradiation or a positive type that becomes soluble in an etchant by light irradiation.

A layer 616 containing a light-emitting substance and a second electrode 617 are formed over the first electrode 613. Here, the first electrode 613 serving as an anode is preferably formed using a material with a high work function. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like can be used. Alternatively, a stack of a titanium nitride film and a film containing aluminum as its main component, a stack of three layers of a titanium nitride film, a film containing aluminum as its main component, and a titanium nitride film, or the like can be used. Note that when the first electrode 613 has a stacked-layer structure, the resistance can be reduced as a wiring and favorable ohmic contact can be obtained. Further, the first electrode 613 can function as an anode.

The layer 616 containing a light-emitting substance is formed by any of a variety of methods such as an evaporation method using an evaporation mask, a droplet discharge method such as an inkjet method, a printing method, and a spin coating method. The layer 616 containing a light-emitting substance contains the carbazole derivative of the present invention which is described in Embodiment 1. As another material contained in the layer 616 containing a light-emitting substance, a low molecular material, a medium molecular material (including an oligomer and a dendrimer), or a high molecular material may be used.

Further, as a material used for the second electrode 617, which is formed over the layer 616 containing a light-emitting substance and functions as a cathode, a material having a low work function (Al, Mg, Li, Ca, or an alloy or a compound thereof such as MgAg, MgIn, AlLi, LiF, or $CaF_2$) is preferably used. In the case where light generated in the layer 616 containing a light-emitting substance passes through the second electrode 617, the second electrode 617 is preferably formed using a stack of a thin metal film having a reduced thickness and a transparent conductive film (such as ITO, indium oxide containing zinc oxide at 2 wt % to 20 wt %, indium tin oxide containing silicon or silicon oxide, or zinc oxide (ZnO)).

By attaching the sealing substrate 604 to the element substrate 610 using the sealant 605, the light-emitting element 618 is provided in the space 607 which is surrounded by the element substrate 610, the sealing substrate 604, and the sealant 605. Note that the space 607 is filled with filler. The space 607 is sometimes filled with an inert gas (such as nitrogen or argon) or the sealant 605.

Note that an epoxy-based resin is preferably used for the sealant 605. In addition, it is desirable to use a material that allows permeation of moisture or oxygen as little as possible. As the sealing substrate 604, a plastic substrate formed from fiberglass-reinforced plastics (FRP), polyvinyl fluoride (PVF), polyester, acrylic, or the like can be used besides a glass substrate or a quartz substrate.

In this manner, a light-emitting device manufactured using one embodiment of the carbazole derivative of the present invention can be obtained.

The carbazole derivative of the present invention is a material having a hole-transporting property.

A light-emitting element with high light emission efficiency can be obtained by using a carbazole derivative of the present invention; therefore, a light-emitting element, a light-emitting device, and an electronic device with reduced power consumption can be obtained.

Figure 5A:
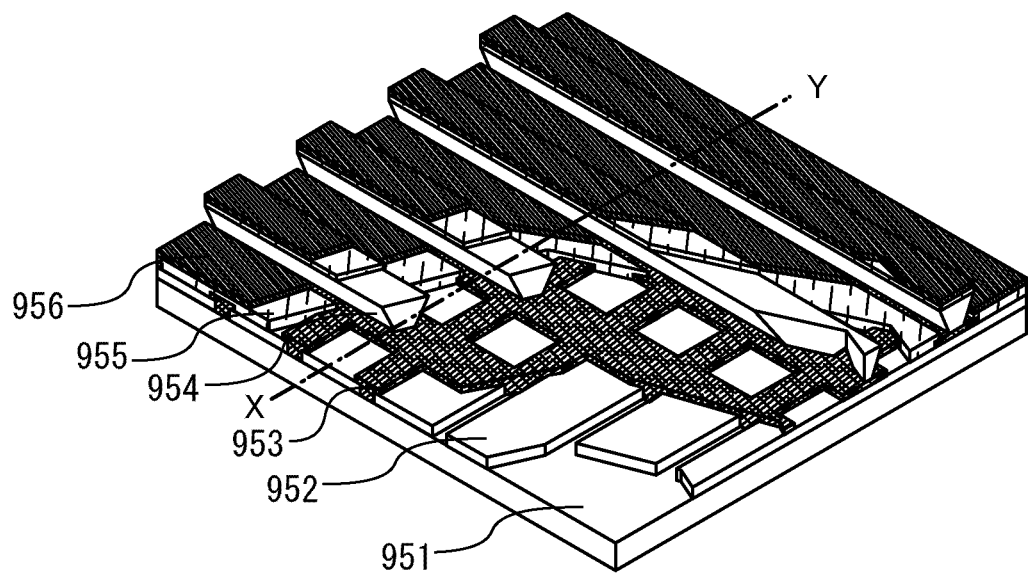
FIGS. 5A and 5B are views illustrating a light-emitting device.
Figure 5B:
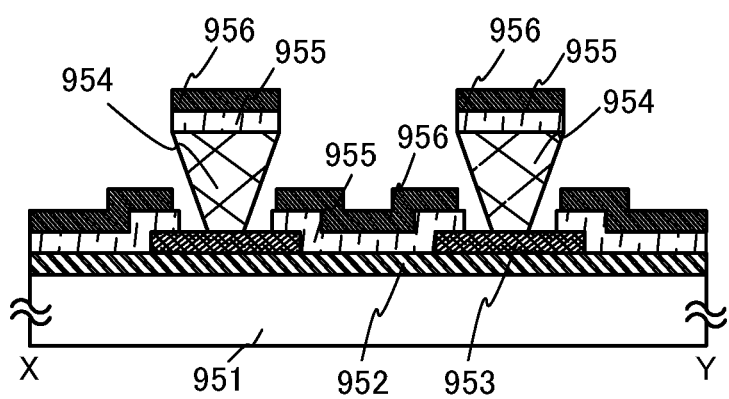

Although an active matrix light-emitting device in which driving of a light-emitting element is controlled by a transistor is described in this embodiment, a passive matrix light-emitting device may also be employed. FIGS. 5A and 5B illustrate a passive matrix light-emitting device manufactured by applying the present invention. In FIGS. 5A and 5B, a layer 955 containing a light-emitting substance is provided between an electrode 952 and an electrode 956 over a substrate 951. An edge portion of the electrode 952 is covered with an insulating layer 953. A partition layer 954 is provided over the insulating layer 953. The sidewalls of the partition layer 954 are aslope so that the distance between both sidewalls is gradually reduced toward the surface of the substrate. In other words, a cross section taken along the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other one of the pair of parallel sides). By provision of the partition layer 954 in this manner, defects of the light-emitting element due to static charge and the like can be prevented. A light-emitting device with high reliability can be obtained also in the case of a passive matrix light-emitting device by including a light-emitting element of the present invention.

[Embodiment 6]

In this embodiment, an electronic device of the present invention which includes the light-emitting device described in Embodiment 5 will be described. An electronic device of the present invention includes the carbazole derivative described in Embodiment 1, and has a display portion with reduced power consumption.

As examples of electronic devices including a light-emitting element formed using one embodiment of the carbazole derivative of the present invention, cameras such as video cameras and digital cameras, goggle type displays, navigation systems, audio reproducing devices (car audio systems, audio component systems, and the like), computers, game machines, portable information terminals (mobile computers, cellular phones, portable game machines, and electronic book readers), image reproducing devices each provided with a recording medium (specifically, devices that are capable of reproducing a recording media such as a digital versatile disc (DVD) and equipped with a display device that can display an image), and the like can be given. Specific examples of these electronic devices are illustrated in FIGS. 6A to 6E.

Figure 6A:
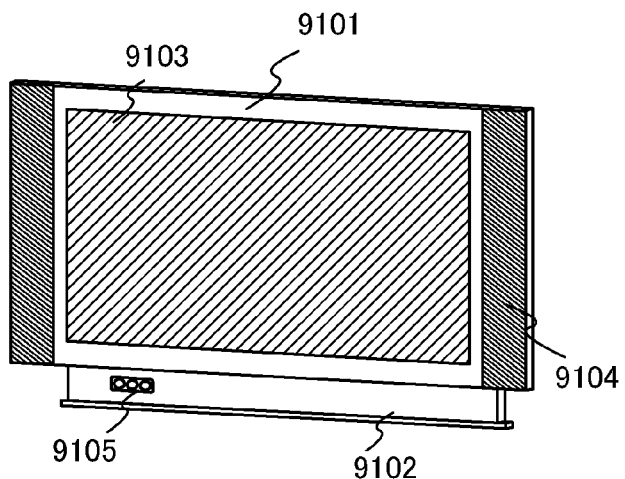
FIGS. 6A to 6E are views each illustrating an electronic device.

FIG. 6A illustrates a television device according to the present invention, which includes a housing 9101, a support 9102, a display portion 9103, a speaker portion 9104, a video input terminal 9105, and the like. In the display portion 9103 of this television device, light-emitting elements similar to those described in any of Embodiments 2 to 4 are arranged in matrix. The light-emitting elements have a feature of reduced power consumption. The display portion 9103 which includes the light-emitting elements has a similar feature; therefore, in this television device, reduction in power consumption is achieved. Thus, a product which is more suitable for living environment can be provided.

Figure 6B:
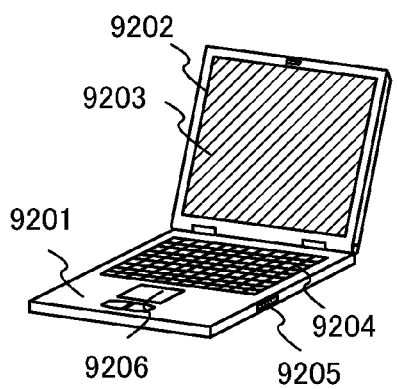

FIG. 6B illustrates a computer according to the present invention, which includes a main body 9201, a housing 9202, a display portion 9203, a keyboard 9204, an external connection port 9205, a pointing device 9206, and the like. In the display portion 9203 of this computer, light-emitting elements similar to those described in any of Embodiments 2 to 4 are arranged in matrix. The light-emitting elements have a feature of reduced power consumption. The display portion 9203 which includes the light-emitting elements has a similar feature; therefore, in this computer, reduction in power consumption is achieved. Thus, a product which is more suitable for usage environment can be provided.

Figure 6C:
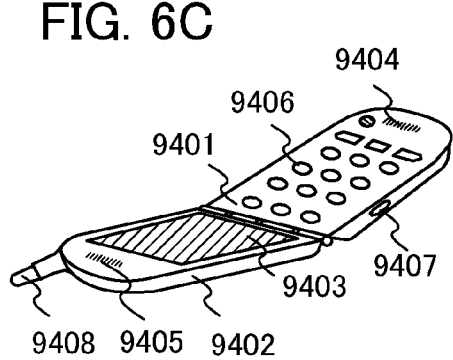

FIG. 6C illustrates a cellular phone according to the present invention, which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to those described in any of Embodiments 2 to 4 are arranged in matrix. The light-emitting elements have a feature of reduced power consumption. The display portion 9403 which includes the light-emitting elements has a similar feature; therefore, in this cellular phone, reduction in power consumption is achieved. Thus, a product which is more suitable for being carried around can be provided.

Figure 6D:
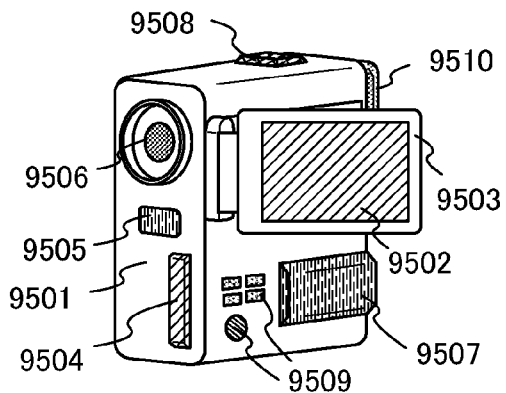

FIG. 6D illustrates a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the display portion 9502 of this camera, light-emitting elements similar to those described in any of Embodiments 2 to 4 are arranged in matrix. The light-emitting elements have a feature of reduced power consumption. The display portion 9502 which includes the light-emitting elements has a similar feature; therefore, in this camera, reduction in power consumption is achieved. Thus, a product which is more suitable for being carried around can be provided.

Figure 6E:
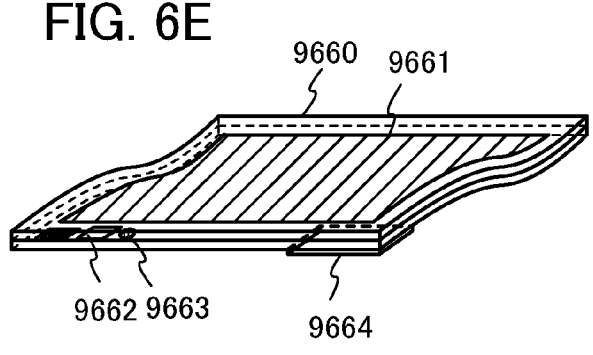

FIG. 6E illustrates an electronic paper according to the present invention, which is flexible and includes a main body 9660, a display portion 9661 which displays images, a driver IC 9662, a receiver 9663, a film battery 9664, and the like. The driver IC, the receiver, or the like may be mounted using a semiconductor component. In the electronic paper according to the present invention, the main body 9660 is formed using a flexible material such as plastic or a film. In this electronic paper, the display portion 9661 has light-emitting elements similar to those described in any of Embodiments 2 to 4, which are arranged in matrix. The light-emitting elements have features of a long lifetime and low power consumption. The display portion 9661 which includes the light-emitting elements has a similar feature; therefore, this electronic paper has high reliability and reduction in power consumption thereof is achieved.

Furthermore, such an electronic paper is extremely light and flexible and can be rolled into a cylinder shape as well; thus, the electronic paper is a display device that has a great advantage in terms of portability. The electronic device of the present invention allows a display medium having a large screen to be freely carried.

The electronic paper illustrated in FIG. 6E can be used as a display means of a navigation system, an audio reproducing device (such as a car audio or an audio component), a personal computer, a game machine, and a portable information terminal (such as a mobile computer, a cellular phone, a portable game machine, or an electronic book reader). In addition, the electronic paper illustrated in FIG. 6E can be used as a means for mainly displaying still images for electrical home appliances such as a refrigerator, a washing machine, a rice cooker, a fixed telephone, a vacuum cleaner, or a clinical thermometer; hanging advertisements in trains; and large-sized information displays such as arrival and departure boards in railroad stations and airports.

As described above, the applicable range of a light-emitting device of the present invention is wide, so that this light-emitting device can be applied to electronic devices of various fields. By using a carbazole derivative of the present invention, an electronic device having a display portion whose power consumption is reduced can be provided.

Moreover, a light-emitting device of the present invention can be used as a lighting device. One mode in which the light-emitting device of the present invention is used as a lighting device is described with reference to FIG. 7.

Figure 7:
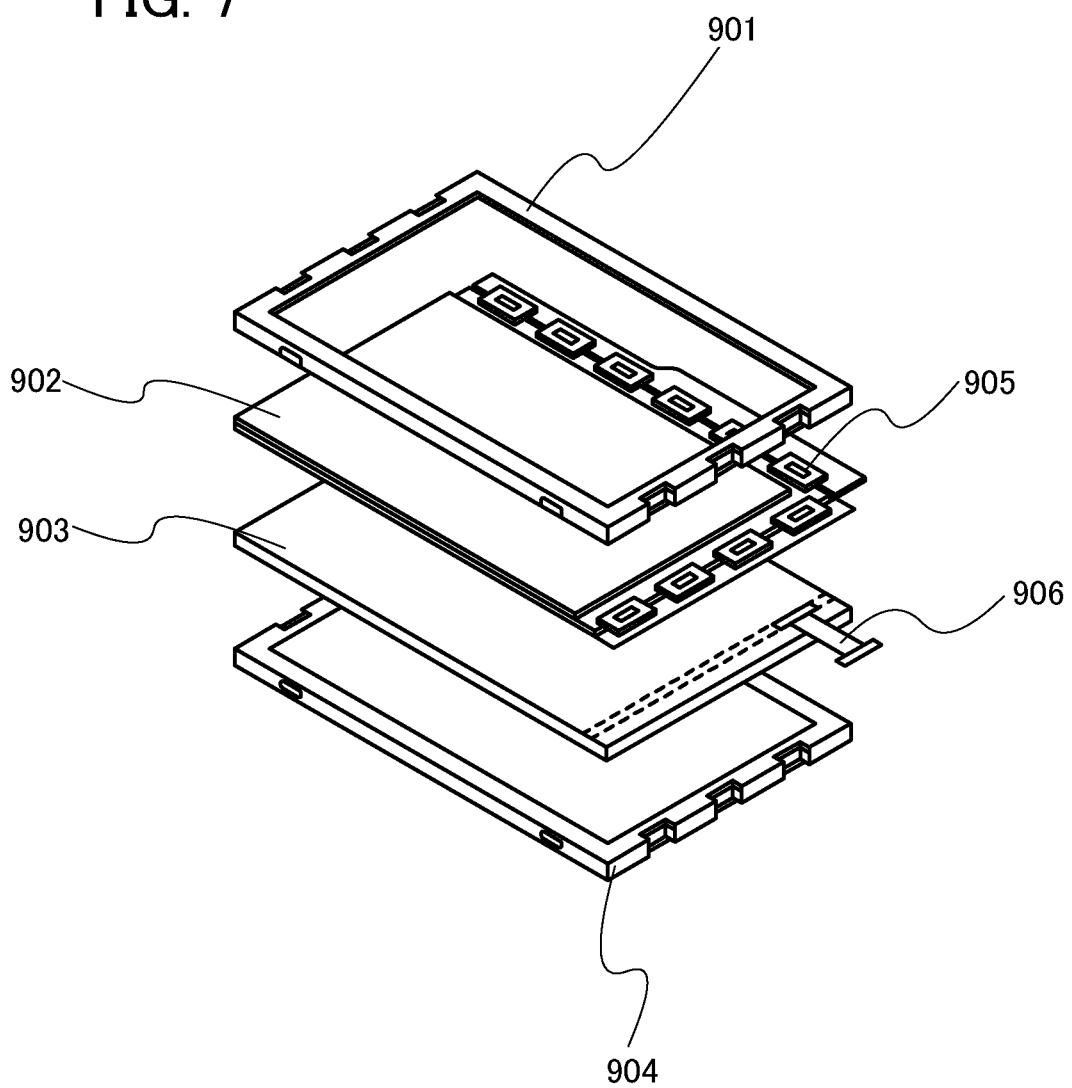
FIG. 7 is a view illustrating an electronic device.

FIG. 7 illustrates an example of a liquid crystal display device in which a light-emitting device of the present invention is used as a backlight. The liquid crystal display device illustrated in FIG. 7 includes a housing 901, a liquid crystal layer 902, a backlight 903, and a housing 904. The liquid crystal layer 902 is connected to a driver IC 905. The light-emitting device of the present invention is used for the backlight 903 to which current is supplied through a terminal 906.

By using a light-emitting device of the present invention for a backlight of a liquid crystal display device, a highly reliable backlight can be obtained. Further, a light-emitting device of the present invention can be applied to a lighting device of plane light emission and can have a large area. Therefore, the backlight can have a large area, and a liquid crystal display device having a large area can be obtained. Furthermore, since a light-emitting device of the present invention is thin, the thickness of a display device can also be reduced.

Figure 8A:
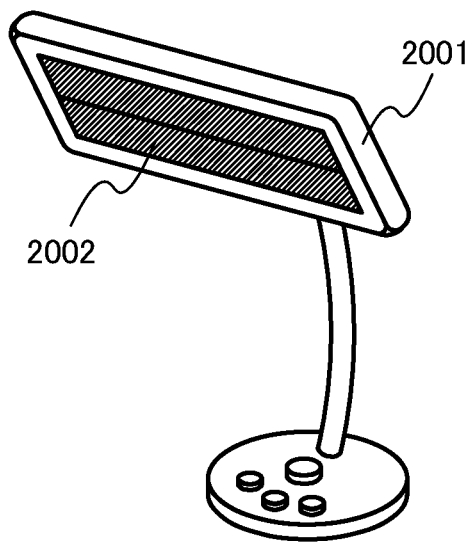
FIGS. 8A and 8B are views each illustrating a lighting device.
Figure 8B:
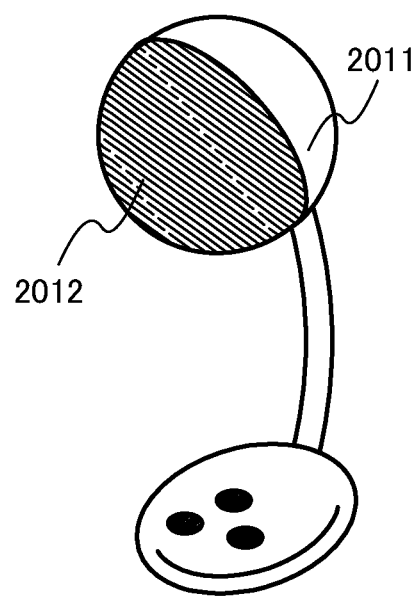

FIGS. 8A and 8B each illustrate an example in which a light-emitting device of the present invention is used as a table lamp, which is a kind of lighting device. The table lamp illustrated in FIG. 8A includes a housing 2001 and a light source 2002, and the table lamp illustrated in FIG. 8B includes a housing 2011 and a light source 2012. A light-emitting device of the present invention is used as the light source 2002 and the light source 2012. Since power consumption of the light-emitting device of the present invention is reduced, power consumption of the table lamp can also be reduced.

Figure 9:
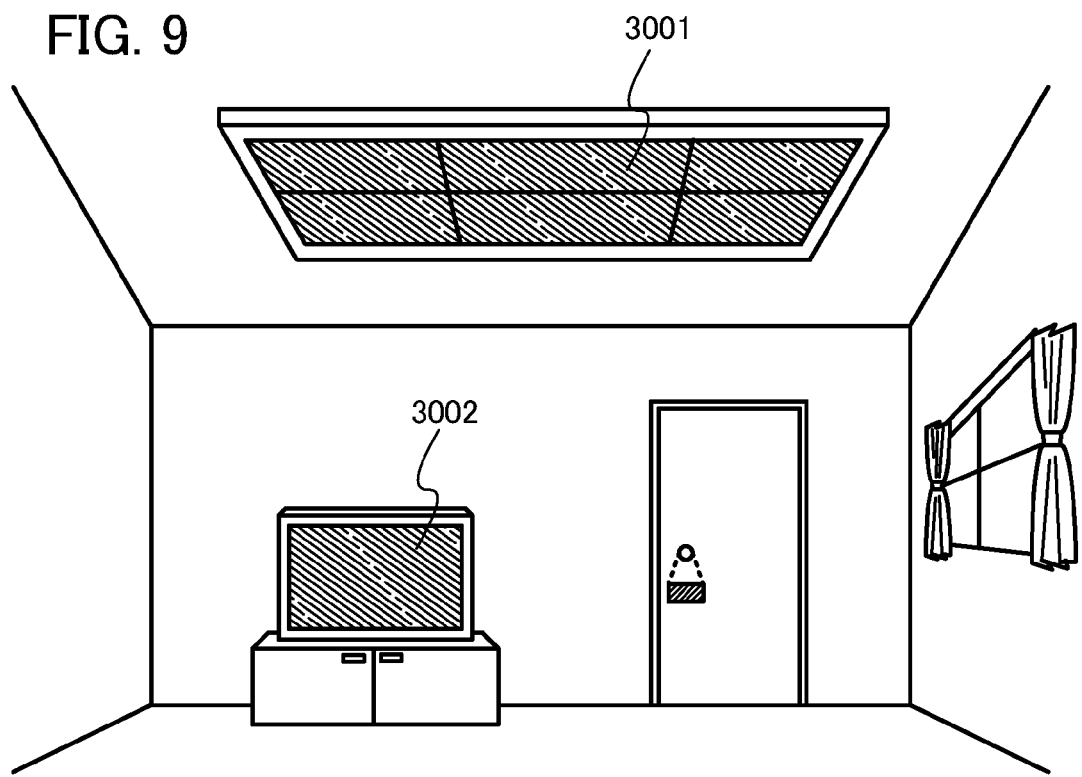
FIG. 9 is a view illustrating a lighting device.

FIG. 9 illustrates an example in which a light-emitting device of the present invention is used as an indoor lighting device 3001. Since the light-emitting device of the present invention can have a large area, the light-emitting device of the present invention can be used as a large-area lighting device. Further, since the light-emitting device of the present invention is thin, the light-emitting device of the present invention can be used as a lighting device having a reduced thickness. In a room where a light-emitting device to which the present invention is applied is used as the indoor lighting device 3001 in this manner, a television device 3002 according to the present invention, which is similar to the one illustrated in FIG. 6A, can be placed so that public broadcasting and movies can be watched.

EXAMPLE 1

In this example, a synthesis method of 4-(9H-carbazol-9-yl)-4'-(9-phenyl-9H-carbazol-3-yl)triphenylamine (abbreviation: PCBACzP), which is a carbazole derivative of the present invention and represented by the structural formula (100), will be specifically described.

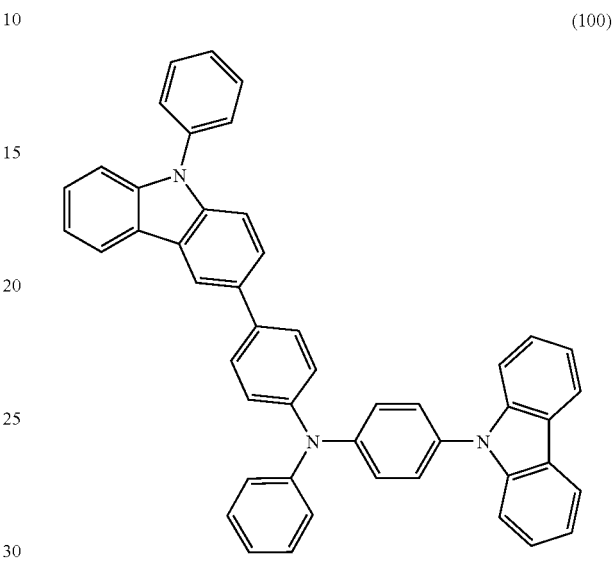

(100)

A synthesis scheme of PCBACzP is shown in (A-1).

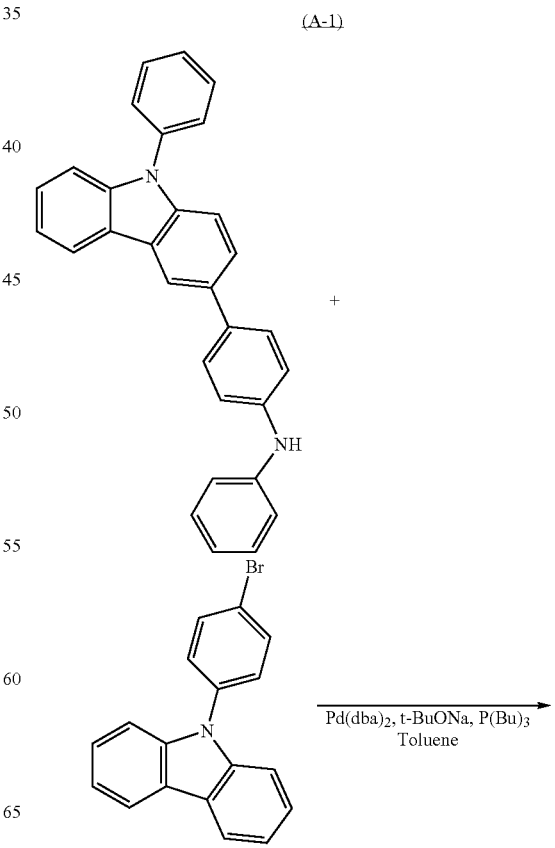

(A-1)

Pd(dba)$_2$, t-BuONa, P(Bu)$_3$
Toluene

-continued

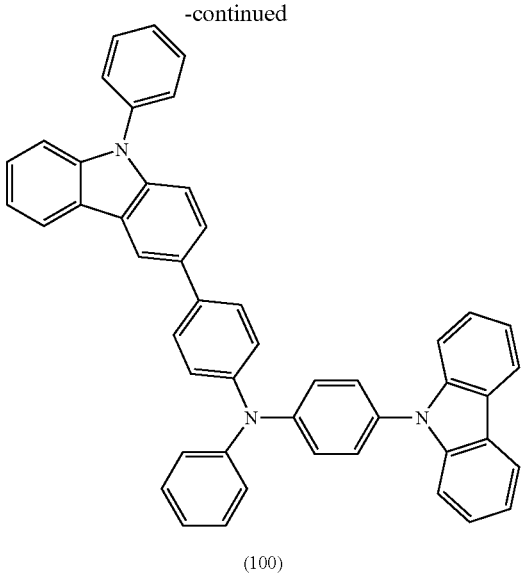

(100)

Into a 100 mL three-neck flask were put 2.0 g (4.9 mmol) of 4-(9-phenyl-9H-carbazol-3-yl)diphenylamine (PCBA), 1.6 g (4.9 mmol) of 9-(4-bromophenyl)-9H-carbazole, and 2.0 g (20 mmol) of sodium tert-butoxide, and the atmosphere in the flask was replaced with nitrogen. Then, 50 mL of toluene and 0.30 mL of tri(tert-butyl)phosphine (10 wt % hexane solution) were added to this mixture.

Under reduced pressure, this mixture was degassed while being stirred. After that, 0.10 g of bis(dibenzylideneacetone)palladium(0) was added to the mixture. This mixture was stirred while being heated at 80° C. for 5 hours to be reacted. After the reaction, toluene was added to the reaction mixture. This suspension was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135), whereby a filtrate was obtained. The obtained filtrate was washed with a saturated aqueous sodium hydrogen carbonate solution and a saturated aqueous sodium chloride solution. After the washing, magnesium sulfate was added to an organic layer to dry the organic layer. After the drying, this mixture was subjected to suction filtration to give a filtrate. The obtained filtrate was concentrated, and purified by silica gel column chromatography. The silica gel column chromatography was performed by, first, using a mixed solvent in which the ratio of toluene to hexane is 1:9 as a developing solvent, and then using a mixed solvent in which the ratio of toluene to hexane is 3:7 as another developing solvent. A solid which was obtained by concentrating the obtained fractions was recrystallized from a mixed solvent of chloroform and hexane to give 2.9 g of a powdered white solid in a yield of 91%.

Sublimation purification of 1.9 g of the obtained white solid was performed by a train sublimation method. The sublimation purification was performed under a reduced pressure of 7.0 Pa and with an argon flow rate of 4 mL/min, at 330° C. for 15 hours. Thus, 1.7 g of the white solid was obtained in a yield of 89%.

By nuclear magnetic resonance (NMR), the compound obtained by the above synthesis method was identified as 4-(9H-carbazol-9-yl)-4'-(9-phenyl-9H-carbazol-3-yl)triphenylamine (abbreviation: PCBACzP), which was the desired substance.

$^1$H NMR data of the obtained compound is shown below.
$^1$H NMR (CDCl$_3$, 300 MHz): δ=7.08-7.15 (m, 1H), 7.25-7.73 (m, 28H), 8.12-8.21 (m, 3H), 8.35 (s, 1H).

Figure 12A:
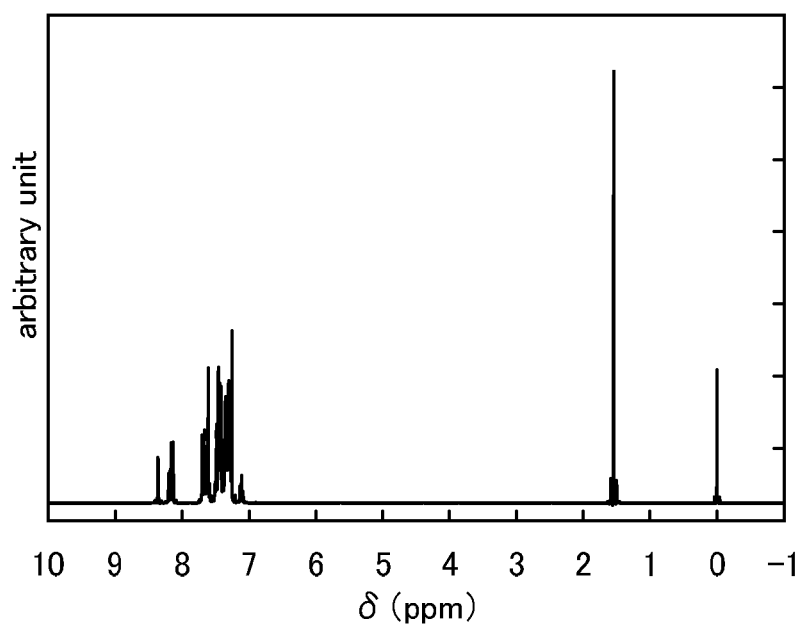
FIGS. 12A and 12B are graphs showing a $^1$H NMR chart of PCBACzP.
Figure 12B:
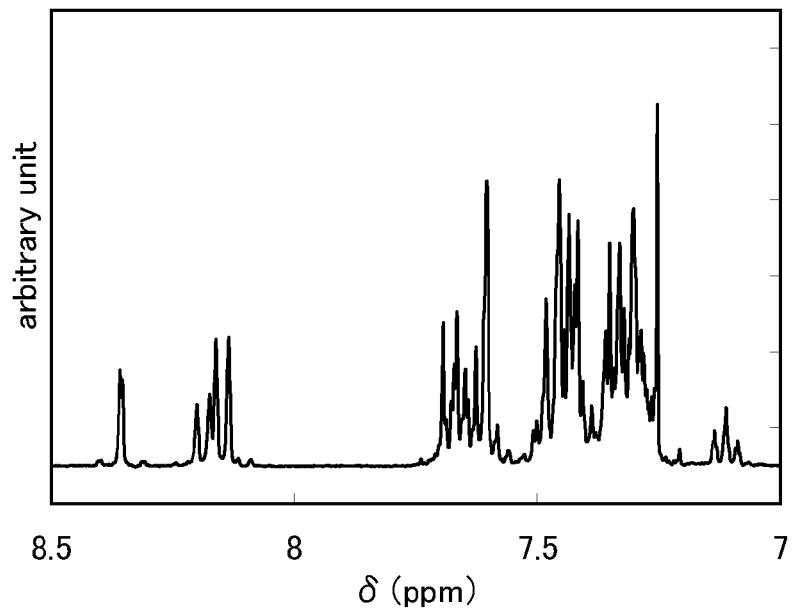

Further, the $^1$H NMR chart is illustrated in FIGS. 12A and 12B. Note that FIG. 12B is a chart showing an enlarged portion of FIG. 12A in the range of from 7.0 ppm to 8.5 ppm.

Figure 13:
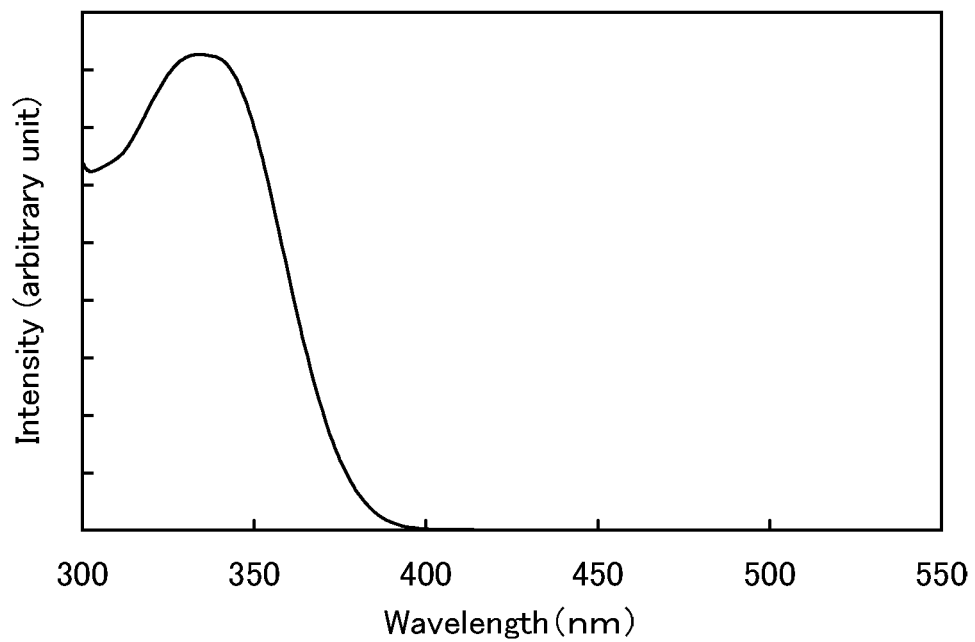
FIG. 13 is a graph showing an absorption spectrum of a toluene solution of PCBACzP.
Figure 14:
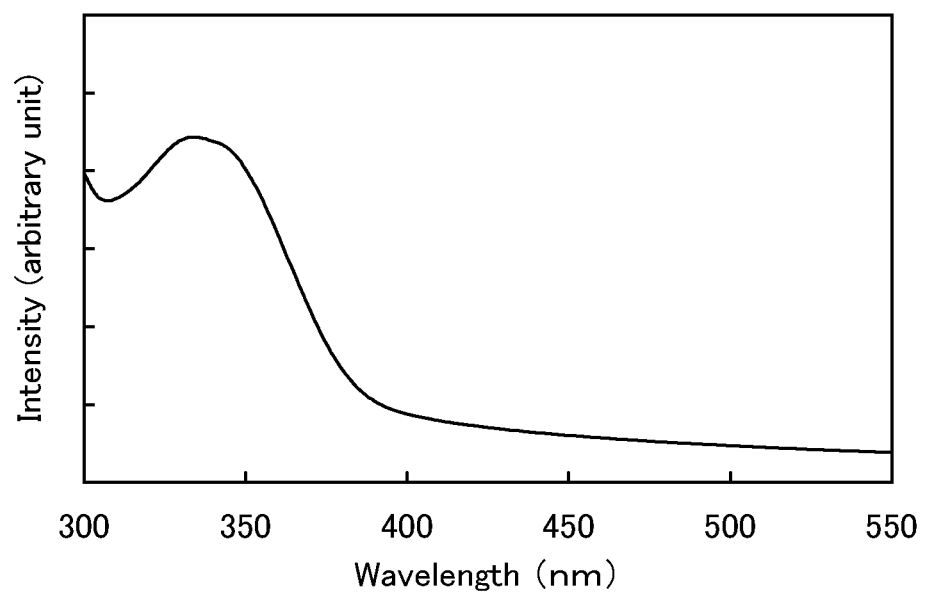
FIG. 14 is a graph showing an absorption spectrum of a thin film of PCBACzP.
Figure 15:
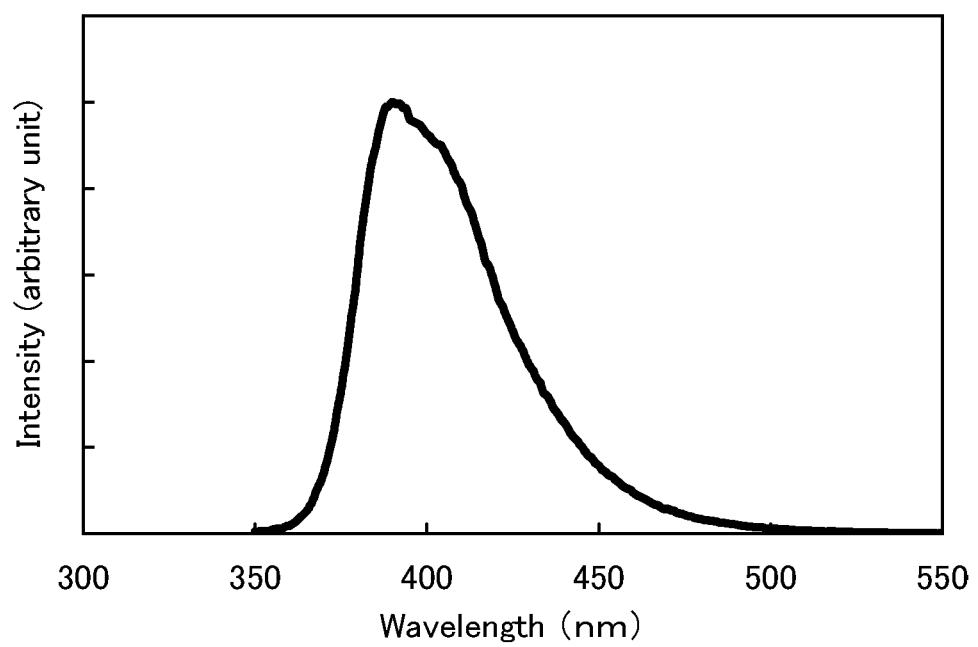
FIG. 15 is a graph showing an emission spectrum of the toluene solution of PCBACzP.
Figure 16:
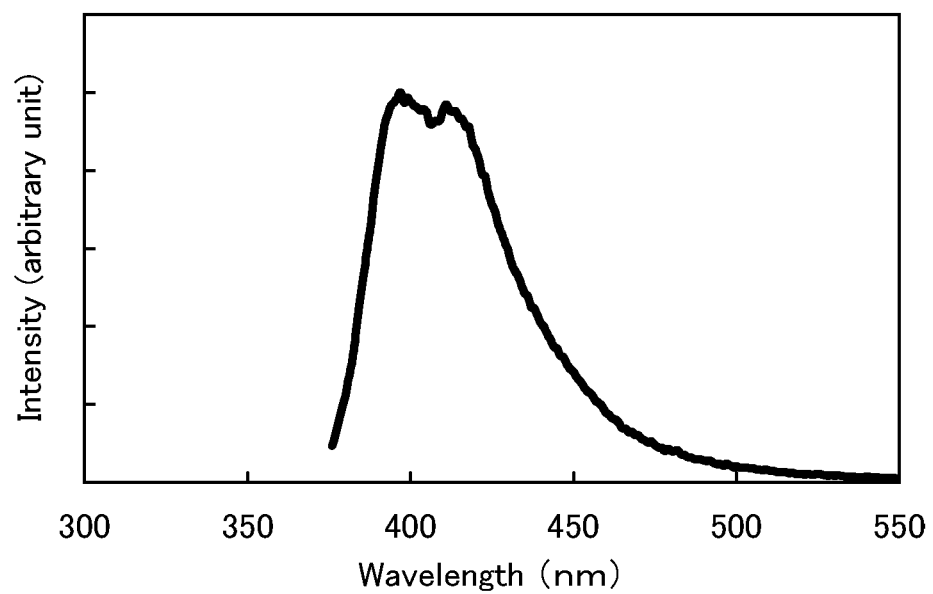
FIG. 16 is a graph showing an emission spectrum of the thin film of PCBACzP.

FIG. 13 and FIG. 15 show an absorption spectrum of a toluene solution of PCBACzP and an emission spectrum thereof, respectively. FIG. 14 and FIG. 16 show an absorption spectrum of a thin film of PCBACzP and an emission spectrum thereof, respectively. The measurement of the absorption spectrum was performed using an ultraviolet-visible spectrophotometer (V-550, manufactured by JASCO Corporation). In order to prepare samples, the solution was put to a quartz cell while the thin film was obtained by evaporation onto a quartz substrate. The absorption spectrum of the toluene solution of PCBACzP was obtained by subtracting the absorption spectra of quartz and toluene from the absorption spectrum of the toluene solution in a quartz cell, which is shown in FIG. 13. The absorption spectrum of the thin film of PCBACzP was obtained by subtracting that of the quartz substrate, which is shown in FIG. 14. In each of FIG. 13, FIG. 14, FIG. 15, and FIG. 16, the horizontal axis represents wavelength (nm) and the vertical axis represents absorption intensity (arbitrary unit). In the case of the toluene solution, absorption was observed at about 335 nm, and a maximum emission wavelength was 393 nm (excitation wavelength: 335 nm). Further, in the case of the thin film, absorption was observed at about 334 nm, and a maximum emission wavelength was 411 nm (excitation wavelength: 361 nm).

Further, the HOMO level and LUMO level of PCBACzP in a state of a thin film were measured. The value of the HOMO level was obtained by conversion of the value of the ionization potential measured with a photoelectron spectrometer (AC-2, manufactured by RJKEN KEIKI Co., Ltd.) in the atmosphere into a negative value. In addition, the value of the LUMO level was obtained in such a manner that the absorption edge was obtained from Tauc plot, with an assumption of direct transition, using data on the absorption spectrum of the thin film of PCBACzP which was shown in FIG. 14, and added as an optical energy gap to the value of the HOMO level. The results show that the HOMO level, energy gap, and LUMO level of PCBACzP are −5.44 eV, 3.30 eV, and −2.14 eV, respectively.

Further, the oxidation-reduction characteristics of PCBACzP were measured. The oxidation-reduction characteristics were measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Sigma-Aldrich Corp., 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to 1 mmol/L. A platinum electrode (manufactured by BAS Inc., PTE platinum electrode) was used as a working electrode, a platinum electrode (manufactured by BAS Inc., Pt counter electrode for VC-3, (5 cm))

was used as an auxiliary electrode, and an Ag/Ag+ electrode (manufactured by BAS Inc., RE-7 reference electrode for nonaqueous solvent) was used as a reference electrode. The measurement was carried out at room temperature.

The oxidation reaction characteristics of PCBACzP were measured as follows. A scan in which the potential of the working electrode with respect to the reference electrode was changed to 0.90 V from −0.075 V and then the potential was changed to −0.077 V from −0.90 V was set as one cycle, and 100 cycle measurements were performed. Note that the scanning speed of the CV measurement was set at 0.1 V/s.

The reduction reaction characteristics of PCBACzP were measured as follows. A scan in which the potential of the working electrode with respect to the reference electrode was changed to −3.00 V from −1.11 V and then the potential was changed to −1.11 V from −3.00 V was set as one cycle, and 100 cycle measurements were performed. Note that the scanning speed of the CV measurement was set at 0.1 V/s.

Figure 17:
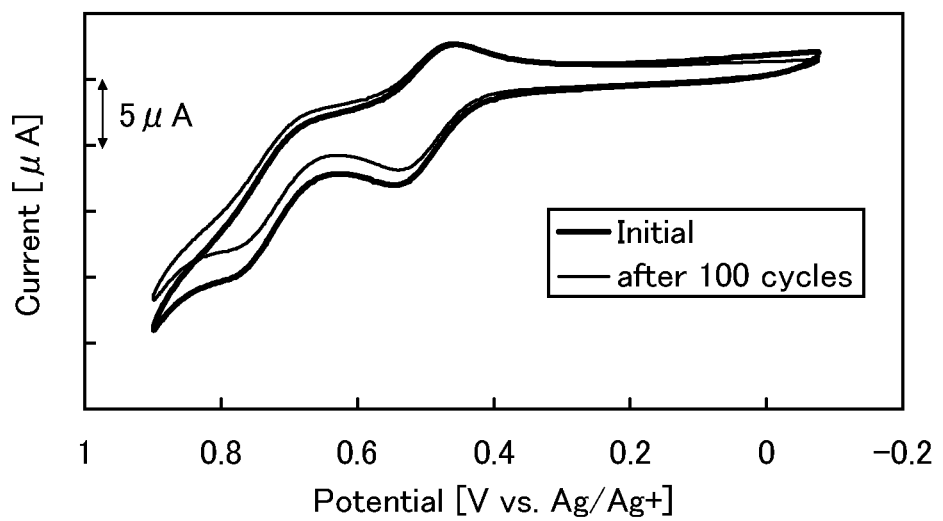
FIG. 17 is a graph showing CV measurement results of PCBACzP.
Figure 18:
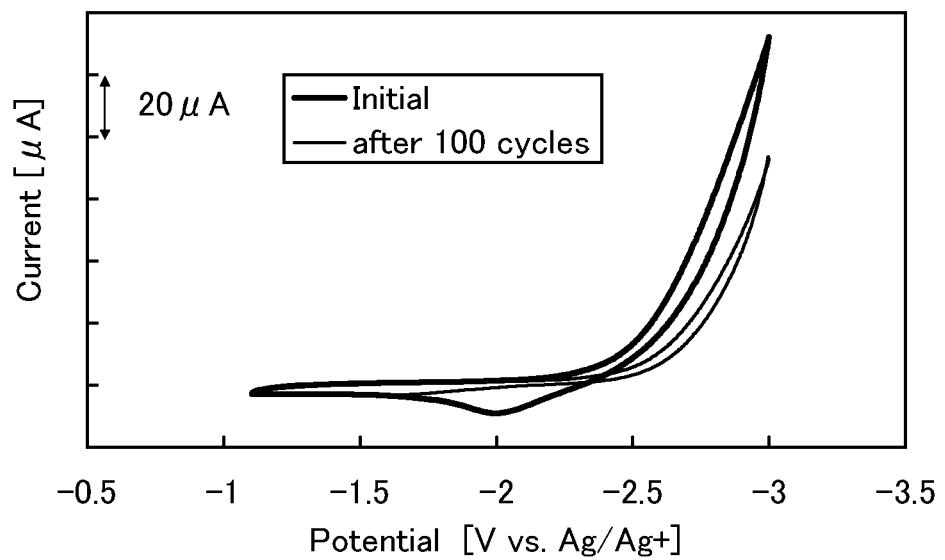
FIG. 18 is a graph showing CV measurement results of PCBACzP.

FIG. 17 shows CV measurement results on the oxidation reaction characteristics of PCBACzP and FIG. 18 shows CV measurement results on the reduction reaction characteristics thereof. In each of FIG. 17 and FIG. 18, the horizontal axis represents potential (V) of the working electrode with respect to the reference electrode, and the vertical axis represents value of a current (μA) flowing between the working electrode and the auxiliary electrode. According to FIG. 17, a current indicating oxidation was observed at around +0.54 V (vs. Ag/Ag+ electrode).

EXAMPLE 2

In this example, a synthesis method of 4-(9H-carbazol-9-yl)-4'-phenyl-4"-(9-phenyl-9H-carbazol-3-yl)triphenylamine (abbreviation: PCBBiCP), which is a carbazole derivative of the present invention and represented by the structural formula (123), will be specifically described.

(123)

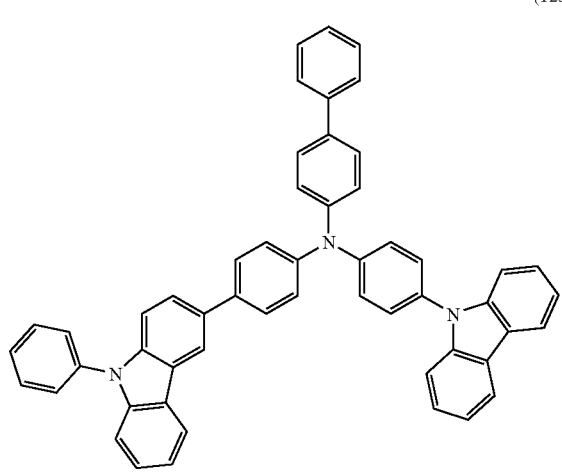

A synthesis scheme of PCBBiCP is shown in (B-1).

(B-1)

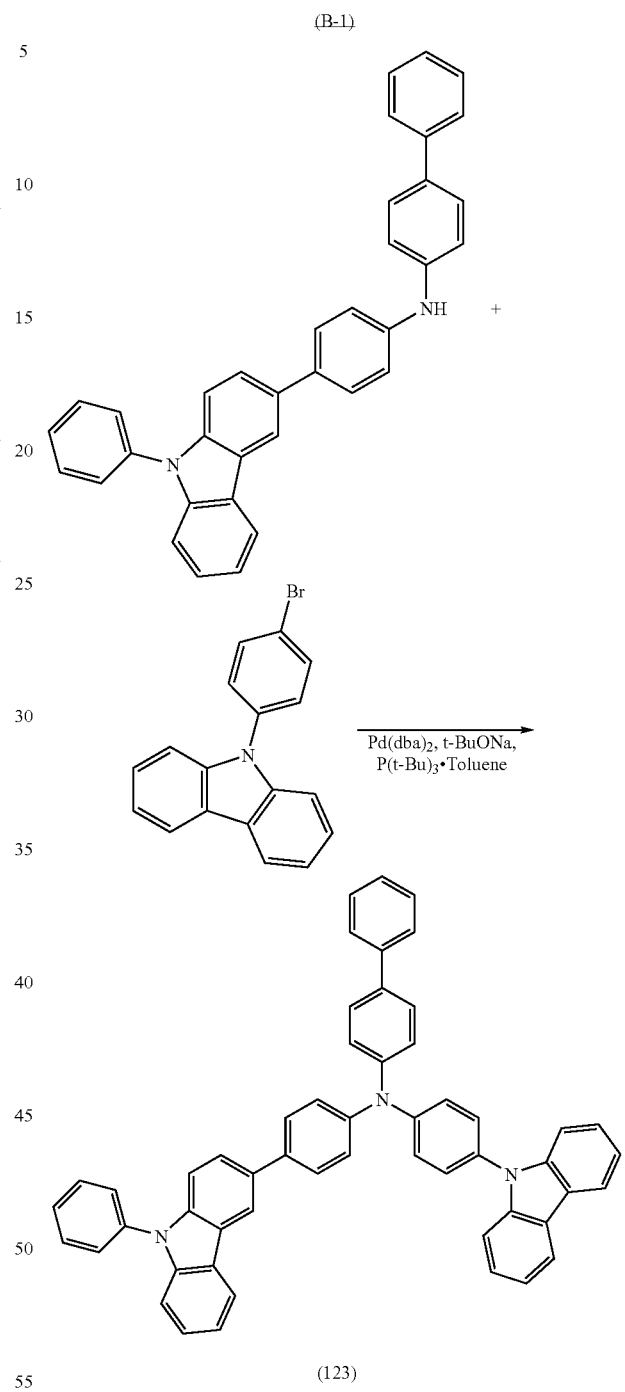

(123)

Into a 100 mL three-neck flask were put 2.0 g (4.1 mmol) of 4-phenyl-4'-(9-phenyl-9H-carbazol-3-yl)diphenylamine (PCBBi), 1.3 g (4.1 mmol) of N-(4-bromophenyl)carbazole, and 2.0 g (20 mmol) of sodium tert-butoxide, and the atmosphere in the flask was replaced with nitrogen. Then, 50 mL of toluene and 0.30 mL of tri(tert-butyl)phosphine (10 wt % hexane solution) were added to this mixture. Under reduced pressure, this mixture was degassed while being stirred. After that, 0.10 g of bis(dibenzylideneacetone)palladium(0) was added to the mixture. This mixture was stirred while being heated at 80° C. for 5 hours to be reacted. After the reaction, toluene was added to the reaction mixture. This suspension was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135), whereby a filtrate was obtained. The obtained filtrate was washed with a saturated aqueous sodium hydrogen carbonate solution and a saturated aqueous sodium chloride solution. After the washing, magnesium sulfate was added to an organic layer to dry the organic layer. After the drying, this mixture was subjected to suction filtration to give a filtrate. The obtained filtrate was concentrated, and purified by silica gel column chromatography. The silica gel column chromatography was performed by, first, using a mixed solvent in which the ratio of toluene to hexane is 1:9 as a developing solvent, and then using a mixed solvent in which the ratio of toluene to hexane is 3:7 as another developing solvent. A solid which was obtained by concentrating the obtained fractions was recrystallized from a mixed solvent of chloroform and hexane to give 2.1 g of a powdered white solid in a yield of 70%.

Sublimation purification of 1.0 g of the obtained white solid was performed by a train sublimation method. The sublimation purification was performed under a reduced pressure of 7.0 Pa and with an argon flow rate of 4 mL/min, at 350° C. for 15 hours. Thus, 0.85 g of the white solid was obtained in a yield of 85%.

By nuclear magnetic resonance (NMR), the compound obtained by the above synthesis method was identified as 4-(9H-carbazol-9-yl)-4'-phenyl-4"-(9-phenyl-9H-carbazol-3-yl)triphenylamine (abbreviation: PCBBiCP), which was the desired substance.

$^1$H NMR data of the obtained compound is shown below.
$^1$H NMR (CDCl$_3$, 300 MHz): δ=7.26-7.75 (m, 33H), 8.13-8.23 (m, 3H), 8.37 (m, 1H).

Figure 19A:
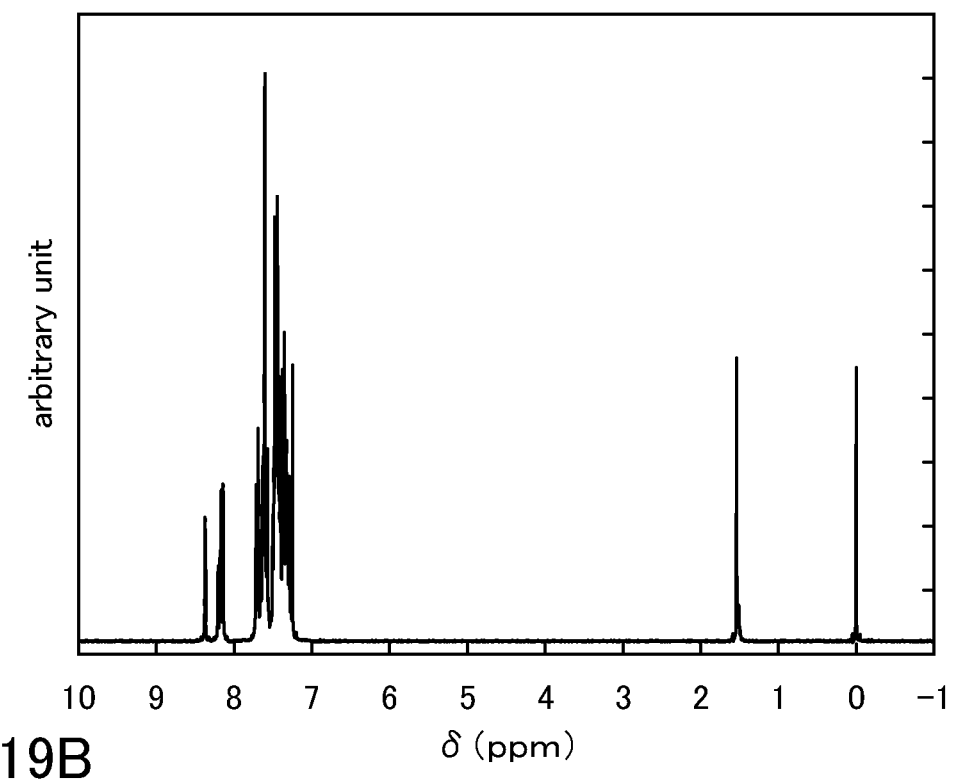
FIGS. 19A and 19B are graphs showing a $^1$H NMR chart of PCBBiCP.
Figure 19B:
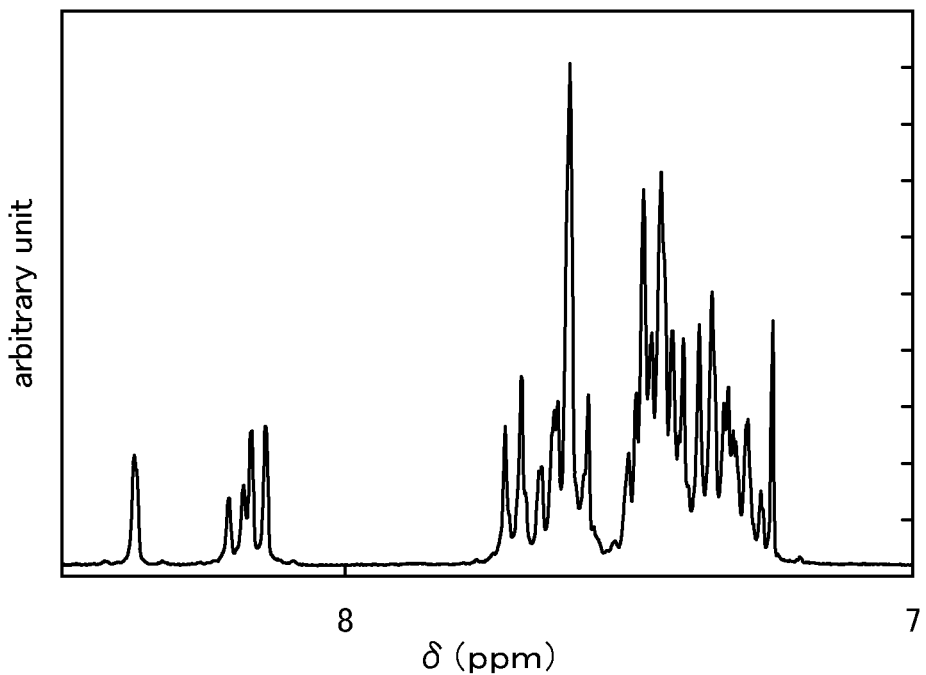

Further, the $^1$H NMR chart is illustrated in FIGS. 19A and 19B. Note that FIG. 19B is a chart showing an enlarged portion of FIG. 19A in the range of from 7.0 ppm to 8.5 ppm.

Figure 20:
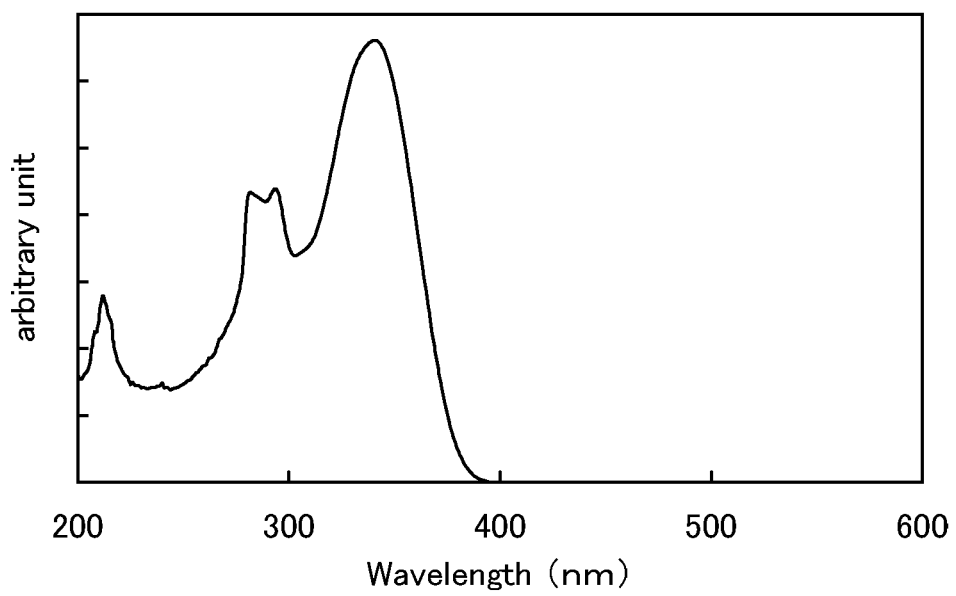
FIG. 20 is a graph showing an emission spectrum of a toluene solution of PCBBiCP.
Figure 21:
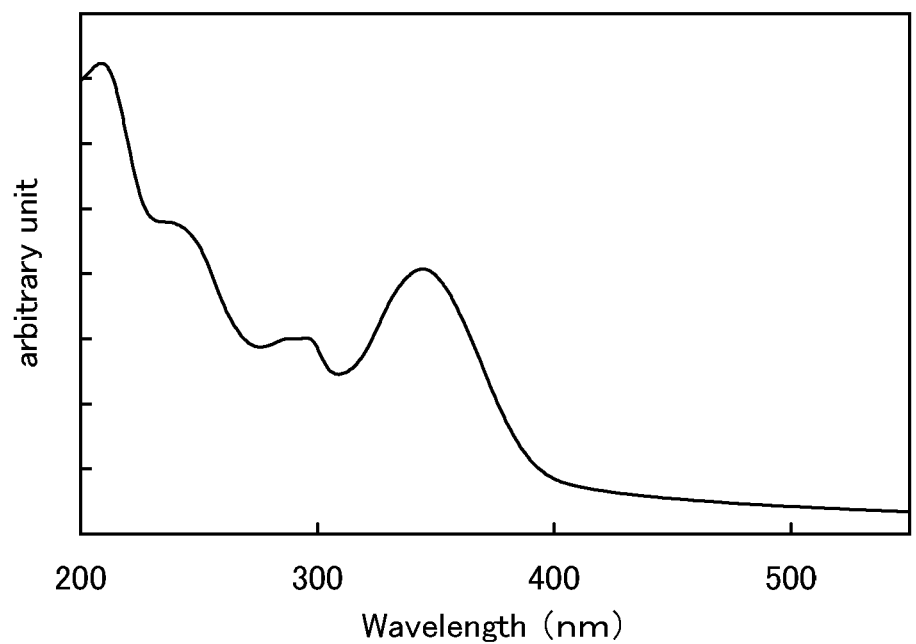
FIG. 21 is a graph showing an emission spectrum of a thin film of PCBBiCP.
Figure 22:
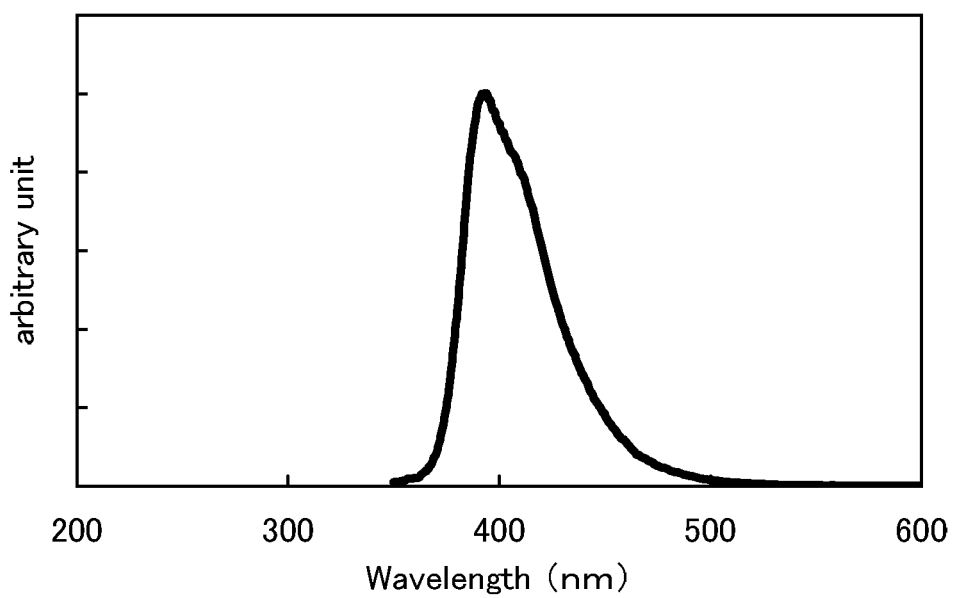
FIG. 22 is a graph showing an emission spectrum of the toluene solution of PCBBiCP.
Figure 23:
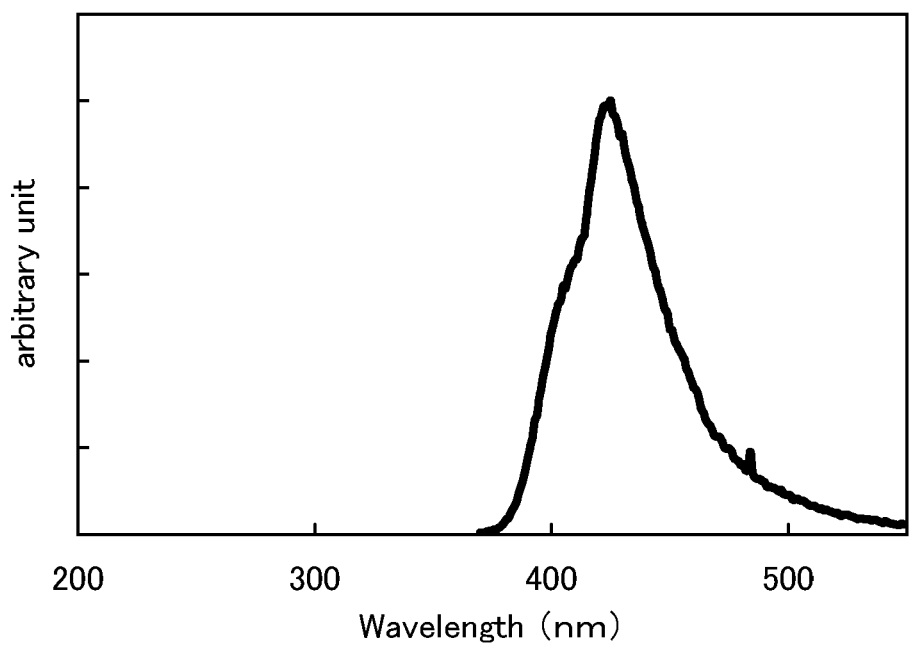
FIG. 23 is a graph showing an emission spectrum of the thin film of PCBBiCP.

FIG. 20 and FIG. 22 show an absorption spectrum of a toluene solution of PCBBiCP and an emission spectrum thereof, respectively. FIG. 21 and FIG. 23 show an absorption spectrum of a thin film of PCBBiCP and an emission spectrum thereof, respectively. The measurement of the absorption spectrum was performed using an ultraviolet-visible spectrophotometer (V-550, manufactured by JASCO Corporation). In order to prepare samples, the solution was put to a quartz cell while the thin film was obtained by evaporation onto a quartz substrate. The absorption spectrum of the toluene solution of PCBBiCP was obtained by subtracting the absorption spectra of quartz and toluene from the absorption spectrum of the toluene solution in a quartz cell, which is shown in FIG. 20. The absorption spectrum of the thin film of PCBBiCP was obtained by subtracting that of the quartz substrate, which is shown in FIG. 21. In each of FIG. 20, FIG. 21, FIG. 22, and FIG. 23, the horizontal axis represents wavelength (nm) and the vertical axis represents absorption intensity (arbitrary unit). In the case of the toluene solution, absorption was observed at about 338 nm, and a maximum emission wavelength was 394 nm (excitation wavelength: 338 nm). Further, in the case of the thin film, absorption was observed at about 345 nm, and a maximum emission wavelength was 424 nm (excitation wavelength: 353 nm).

Further, the HOMO level and LUMO level of PCBBiCP in a state of a thin film were measured. The value of the HOMO level was obtained by conversion of the value of the ionization potential measured with a photoelectron spectrometer (AC-2, manufactured by RIKEN KEIKI Co., Ltd.) in the atmosphere into a negative value. In addition, the value of the LUMO level was obtained in such a manner that the absorption edge was obtained from Tauc plot, with an assumption of direct transition, using data on the absorption spectrum of the thin film of PCBBiCP which was shown in FIG. 21, and added as an optical energy gap to the value of the HOMO level. The results show that the HOMO level, energy gap, and LUMO level of PCBBiCP are −5.41 eV, 3.23 eV, and −2.18 eV, respectively.

Further, the oxidation-reduction characteristics of PCBBiCP were measured. The oxidation-reduction characteristics were measured by cyclic voltammetry (CV) measurement. Further, an electrochemical analyzer (ALS model 600A, manufactured by BAS Inc.) was used for the measurement.

As for a solution used in the CV measurement, dehydrated dimethylformamide (DMF, manufactured by Sigma-Aldrich Corp., 99.8%, catalog number: 22705-6) was used as a solvent. Tetra-n-butylammonium perchlorate (n-Bu$_4$NClO$_4$, manufactured by Tokyo Chemical Industry Co., Ltd., catalog number: T0836), which was a supporting electrolyte, was dissolved in the solvent such that the concentration of the tetra-n-butylammonium perchlorate was 100 mmol/L. Moreover, the object to be measured was dissolved such that the concentration thereof was set to 1 mmol/L. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was carried out at room temperature.

The oxidation reaction characteristics of PCBBiCP were measured as follows. A scan in which the potential of the working electrode with respect to the reference electrode was changed to 1.00 V from −0.029 V and then the potential was changed to −0.031 V from 1.00 V was set as one cycle, and 100 cycle measurements were performed. Note that the scanning speed of the CV measurement was set at 0.1 V/s.

The reduction reaction characteristics of PCBBiCP were measured as follows. A scan in which the potential of the working electrode with respect to the reference electrode was changed to −3.00 V from −1.02 V and then the potential was changed to −1.02 V from −3.00 V was set as one cycle, and 100 cycle measurements were performed. Note that the scanning speed of the CV measurement was set at 0.1 V/s.

Figure 24:
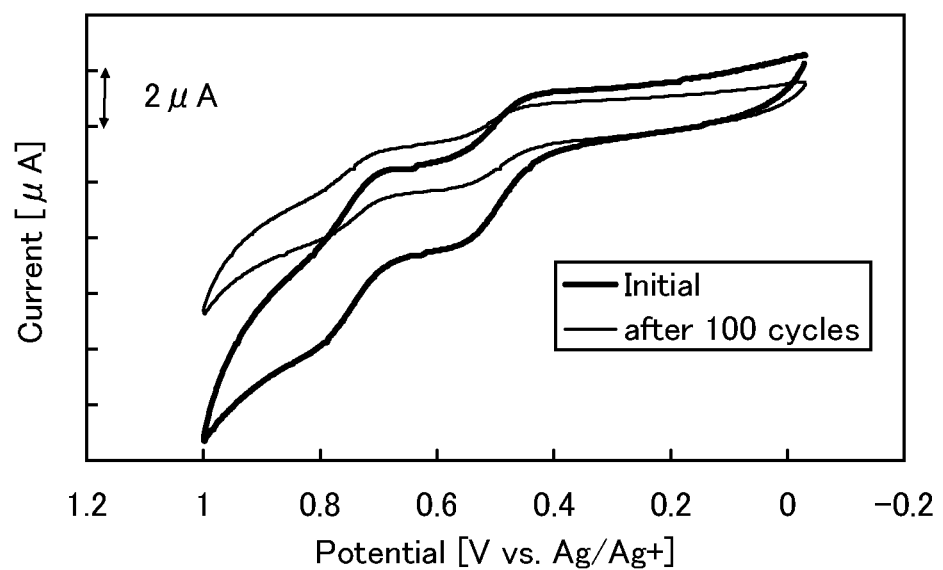
FIG. 24 is a graph showing CV measurement results of PCBBiCP.
Figure 25:
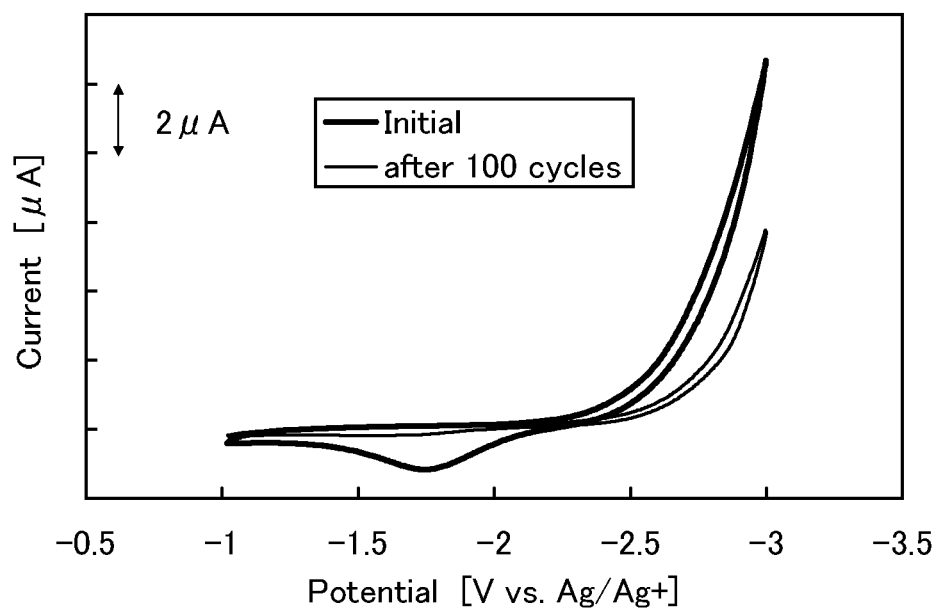
FIG. 25 is a graph showing CV measurement results of PCBBiCP.

FIG. 24 shows CV measurement results on the oxidation reaction characteristics of PCBBiCP and FIG. 25 shows CV measurement results on the reduction reaction characteristics thereof. In each of FIG. 24 and FIG. 25, the horizontal axis represents potential (V) of the working electrode with respect to the reference electrode, and the vertical axis represents value of a current (μA) flowing between the working electrode and the auxiliary electrode. According to FIG. 24, a current indicating oxidation was observed at around +0.56 V (vs. Ag/Ag$^+$ electrode).

EXAMPLE 3

Figure 10:
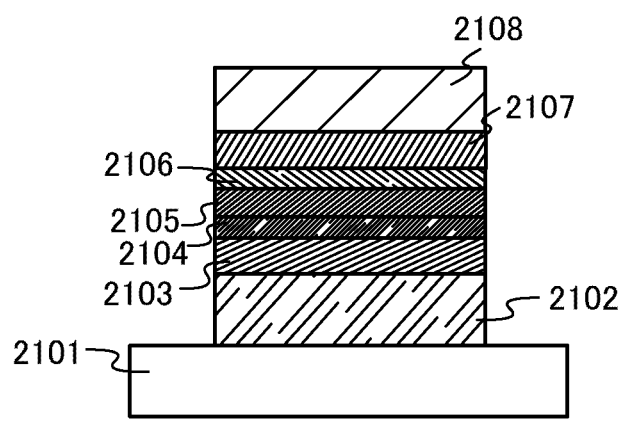
FIG. 10 is a view illustrating a light-emitting element of Example 3.

In this example, a light-emitting element of one embodiment of the present invention will be described with reference to FIG. 10.

The element structures of a comparative light-emitting element, a light-emitting element 1, and a light-emitting element 2 which were manufactured in this example are shown in Table 1. In Table 1, the mixture ratios are all represented in weight ratios.

TABLE 1

| | first electrode 2102 | first layer 2103 | second layer 2104 | third layer 2105 |
|---|---|---|---|---|
| comparative light-emitting element | ITSO 110 nm | NPB:MoOx(=4:1) 50 nm | NPB 10 nm | CzPA: PCBAPA (=1:0.1) 30 nm |
| light-emitting element 1 | ITSO 110 nm | NPB:MoOx(=4:1) 50 nm | PCBACzP 10 nm | CzPA: PCBAPA (=1:0.1) 30 nm |
| light-emitting element 2 | ITSO 110 nm | NPB:MoOx(=4:1) 50 nm | PCBBiCP 10 nm | CzPA: PCBAPA (=1:0.1) 30 nm |

| | fourth layer 2106 | fifth layer 2107 | second electrode 2108 | |
|---|---|---|---|---|
| comparative light-emitting element | Alq 10 nm | Bphen 20 nm | LiF 1 nm | Al 200 nm |
| light-emitting element 1 | Alq 10 nm | Bphen 20 nm | LiF 1 nm | Al 200 nm |
| light-emitting element 2 | Alq 10 nm | Bphen 20 nm | LiF 1 nm | Al 200 nm |

*mixture ratios are all represented in weight ratios.

Methods for manufacturing light-emitting elements of this example are described below.

In the formation of each of the comparative light-emitting element, the light-emitting element 1, and the light-emitting element 2, indium tin oxide containing silicon oxide (ITSO) was deposited over a glass substrate 2101 by a sputtering method, whereby a first electrode 2102 was formed. The thickness of the first electrode 2102 was 110 nm and the electrode area was 2 mm×2 mm.

Next, the substrate over which the first electrode was formed was fixed to a substrate holder provided in a vacuum evaporation apparatus so that a surface of the substrate on which the first electrode was formed faced downward. The pressure was reduced to about $10^{-4}$ Pa, and then 4,4'-bis[N-(1-naphthyl)-N-phenylamino]biphenyl (abbreviation: NPB) and molybdenum(VI) oxide were co-evaporated on the first electrode 2102, whereby a layer containing a composite material of an organic compound and an inorganic compound was formed as a first layer 2103. The thickness of the first layer 2103 was 50 nm and the weight ratio of NPB to molybdenum(VI) oxide was adjusted to be 4:1 (=NPB:molybdenum oxide). Note that co-evaporation is an evaporation method in which evaporation is performed at the same time from a plurality of evaporation sources in one treatment chamber.

Next, as for the comparative light-emitting element used as a comparative example, NPB was evaporated to a thickness of 10 nm, whereby a second layer 2104 was formed as a hole-transporting layer.

As for the light-emitting element 1, PCBACzP synthesized in Example 1 was evaporated to a thickness of 10 nm, whereby a second layer 2104 was formed as a hole-transporting layer.

As for the light-emitting element 2, PCBBiCP, which was synthesized in Example 2, was evaporated to a thickness of 10 nm, whereby a second layer 2104 was formed as a hole-transporting layer.

Next, in the formation of each of the comparative light-emitting element, the light-emitting element 1, and the light-emitting element 2, CzPA and 4-(10-phenyl-9-anthryl)-4'-(9-phenyl-9H-carbazol-3-yl)triphenylamine (abbreviation: PCBAPA) were co-evaporated onto the second layer 2104 so that the weight ratio of CzPA to PCBAPA was 1:0.1 (=CzPA: PCBAPA), whereby a third layer 2105 was formed as a light-emitting layer. The thickness of the third layer 2105 was 30 nm.

Next, in the formation of each of the comparative light-emitting element, the light-emitting element 1, and the light-emitting element 2, Alq was evaporated onto the third layer 2105 to a thickness of 10 nm, and then Bphen was evaporated to a thickness of 20 nm to form a stacked layer, whereby a fourth layer 2106 was formed as an electron-transporting layer. Further, lithium fluoride (LiF) was evaporated onto the fourth layer 2106 to a thickness of 1 nm, whereby a fifth layer 2107 was formed as an electron-injecting layer. Lastly, aluminum was evaporated to a thickness of 200 nm as a second electrode 2108 which functions as a cathode. Accordingly, the comparative light-emitting element, the light-emitting element 1, and the light-emitting element 2 of this example were obtained. Note that in all of the above evaporation steps, a resistance heating method was used. In addition, structural formulae of NPB, CzPA, PCBAPA, Alq, and Bphen are shown below.

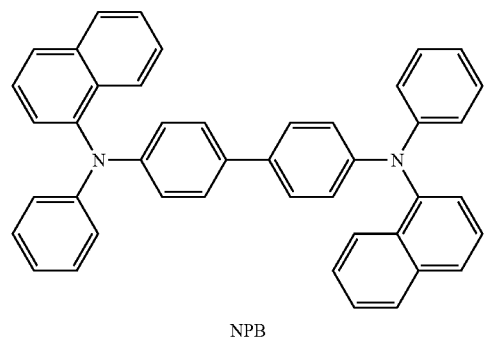

NPB

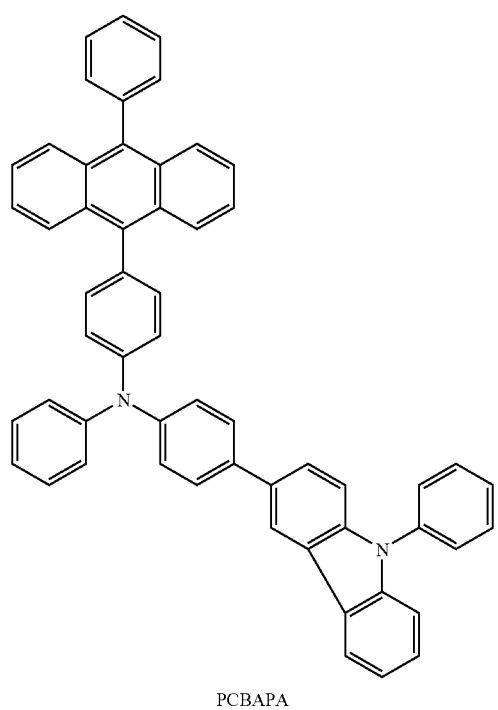 [SMILES: c1ccc(-c2c3ccccc3c(-c3ccc(N(c4ccccc4)c4ccc(-c5ccc6c(c5)c5ccccc5n6-c5ccccc5)cc4)cc3)c3ccccc23)cc1]

PCBAPA

-continued

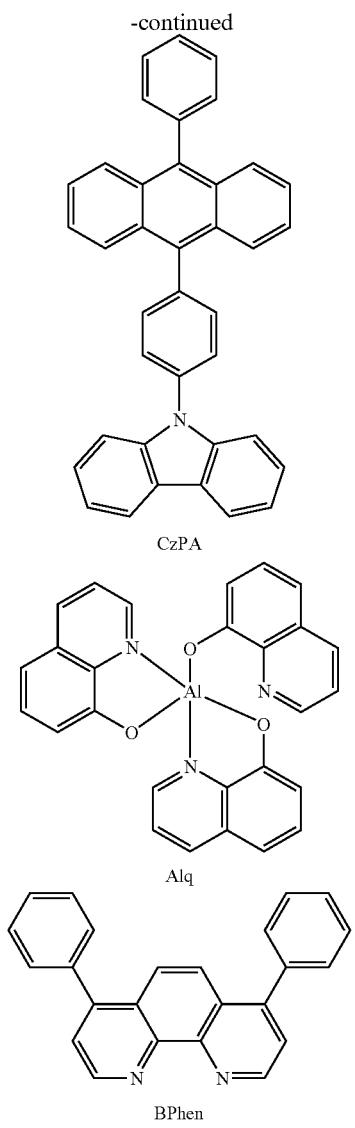

CzPA

Alq

BPhen

The comparative light-emitting element, the light-emitting element 1, and the light-emitting element 2 obtained in the above manner were sealed in a glove box under a nitrogen atmosphere without being exposed to the atmosphere. After that, the operating characteristics of the comparative light-emitting element, the light-emitting element 1, and the light-emitting element 2 were measured. The measurement was performed at room temperature (in the atmosphere in which the temperature was kept at 25° C.).

Figure 26:
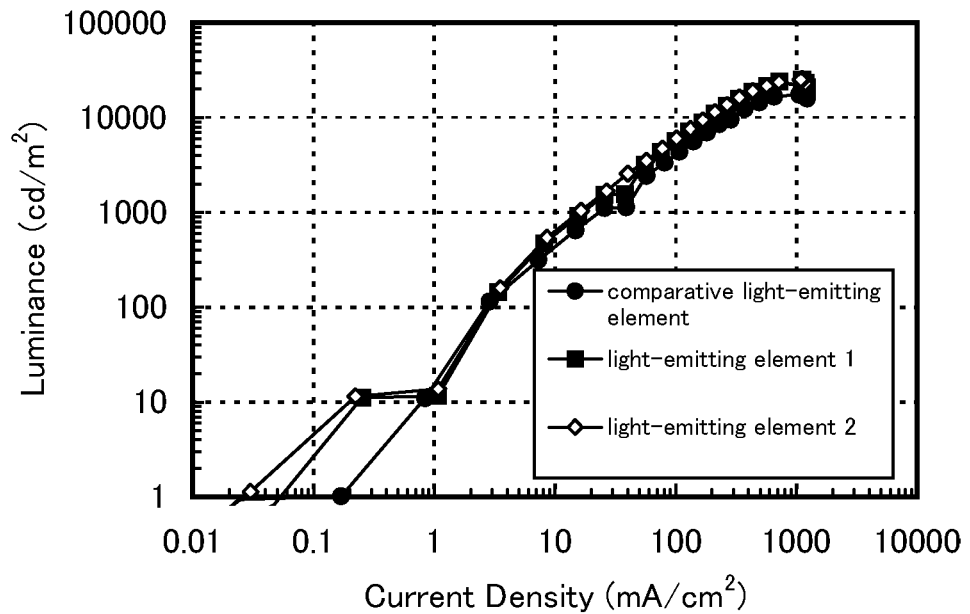
FIG. 26 is a graph showing the current density-luminance characteristics of a comparative light-emitting element, a light-emitting element 1, and a light-emitting element 2.
Figure 27:
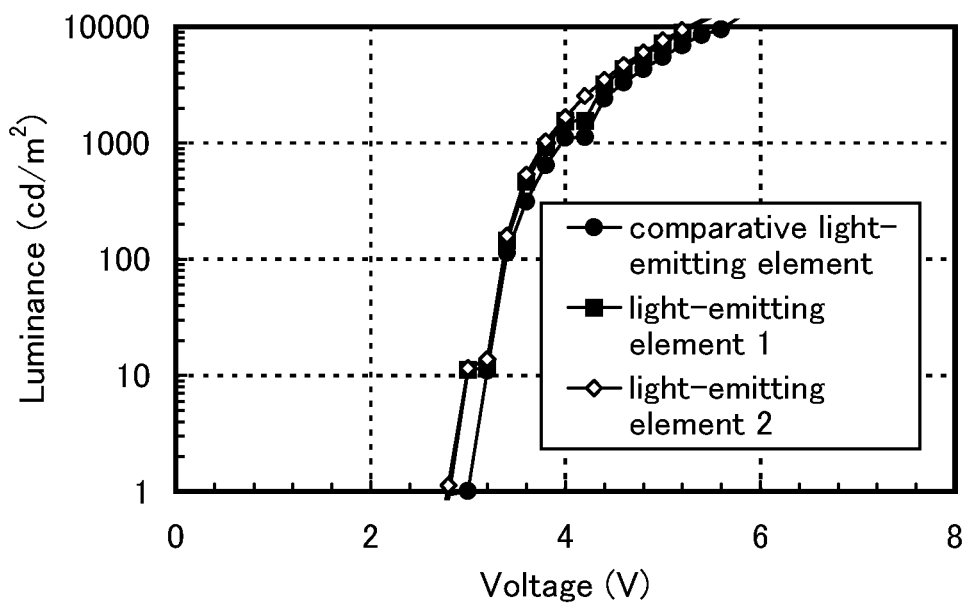
FIG. 27 is a graph showing the voltage-luminance characteristics of the comparative light-emitting element, the light-emitting element 1, and the light-emitting element 2.
Figure 28:
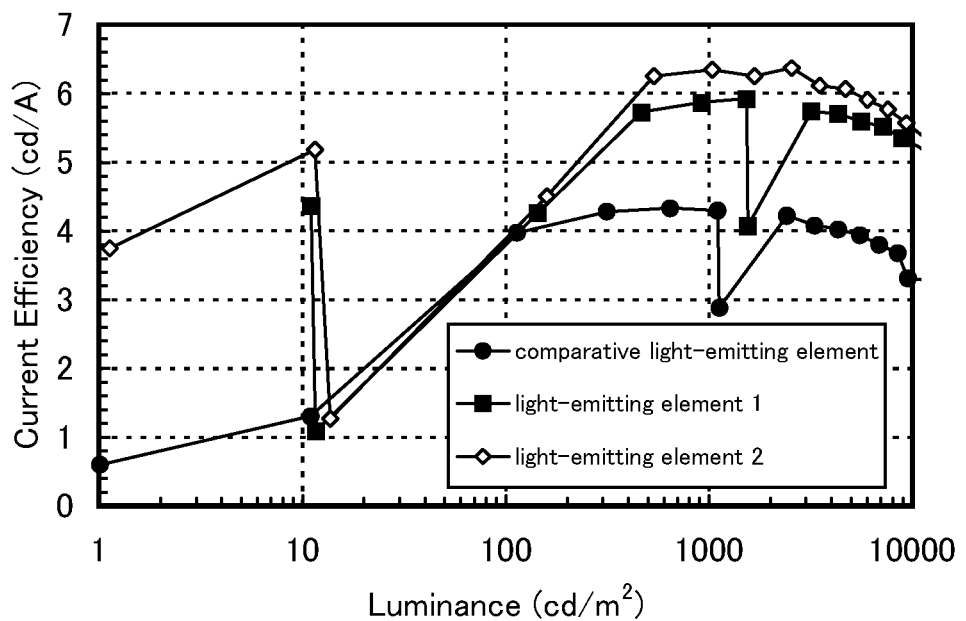
FIG. 28 is a graph showing the luminance-current efficiency characteristics of the comparative light-emitting element, the light-emitting element 1, and the light-emitting element 2.
Figure 29:
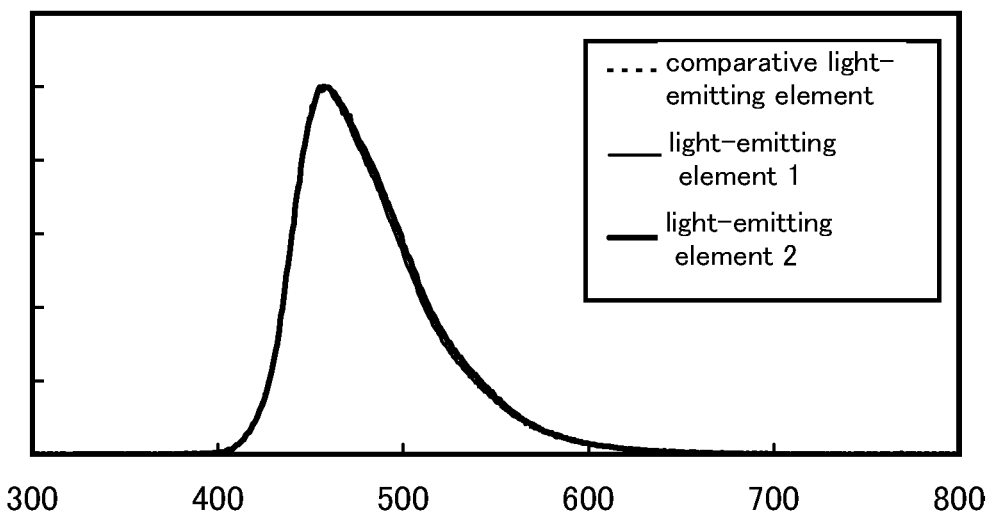
FIG. 29 is a graph showing emission spectra of the comparative light-emitting element, the light-emitting element 1, and the light-emitting element 2.

FIG. 26 shows the current density-luminance characteristics of the light-emitting elements, FIG. 27 shows the voltage-luminance characteristics thereof, and FIG. 28 shows the luminance-current efficiency characteristics thereof. In addition, FIG. 29 shows the emission spectrum at a current of 1 mA. According to FIG. 29, it was found that favorable blue light emission of PCBAPA having a peak at around 457 nm was obtained from each of the comparative light-emitting element, the light-emitting element 1, and the light-emitting element 2.

The comparative light-emitting element provided blue light emission where the CIE chromaticity coordinates were (x=0.15, y=0.17) when the luminance was 1106 cd/m$^2$. Further, the current efficiency, external quantum efficiency, voltage, current density, and power efficiency at a luminance of 1106 cd/m$^2$ were 4.29 cd/A, 3.2%, 4.0 V, 25.8 mA/cm$^2$, and 3.37 lm/W, respectively.

The light-emitting element 1 provided favorable blue light emission where the CIE chromaticity coordinates were (x=0.15, y=0.17) when the luminance was 916 cd/m$^2$. Further, the current efficiency, external quantum efficiency, voltage, current density, and power efficiency at a luminance of 916 cd/m$^2$ were 5.87 cd/A, 4.4%, 3.8 V, 15.6 mA/cm$^2$, and 4.85 lm/W, respectively.

The light-emitting element 2 provided favorable blue light emission where the CIE chromaticity coordinates were (x=0.15, y=0.17) when the luminance was 1037 cd/m$^2$. Further, the current efficiency, external quantum efficiency, voltage, current density, and power efficiency at a luminance of 1037 cd/m$^2$ were 6.34 cd/A, 4.6%, 3.8 V, 16.4 mA/cm$^2$, and 5.24 μm/W, respectively.

The light-emitting element 1 was formed using PCBACzP, which is one embodiment of the present invention, for the hole-transporting layer, and the light-emitting element 2 was formed using PCBBiCP, which is one embodiment of the present invention, for the hole-transporting layer. It can be seen that these light-emitting elements each have improved light emission efficiency as compared with the comparative light-emitting element used as a comparative example.

It was confirmed that one embodiment of the light-emitting element of the present invention had characteristics as a light-emitting element with high light emission efficiency and fully functioned.

EXAMPLE 4

Since 4-(10-phenyl-9-anthryl)-4'-(9-phenyl-9H-carbazol-3-yl)triphenylamine (abbreviation: PCBAPA), which is used in Example 3, is a novel substance, a synthesis method thereof is described below.

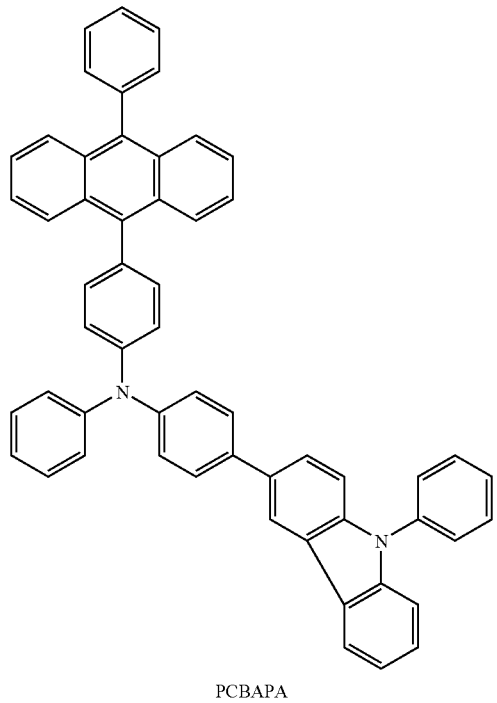

PCBAPA

A synthesis scheme of PCBAPA is shown in the following (X-1).

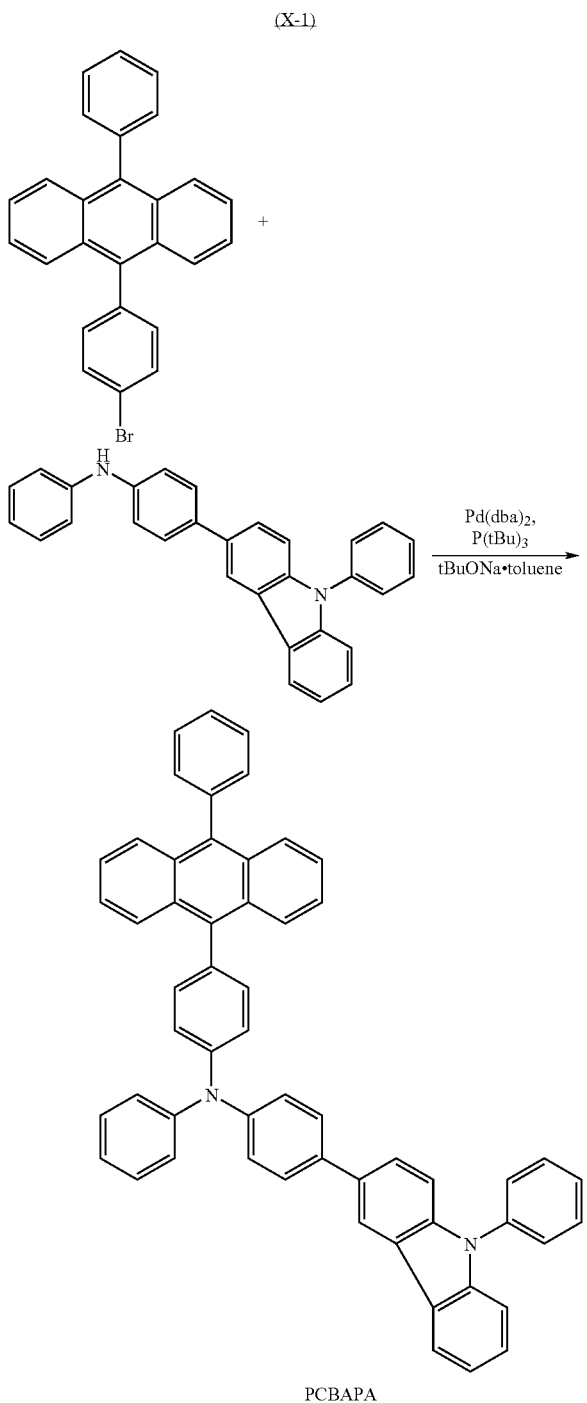

Into a 300 mL three-neck flask were put 7.8 g (12 mmol) of 9-(4-bromophenyl)-10-phenylanthracene, 4.8 g (12 mmol) of PCBA, and 5.2 g (52 mmol) of sodium tert-butoxide, and the atmosphere in the flask was replaced with nitrogen. To the mixture were added 60 mL of toluene and 0.30 mL of tri(tert-butyl)phosphine (10 wt % hexane solution). Then, 60 mL of toluene and 0.30 mL of tri(tert-butyl)phosphine (10 wt % hexane solution) were added to this mixture. Under reduced pressure, this mixture was degassed while being stirred. After that, 136 mg (0.24 mmol) of bis(dibenzylideneacetone)palladium(0) was added to the mixture. This mixture was stirred at 100° C. for 3 hours. After the stirring, about 50 mL of toluene was added to this mixture. The mixture was subjected to suction filtration through Celite (produced by Wako Pure Chemical Industries, Ltd., Catalog No. 531-16855), alumina, and Florisil (produced by Wako Pure Chemical Industries, Ltd., Catalog No. 540-00135). The obtained filtrate was condensed to give a yellow solid. This solid was recrystallized from toluene/hexane to give 6.6 g of a light yellow powder PCBAPA, which was the desired substance, in a yield of 75%.

$^1$H NMR data of the light yellow powder which was obtained by the above synthesis method was measured. The measurement data are shown below. The measurement results show that PCBAPA was obtained.

$^1$H NMR (CDCl$_3$, 300 MHz): δ=7.09-7.14 (m, 1H), 7.28-7.72 (m, 33H), 7.88 (d, J=8.4 Hz, 2H), 8.19 (d, J=7.2 Hz, 1H), 8.37 (d, J=1.5 Hz, 1H).

This application is based on Japanese Patent Application serial no. 2009-085233 filed with Japan Patent Office on Mar. 31, 2009, the entire contents of which are hereby incorporated by reference.

What is claimed is:

1. A carbazole derivative represented by a general formula (1),

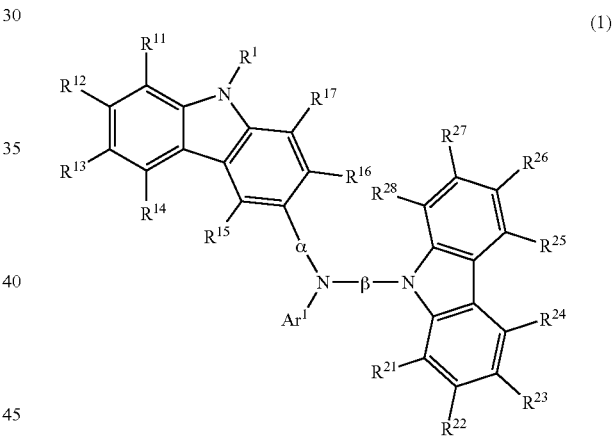

wherein Ar$^1$ represents a substituted or unsubstituted aryl group having 6 to 10 carbon atoms which form a ring; α and β independently represent a substituted or unsubstituted arylene group having 6 to 12 carbon atoms which form a ring; R$^1$ represents an alkyl group having 1 to 4 carbon atoms or a substituted or unsubstituted aryl group having 6 to 10 carbon atoms which form a ring; and R$^{11}$ to R$^{12}$ and R$^{21}$ to R$^{28}$ independently represent hydrogen, an alkyl group having 1 to 4 carbon atoms, or a substituted or unsubstituted aryl group having 6 to 10 carbon atoms which form a ring.

2. A material for a light-emitting element, the material comprising the carbazole derivative according to claim 1.

3. A light-emitting element comprising the carbazole derivative according to claim 1.

4. A light-emitting element wherein the carbazole derivative according to claim 1 is used for a light-emitting layer.

5. A light-emitting element wherein the carbazole derivative according to claim 1 is used as a host material of a light-emitting layer.

6. A light-emitting element wherein the carbazole derivative according to claim 1 is used as a light emission center material.

7. A light-emitting device comprising:

the light-emitting element according to claim 3; and means for controlling the light-emitting element.

8. An electronic device wherein the light-emitting device according to claim 7 is provided in a display portion.

9. A lighting device comprising the light-emitting device according to claim 7.

10. A carbazole derivative represented by a general formula (2),

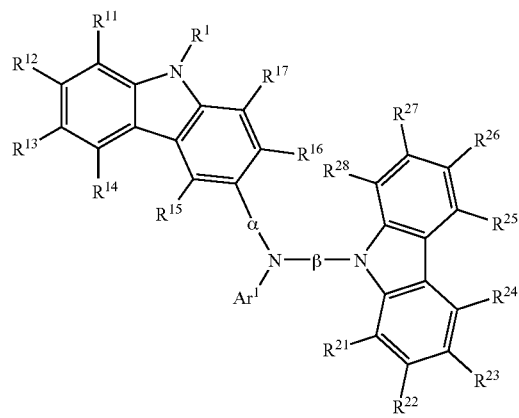

(2)

wherein $Ar^1$ represents a substituted or unsubstituted aryl group having 6 to 10 carbon atoms which form a ring; $\alpha$ and $\beta$ independently represent a substituted or unsubstituted phenylene group; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring.

11. A material for a light-emitting element, the material comprising the carbazole derivative according to claim 10.

12. A light-emitting element comprising the carbazole derivative according to claim 10.

13. A light-emitting element wherein the carbazole derivative according to claim 10 is used for a light-emitting layer.

14. A light-emitting element wherein the carbazole derivative according to claim 10 is used as a host material of a light-emitting layer.

15. A light-emitting element wherein the carbazole derivative according to claim 10 is used as a light emission center material.

16. A light-emitting device comprising:

the light-emitting element according to claim 12; and means for controlling the light-emitting element.

17. An electronic device wherein the light-emitting device according to claim 16 is provided in a display portion.

18. A lighting device comprising the light-emitting device according to claim 16.

19. A carbazole derivative represented by a general formula (3),

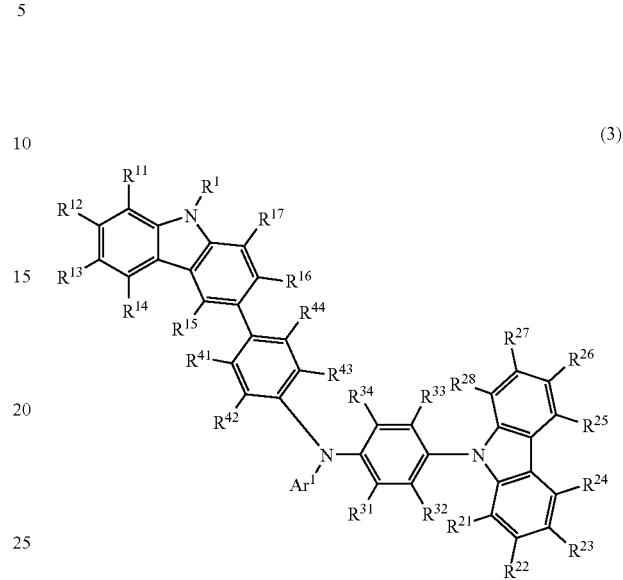

(3)

wherein $Ar^1$ represents a substituted or unsubstituted aryl group having 6 to 10 carbon atoms which form a ring; $R^1$ represents an alkyl group having 1 to 4 carbon atoms or a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; and $R^{31}$ to $R^{34}$ and $R^{41}$ to $R^{44}$ independently represent hydrogen or an alkyl group having 1 to 4 carbon atoms.

20. A material for a light-emitting element, the material comprising the carbazole derivative according to claim 19.

21. A light-emitting element comprising the carbazole derivative according to claim 19.

22. A light-emitting element wherein the carbazole derivative according to claim 19 is used for a light-emitting layer.

23. A light-emitting element wherein the carbazole derivative according to claim 19 is used as a host material of a light-emitting layer.

24. A light-emitting element wherein the carbazole derivative according to claim 19 is used as a light emission center material.

25. A light-emitting device comprising:

the light-emitting element according to claim 21; and means for controlling the light-emitting element.

26. An electronic device wherein the light-emitting device according to claim 25 is provided in a display portion.

27. A lighting device comprising the light-emitting device according to claim 25.

28. A carbazole derivative represented by a general formula (4),

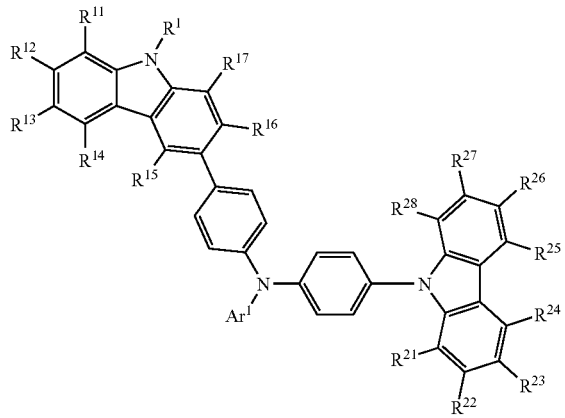

(4)

wherein $Ar^1$ represents a substituted or unsubstituted aryl group having 6 to 10 carbon atoms which form a ring; $R^1$ represents an alkyl group having 1 to 4 carbon atoms or a substituted or unsubstituted aryl group having 6 to 10 carbon atoms which form a ring; and $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring.

29. A material for a light-emitting element, the material comprising the carbazole derivative according to claim 28.

30. A light-emitting element comprising the carbazole derivative according to claim 28.

31. A light-emitting element wherein the carbazole derivative according to claim 28 is used for a light-emitting layer.

32. A light-emitting element wherein the carbazole derivative according to claim 28 is used as a host material of a light-emitting layer.

33. A light-emitting element wherein the carbazole derivative according to claim 28 is used as a light emission center material.

34. A light-emitting device comprising:
the light-emitting element according to claim 30; and
means for controlling the light-emitting element.

35. An electronic device wherein the light-emitting device according to claim 34 is provided in a display portion.

36. A lighting device comprising the light-emitting device according to claim 34.

37. A carbazole derivative represented by a general formula (5),

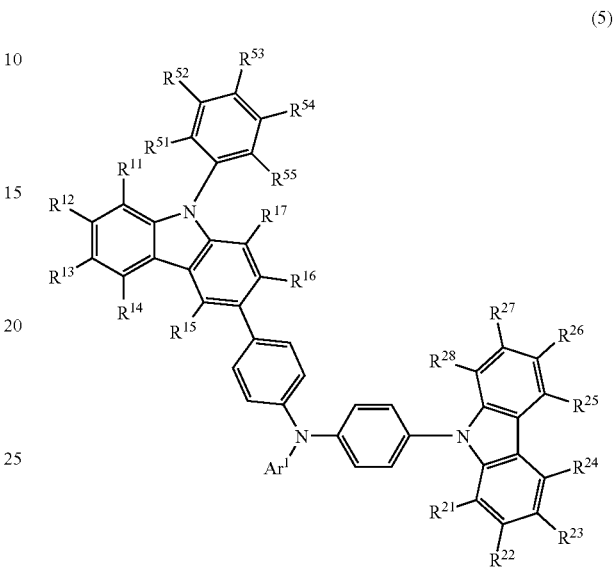

(5)

wherein $Ar^1$ represents a substituted or unsubstituted aryl group having 6 to 10 carbon atoms which form a ring; $R^{11}$ to $R^{17}$ and $R^{21}$ to $R^{28}$ independently represent hydrogen, an alkyl group having 1 to 4 carbon atoms, or a substituted or unsubstituted aryl group having 6 to 10 carbon atoms which form a ring; and $R^{51}$ to $R^{55}$ independently represent hydrogen, an alkyl group having 1 to 4 carbon atoms, or an aryl group having 6 to 10 carbon atoms which form a ring.

38. A material for a light-emitting element, the material comprising the carbazole derivative according to claim 37.

39. A light-emitting element comprising the carbazole derivative according to claim 37.

40. A light-emitting element wherein the carbazole derivative according to claim 37 is used for a light-emitting layer.

41. A light-emitting element wherein the carbazole derivative according to claim 37 is used as a host material of a light-emitting layer.

42. A light-emitting element wherein the carbazole derivative according to claim 37 is used as a light emission center material.

43. A light-emitting device comprising:
the light-emitting element according to claim 39; and
means for controlling the light-emitting element.

44. An electronic device wherein the light-emitting device according to claim 43 is provided in a display portion.

45. A lighting device comprising the light-emitting device according to claim 43.

46. A carbazole derivative represented by a general formula (6),

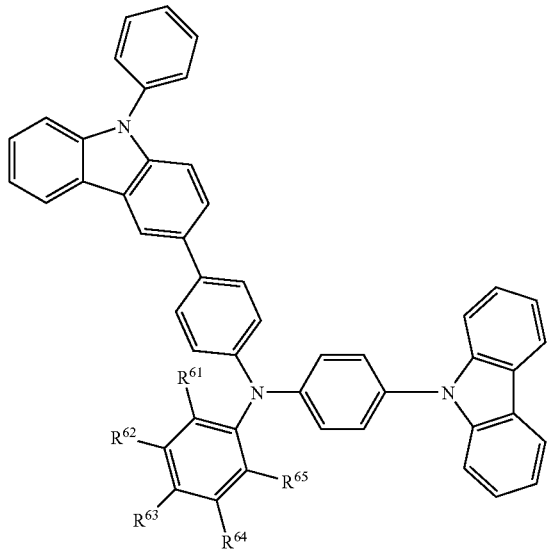

(6)

wherein $R^{61}$ to $R^{65}$ independently represent hydrogen, an alkyl group having 1 to 4 carbon atoms, or an aryl group having 6 to 10 carbon atoms which form a ring.

47. A material for a light-emitting element, the material comprising the carbazole derivative according to claims 46.

48. A light-emitting element comprising the carbazole derivative according to claim 46.

49. A light-emitting element wherein the carbazole derivative according to claim 46 is used for a light-emitting layer.

50. A light-emitting element wherein the carbazole derivative according to claim 46 is used as a host material of a light-emitting layer.

51. A light-emitting element wherein the carbazole derivative according to claim 46 is used as a light emission center material.

52. A light-emitting device comprising:
the light-emitting element according to claim 48; and
means for controlling the light-emitting element.

53. An electronic device wherein the light-emitting device according to claim 52 is provided in a display portion.

54. A lighting device comprising the light-emitting device according to claim 52.

* * * * *

UNITED STATES PATENT AND TRADEMARK OFFICE
CERTIFICATE OF CORRECTION

| | | |
|---|---|---|
| PATENT NO. | : 8,507,695 B2 | Page 1 of 1 |
| APPLICATION NO. | : 12/748532 | |
| DATED | : August 13, 2013 | |
| INVENTOR(S) | : Hiroko Nomura et al. | |

It is certified that error appears in the above-identified patent and that said Letters Patent is hereby corrected as shown below:

In the Specifications:

At column 76, line 35, "RJKEN" should be --RIKEN--;

In the Claims:

In claim 1, at column 86, line 55, "$R^{12}$" should be --$R^{17}$--;

In claim 47, at column 92, line 5, "claims" should be --claim--.

Signed and Sealed this
Twenty-second Day of April, 2014

Michelle K. Lee
*Deputy Director of the United States Patent and Trademark Office*